United States Patent
Potsaid et al.

(10) Patent No.: US 10,215,551 B2
(45) Date of Patent: Feb. 26, 2019

(54) AGILE IMAGING SYSTEM

(71) Applicants: Thorlabs, Inc., Newton, NJ (US);
Praevium Research, Inc., Santa Barbara, CA (US)

(72) Inventors: Benjamin Michael Potsaid, Cambridge, MA (US); James Yi Jiang, Hackettstown, NJ (US); Vijaysekhar Jayaraman, Goleta, CA (US); Scott Barry, Lafayette, NJ (US); Anjul M. Davis Loiacono, Andover, NJ (US); Alex Ezra Cable, Newton, NJ (US)

(73) Assignees: Praevium Research, Inc., Santa Barbara, CA (US); Thorlabs, Inc., Newton, NJ (US)

( * ) Notice: Subject to any disclaimer, the term of this patent is extended or adjusted under 35 U.S.C. 154(b) by 367 days.

(21) Appl. No.: 13/952,574

(22) Filed: Jul. 26, 2013

(65) Prior Publication Data
US 2014/0028997 A1    Jan. 30, 2014

Related U.S. Application Data

(60) Provisional application No. 61/676,876, filed on Jul. 27, 2012.

(51) Int. Cl.
G01B 11/02 (2006.01)
G01B 9/02 (2006.01)
(Continued)

(52) U.S. Cl.
CPC ..... G01B 9/02091 (2013.01); G01B 9/02004 (2013.01); G01B 9/02044 (2013.01);
(Continued)

(58) Field of Classification Search
CPC ........... G01B 9/02091; G01B 9/02044; G01B 9/02004; A61B 3/102; H01S 3/106; H01S 5/183; H01S 3/105; H01S 3/1305
See application file for complete search history.

(56) References Cited

U.S. PATENT DOCUMENTS 5,313,057 A * 5/1994 Nakajima ............ H01S 5/0014
250/214 R
6,263,002 B1 7/2001 Hsu et al.
(Continued)

FOREIGN PATENT DOCUMENTS

CN    101600388 A    12/2009
CN    102440762 A     5/2012
(Continued)

OTHER PUBLICATIONS

Adler, Desmond, "Extended coherence length Fourier domain mode locked lasers at 1310 nm", Oct. 10, 2011.*
(Continued)

Primary Examiner — Maurice Smith
(74) Attorney, Agent, or Firm — Myers Wolin, LLC

(57) ABSTRACT

An agile optical imaging system for optical coherence tomography imaging using a tunable source comprising a wavelength tunable VCL laser is disclosed. The tunable source has long coherence length and is capable of high sweep repetition rate, as well as changing the sweep trajectory, sweep speed, sweep repetition rate, sweep linearity, and emission wavelength range on the fly to support multiple modes of OCT imaging. The imaging system also offers new enhanced dynamic range imaging capability for accommodating bright reflections. Multiscale imaging capability allows measurement over orders of magnitude dimensional scales. The imaging system and methods for generating the
(Continued)

waveforms to drive the tunable laser in flexible and agile modes of operation are also described.

52 Claims, 54 Drawing Sheets

(51) Int. Cl.
   *H01S 5/183* (2006.01)
   *A61B 5/00* (2006.01)
   *A61B 3/10* (2006.01)

(52) U.S. Cl.
   CPC ..... *G01B 9/02067* (2013.01); *G01B 9/02069* (2013.01); *H01S 5/18366* (2013.01); *A61B 3/102* (2013.01); *A61B 5/0066* (2013.01)

(56) References Cited

U.S. PATENT DOCUMENTS

| | | | |
|---|---|---|---|
| 7,769,419 B2 | 8/2010 | Daly | |
| 2003/0016709 A1* | 1/2003 | Flanders | H01S 5/141 372/26 |
| 2006/0187537 A1* | 8/2006 | Huber | H01S 3/106 359/337.22 |
| 2007/0183643 A1* | 8/2007 | Jayaraman | A61B 3/102 382/131 |
| 2008/0165366 A1 | 7/2008 | Schmitt | |
| 2008/0205717 A1* | 8/2008 | Reeves | G06T 7/0012 382/128 |
| 2009/0131801 A1 | 5/2009 | Suter et al. | |
| 2009/0174931 A1* | 7/2009 | Huber | H01S 3/1106 359/340 |
| 2009/0284749 A1* | 11/2009 | Johnson | A61B 5/0066 356/497 |
| 2009/0303487 A1 | 12/2009 | Bond et al. | |
| 2010/0189141 A1* | 7/2010 | Zhang | H01S 5/065 372/18 |
| 2010/0226554 A1* | 9/2010 | Suehira | A61B 3/102 382/131 |
| 2011/0080591 A1* | 4/2011 | Johnson | G01B 9/02004 356/479 |
| 2011/0255095 A1 | 10/2011 | Jiang et al. | |
| 2012/0013915 A1* | 1/2012 | Okamura | A61B 3/102 356/479 |
| 2012/0026503 A1 | 2/2012 | Lewandowski et al. | |
| 2012/0162659 A1 | 6/2012 | Goldberg et al. | |

FOREIGN PATENT DOCUMENTS

| | | | |
|---|---|---|---|
| JP | 2007278868 A | | 10/2007 |
| JP | 2008304314 A | | 12/2008 |
| JP | WO2012093654 A1 * | | 7/2012 |

OTHER PUBLICATIONS

Huber, R, "Fourier domain mode locking at 1050 nm for ultra-high-speed optical coherence tomography of the human retina at 236,000 axial scans per second", Jul. 10, 2007.*

Toshihiko Baba,"Spontaneous Emission Factor of a Microcavity DBR Surface-Emitting Laser",IEEE Journal of Quantum Electronics, vol. 21, No. 6, Jun. 1991, p. 1354.*
International Search Report mailed Oct. 22, 2013 in corresponding International Application No. PCT/US2013/052425.
International Search Report mailed Feb. 5, 2015 in corresponding International Application No. PCT/US2013/052425.
Extended European Search Report mailed Apr. 21, 2016 in corresponding International Application No. PCT/US2013/052425 and European Application No. EP13823671.6.
Potsaid, Benjamin et al: "MEMS tunable VCSEL light source for ultrahigh speed 60kHz-1MHz axial scan rate and long range centimeter class OCT imaging", Proc. SPIE 8213, Optical Coherence Tomography and Coherence Domain Optical Methods in Biomedicine XVI, 82130M (Feb. 9, 2012); doi:10.1117/12.911098.
Jayaraman, V et al: "Design and performance of broadly tunable, narrow line-width, high repetition rate 1310nm VCSELs for swept source optical coherence tomography", Proc. SPIE 8276, Vertical-Cavity Surface-Emitting Lasers XVI, 82760D (Feb. 9, 2012); doi:10.1117/12.906920.
Roos P A et al:"Ultrabroadband optical chirp linearization for precision metrology applications," Opt. Lett. 34, 3692-3694 (2009).
State Intellectual Property Office of the P.R.C. (SIPO) First Office Action, for corresponding China Application No. 201380048698.8 issued on Jul. 27, 2016.
Chen, Minghui, "Development of frequency swept laser", Chinese Doctoral dissertation information technology series, No. 7, p. I135-30, Jul. 15, 2012.
Chinese Second Office Action and Full English translation, issued by the State Intellectual Property Office of the P.R.C. (SIPO) dated Mar. 23, 2017 for corresponding China application No. 201380048698.8.
Japanese Notice of Reasons for Rejection, issued by the Japanese Patent Office dated Mar. 28, 2017 for corresponding Japan application No. 2015-524498.
USPTO Non-Final Office action dated Aug. 3, 2017, for corresponding U.S. Appl. No. 15/477,850.
Japanese Decision of Rejection, and Full English translation, issued by the Japanese Patent Office dated Nov. 14, 2017 for corresponding Japan application No. 2015-524498.
V. Jayaraman, J. Jiang, H. Li, P. Heim, G. Cole, B. Potsaid, J. G. Fujimoto, and A. Cable, "OCT Imaging up to 760Khz Axial Scan Rate Using Single-Mode 1310nm MEMs-Tunable VCSELs with >100nm Tuning Range," in CLEO: 2011—Laser Applications to Photonic Applications, OSA Technical Digest (CD) (Optical Society of America, 2011), paper PDPB2.
Chinese First Office Action issued by the State Intellectual Property Office of the P.R.C. (SIPO) dated Jul. 27, 2016, and English translation of the first 2 pages for corresponding China application No. 201380048698.8.
Chinese Notice of Allowance and Full English translation dated Oct. 10, 2017, by the State Intellectual Property Office of the P.R.C. (SIPO) for corresponding China application No. 201380048698.8.
Chinese First Office Action issued by the State Intellectual Property Office of the P.R.C. (SIPO) dated Jul. 30, 2018 for corresponding China application No. 2017103798820, with an English Translation.

* cited by examiner

Linearized VCSEL module profiles driven by 100kHz custom waveform (A) MEMS VCSEL laser driven at 500 kHz. (B) an OCT image of human finger pad constructed by 4096 A-Scans width image size of 5 mm x 3 mm (width x depth)

AGILE IMAGING SYSTEM

CROSS REFERENCES TO RELATED APPLICATIONS

This application claims the benefit of U.S. Provisional Patent Application No. 61/676,876 filed on Jul. 27, 2012. The disclosure and entire teachings of U.S. Provisional Patent Application 61/676,876 are hereby incorporated by reference.

FIELD OF THE INVENTION

The present invention relates to the field of Optical Coherence Tomography (OCT) imaging.

BACKGROUND

Optical Coherence Tomography (OCT) is a non-invasive, interferometric optical imaging technique that can generate micron resolution 2D and 3D images of tissue and other scattering or reflective materials. OCT is often used for biomedical imaging or materials inspection. First demonstrated for imaging the human eye and coronary arteries in 1991, OCT has since been established as a clinical standard for diagnosing and monitoring treatment of eye disease. OCT is also used for intravascular imaging of plaque to assess heart disease, cancer biopsy imaging, developmental biology research, art preservation, industrial inspection, metrology, and quality assurance. In general, OCT is useful for applications that benefit from subsurface imaging, surface profiling, motion characterization, fluid flow characterization, index of refraction measurement, birefringence characterization, scattering characterization, or distance measurement.

Optical Coherence Tomography uses the interference pattern obtained by combining light backscattered or back-reflected from a sample with light from a reference arm to determine spatially dependent properties of the sample, as illustrated in FIG. 1A. Time Domain OCT (TD-OCT) imaging principles were used in the first demonstrations and commercial products for OCT. However, TD-OCT is known to be a slow technology for acquiring OCT data. Fourier Domain OCT (FD-OCT) enables orders of magnitude faster imaging speeds than TD-OCT and has become the current research and commercial standard. Fourier Domain OCT can be implemented with a broadband light source, interferometer, spectrometer, and linescan camera, called Spectral Domain OCT (SD-OCT), as illustrated in FIG. 1B. Scanning the light across a sample (FIG. 1C) allows the collection of a complete reflectivity vs. depth profile, called an A-scan (FIG. 1D), for each point of interrogation. Scanning and assembling sequentially acquired A-scans allows 2D images to be formed, called B-scans (FIG. 1E). 3D volumes are also formed by scanning across the sample in two directions (FIG. 1F). Fourier Domain OCT can also be implemented with a wavelength swept light source, interferometer, detector, and analog to digital converter (A/D), called Swept Source OCT (SS-OCT) or optical frequency domain imaging (OFDI), as illustrated in FIGS. 2A and 2B. For the purposes of this disclosure, Swept Source OCT and OFDI are equivalent. The two variations of Fourier Domain OCT, being Spectral Domain OCT and Swept Source OCT, represent the state of the art in OCT imaging technologies.

Spectral Domain OCT suffers from an inherent and problematic loss of OCT sensitivity with increasing imaging depth, often called sensitivity roll-off, sensitivity fall-off, or sensitivity drop. The loss of OCT sensitivity with increasing depth is caused by a reduction in the interferometric fringe visibility due to limits in the spectrometer resolution, integration of multiple wavelengths over a pixel width, and inter-pixel crosstalk, as described in the papers, "Analytical model of spectrometer-based two-beam spectral interferometry," Hu, Pan, and Rollins, Applied Optics, Vol. 46, No. 35, pp. 8499-8505, 2007 and "Improved spectral optical coherence tomography using optical frequency comb," Bajraszewski et al. Optics Express, Vol. 16, No. 6, pp. 4163-4176, 2008.

A paper, "Fourier domain optical coherence tomography with a linear-in-wavenumber spectrometer," Hu and Rollins, Optics Letters, Vol. 32, No. 24, pp. 3525-3527, 2007, teaches linearizing the spectral dispersion of the spectrometer in wavenumber using a specifically designed prism. The spectral linearity in wavenumber results in improvement of the fall-off of signal with imaging range inherent to spectral domain optical coherence tomography imaging. Although there is improvement, the loss of sensitivity with imaging depth is still significant, especially when used with wide spectral bandwidth sources for achieving a fine OCT axial resolution.

A paper, "Improved spectral optical coherence tomography using optical frequency comb," Bajraszewski et al. Optics Express, Vol. 16, No. 6, pp. 4163-4176, 2008, teaches using a Fabry-Perot optical frequency comb in a Spectral Domain OCT system to reduce the depth dependent drop of sensitivity. The approach has several significant disadvantages. Insertion of the frequency comb reduces optical power levels, which compromises baseline OCT sensitivity. The approach also requires that the optical frequency comb be actively tuned and multiple spectrometer measurements performed for every A-scan in order to fill gaps in spectral data content that are filtered out by the Fabry-Perot filter. In practice, four camera exposures were shown to enable OCT imaging, which results in a significant reduction in OCT imaging speed.

Various so called "full range" or "complex conjugate" approaches have been proposed to extend the imaging range and help mitigate the problem of sensitivity roll-off associated with Spectral Domain OCT. These approaches do not fully suppress complex conjugate artifacts in the images, require considerable computation, and often require multiple acquisitions to construct each A-scan, so are not suitable for high dynamic range and high speed OCT acquisition. Further, maximum imaging speeds with Spectral Domain OCT are limited to several hundred kilohertz A-scan rate due to limits in linescan camera speeds. These inherent characteristics and deficiencies combined suggest that Spectral Domain OCT is not the technology of choice for long range, high speed, and high dynamic range imaging.

Swept Source OCT uses a wavelength swept laser as the light source and a detector with high speed A/D converter to sample the interferometric OCT signal. Sensitivity roll-off performance in Swept Source OCT is generally significantly better than Spectral Domain OCT. Swept Source OCT has also achieved higher imaging speeds and longer imaging range than Spectral Domain OCT.

Many different swept laser configurations and wavelength tuning mechanisms have been implemented for Swept Source OCT that either include a wavelength selective intracavity filter or wavelength selective laser cavity end mirror. Examples include: galvo-grating wavelength selective end mirror designs (Chinn, Swanson, and Fujimoto, Optics Letters, Vol. 22, No. 5, pp. 340-342, 1997), rotating polygon mirror-grating filter designs (Yun et al., Optics Letters, Vol. 28, No. 20, pp. 1981-1983, 2003), fiber ring lasers with intracavity wavelength selective filter (Huber et al., Optics Express Vol. 13, No. 9, pp. 3513-3528, 2005), and short cavity microelectromechanical systems (MEMS) filter based tunable lasers (WO 2010/111795 A1). In all of these swept laser designs, lasing builds from amplified spontaneous emission (ASE) as the filter is tuned such that the photon round trip time is significant, and along with cavity efficiency and filter width, define a maximum sweep speed at which the laser can be swept while still maintaining full saturation of the optical gain medium. Sweep repetition rates in the tens of kilohertz to low hundreds of kilohertz are generally possible with these technologies, but the sweep speed is still fundamentally limited due to the relatively long photon round trip time.

U.S. Patent Application No. 2006/0187537 A1 teaches a different swept source laser technology, called a Fourier Domain Mode Locked (FDML) laser. An FDML laser operates with a principle that enables higher sweep speeds. In an FDML laser, a long fiber loop is used to store the wavelength sweep and a filter is tuned in synchronization with the returning sweep wavelength, either before or after optical amplification. The FDML approach reduces the need to build up lasing from ASE to achieve high fundamental sweep repetition rates up to about 500 kHz axial scan rate. Through replicating, delaying, and multiplexing the sweep, buffered speeds up to about 5 MHz axial scan rate can be achieved for a single imaging spot (Wieser et al., Optics Express, Vol. 18, No. 14, 2010). A significant drawback of a typical FDML laser is a short a coherence length of about 4-10 mm, which significantly limits OCT imaging range.

In Swept Source OCT, sensitivity roll-off is limited by the coherence length of the wavelength tunable laser source, which is determined by the instantaneous linewidth of the laser. In all of the swept lasers describe thus far, the filter in the laser is designed to tune multiple laser longitudinal modes. As taught by International Patent Application Publication No. WO 2010/111795 A1 and Huber et al., Optics Express Vol. 13, No. 9, pp. 3513-3528, 2005, the wavelength selective filter in a traditional swept laser design spans multiple longitudinal laser modes in order to achieve high sweep rates and prevent laser power drop off and laser noise due to mode-hopping. In the case of the FDML laser, the reason for designing a relatively wide spectral filter width is related to dispersion in the fiber loop that causes a wavelength dependent round trip time, requiring the filter to be wide enough to transmit the full range of slow to fast wavelengths in the fiber loop. Regardless of the reason for needing to use a wide filter that spans multiple laser longitudinal modes, the result is a laser with a relatively wide instantaneous linewidth with compromised coherence length, OCT imaging range, and OCT sensitivity roll-off.

A paper, "Extended coherence length Fourier domain mode locked lasers at 1310 nm", Adler et al., Optics Express, Vol. 19, No. 21, pp. 20931-20939, 2011 teaches a method to improve the coherence length of an FDML laser by adding a chirped fiber Bragg grating dispersion compensation module to improve the dispersion characteristics of the fiber loop. Improved laser coherence length to about 21 mm and the ability to use both the forwards and backwards sweeps were obtained.

In nearly all implementations to date, Spectral Domain OCT systems and Swept Source OCT systems have been designed to operate at a fixed imaging speed, fixed imaging range, and fixed OCT axial resolution. Generally, the entire OCT imaging system is optimized for a specific application.

With the introduction of high speed CMOS linescan camera technology with programmable speed and programmable active pixel count, it became possible to trade off pixel count to gain imaging speed in Spectral Domain OCT.

A paper, "Ultrahigh speed Spectral/Fourier domain OCT ophthalmic imaging at 70,000 to 312,500 axial scans per second," Potsaid et al., Optics Express, Vol. 16, No. 19, pp. 15149-15169, 2008, teaches operating a Spectral Domain OCT system using a CMOS camera with adjustable active pixel count in different configurations to achieve: long imaging range with fine axial resolution and moderate OCT imaging speed, short imaging range with fine axial resolution at faster imaging speeds, and short imaging range with compromised axial resolution at ultrafast imaging speeds. Each configuration was optimized for sensitivity and imaging performance. A significant drawback of the approach is that the light source must be interchanged and the spectrometer rebuilt with different components for the multiple configurations and operating modes.

A paper, "High-Speed High-Resolution Optical Coherence Tomography at 800 and 1060 nm", Povazay et al., Proceedings of SPIE, vol. 7139, pp. 71390R-1-7, 2008, teaches an OCT imaging system using a programmable CMOS camera with a fixed light source in which the number of pixels used in the camera is reduced in order to achieve higher imaging speeds by truncating the spectrum. A significant disadvantage of this method is that the spectrometer is not reoptimized to the light source bandwidth for the different operating modes, so light falls on unused pixels for the higher speed imaging configurations and there is an associated loss of OCT sensitivity.

A paper, "Ultra high-speed swept source OCT imaging of the anterior segment of human eye at 200 kHz with adjustable imaging range," Gora et al, Optics Express, Vol. 17, No. 17, pp. 14880-14894, 2009, teaches a Swept Source OCT imaging systems using an FDML laser that trades off OCT axial resolution to gain imaging range. A disadvantage of this approach is that the FDML laser must be run at a harmonic of the sweep frequency, so the sweep repetition rate of the OCT imaging system cannot be changed without significant reconfiguration.

A new swept light source for use with Swept Source OCT has been developed that overcomes many of the above mentioned limitations associated with previous OCT technologies.

U.S. Pat. No. 7,468,997 B2 teaches a swept source optical coherence tomography system (SS-OCT) comprising a vertical cavity surface-emitting laser (VCSEL) with an integrated MEMs tunable mirror movable by electro-static deflection. A paper, "OCT Imaging up to 760 kHz Axial Scan Rate Using Single-Mode 1310 nm MEMS-Tunable VCSELs with >100 nm Tuning Range," Jayaraman et al., Optical Society of America, CLEO Conference, pp. PDPB1-PDPB2, 2011, experimentally demonstrates the first widely tunable, single-mode 1310 nm MEMS VCSELs with >100 nm tuning range, and the first application of these VCSELs to ultra-high-speed swept source OCT imaging at axial scan rates up to 760 kHz. Unlike other swept laser sources, which use a short cavity and intra-cavity filter, VCSELs operate with a true single-longitudinal mode instead of a set of modes. The true single-longitudinal mode operation results in a long coherence length for the VCSEL technology. Further, forward and backward scans show comparable performance, in contrast to other swept sources, enabling use of both the forwards and backwards sweeps for OCT imaging.

The limited imaging speed, limited imaging range, loss of sensitivity with increasing imaging depth, and operation at a predominately fixed imaging mode of previous OCT technologies result in a compromise of OCT imaging performance and limit application of OCT technology.

SUMMARY

An embodiment of the present invention is an optical coherence tomography imaging system using a vertical cavity laser (VCL) source and methods for its operation. Unique and advantageous capabilities and functionalities of embodiments of the present invention are enabled by the incorporation of a new tunable VCL source technology in a novel imaging system architecture. An embodiment of the present invention offers speed, imaging range, and size improvements over existing approaches. Further, an embodiment of the present invention enables switching between different imaging modes defined by imaging speed, imaging range, and imaging resolution, making the present invention more agile and flexible during use when compared to existing approaches. One embodiment offers enhanced dynamic range imaging capability for accommodating bright reflections. One embodiment offers multiscale imaging capability for measurement over orders of magnitude dimensional scales. The imaging system and methods for generating the waveforms to drive the tunable laser in flexible and agile modes of operation are also described. The possible areas of use include medical imaging, biological imaging, industrial inspection, material inspection, subsurface imaging, surface profiling, distance ranging and measurement, fluid flow characterization and analysis, and investigation and characterization of material polarization properties.

One embodiment provides an optical imaging system, including: a tunable source including a wavelength tunable vertical cavity laser (VCL) and intracavity tuning element generating a single longitudinal mode output that is tunable over an emission wavelength range for generating wavelength sweeps; a tuning driver, the tuning driver being capable of generating one or more wavelength tuning waveforms to affect the tuning element which determines the sweep trajectory, sweep speed, sweep repetition rate, sweep linearity, and emission wavelength range; a current driver that supplies current to a gain material within the tunable source to adjust output optical radiation power; a monitoring detector to measure attributes of the tuning response and provide feedback to correct for disturbances to the tunable source or to generate wavelength tuning waveforms; an optical interferometer with a reference arm and a sample arm illuminated by said tunable source; one or more optical detectors that convert optical interference fringe signals from the optical interferometer into electric analog signals; a data acquisition device to convert the electric analog signals output from the one or more detectors into digital data.

Another embodiment provides an optical coherence tomography imaging system including: a VCL source that has the characteristics of being able to image over adjustable depth ranges, axial resolutions, and at continuously adjustable speeds, the optical coherence tomography system being able to image over an extended imaging range enabled by the long coherence length of the VCL source.

Another embodiment provides a method for generating a tuning waveform of the above optical imaging system, the method including: expressing the tuning waveform as a function of adjustable input parameter values to create a tuning waveform expression; applying the tuning waveform to the tuning element or a mathematical model of the tunable source dynamics to generate at least one experimental measurement or simulated wavelength sweep; calculating a value of a performance metric or an objective function based on the experimental measurement or the simulated wavelength sweep; adjusting the value of the input parameters to optimize the value of the performance metric or objective function.

DETAILED DESCRIPTION

Figure 1:
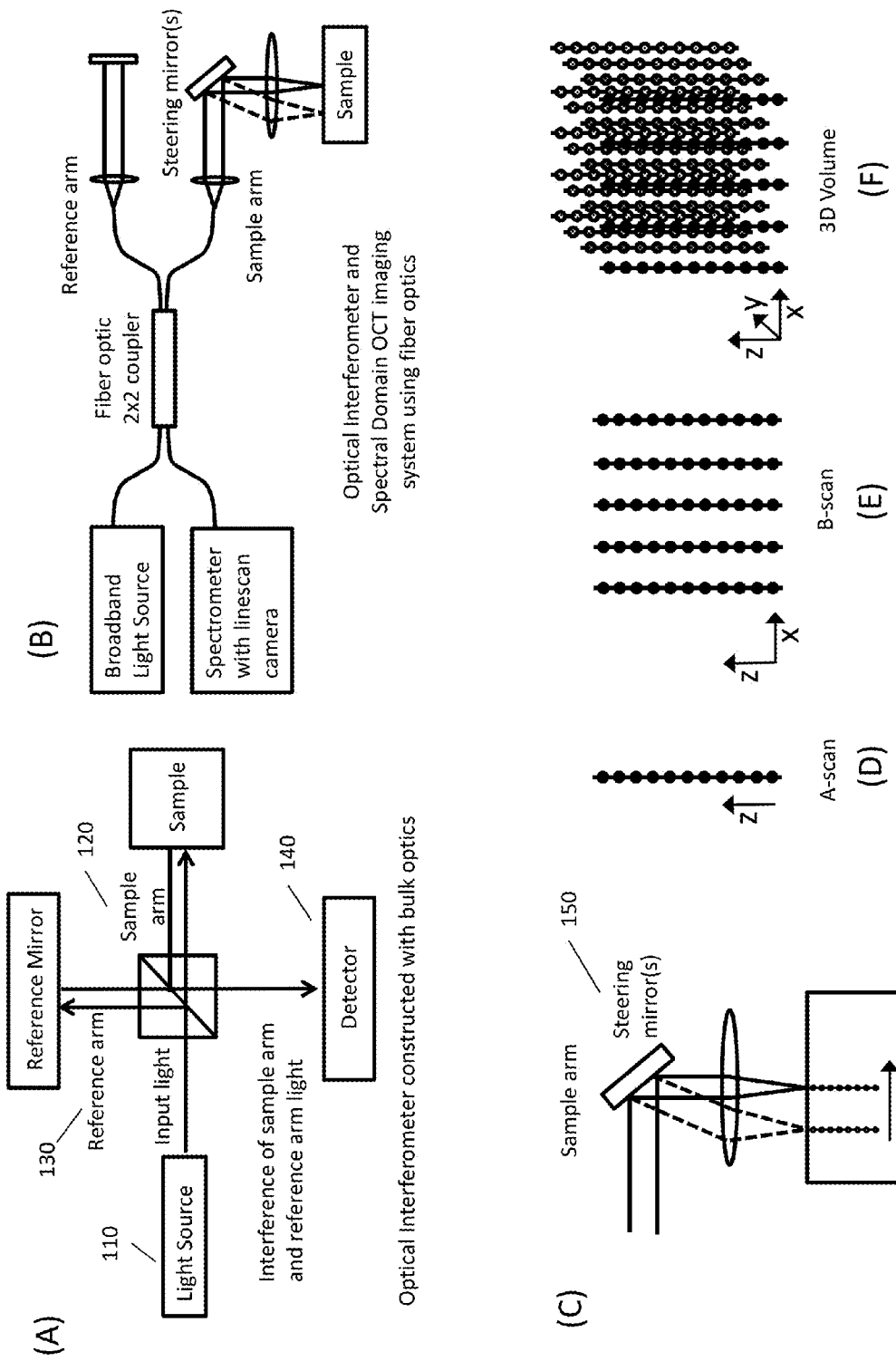
FIG. 1 is a set of drawings illustrating OCT system layouts and OCT scanning.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

This detailed description describes embodiments of the present invention and is broken into sections related to the different aspects of the present invention for clarity.

OCT Imaging Applications of the Preferred Embodiment

The preferred embodiment of the present invention offers traditional OCT imaging performance superior to previously demonstrated OCT technologies when used in many existing OCT applications, such as the applications described in the Background section of this disclosure and including ophthalmic imaging, intravascular imaging, cancer biopsy imaging, developmental biology research, medical diagnostics, surgery guidance, art preservation, industrial inspection, metrology, and quality assurance. More generally the present invention can be practiced for applications that benefit from subsurface imaging, surface profiling, motion characterization, fluid flow characterization, index of refraction measurement, birefringence characterization, scattering characterization, or distance measurement. The preferred embodiment can be practiced in all fields in which OCT imaging would be considered.

The preferred embodiment offers OCT imaging capability previously not available, including: extremely long imaging range, high fundamental imaging speeds, and ability to change imaging speed, imaging sweep trajectory, imaging resolution, and imaging range on the fly to support multiple modes of OCT imaging. The preferred embodiment also offers new enhanced dynamic range imaging capability for accommodating bright reflections and multiscale imaging capability for measurement over orders of magnitude dimensional scales. The new capabilities of the preferred embodiment make the present invention enabling for new applications of OCT. For example, the present invention enables imaging, profiling, and measurement of large objects and samples in a manufacturing, diagnostic, medical, or research environment. Examples of new applications include placing a sample delivery optic or scanner on the end of a robot arm or gantry for inspection of manufactured goods by surface profiling and distance measurement, measuring part placement during assembly, inspecting parts for wear or damage, investigating stress levels in materials, and other applications. The different imaging modes of the OCT system can be selected by a user as required by the imaging application at hand, can be preprogrammed to switch according to a schedule or plan, as would be useful in a manufacturing environment, or can be adapted by an algorithm based on OCT measurements performed in realtime.

From an original equipment manufacturer (OEM) perspective, the flexible operation of the preferred embodiment of the present invention allows a single core OCT module or engine to be used in multiple products or in a single product for multiple applications, thereby simplifying system design, stocking, and inventory control in addition to offering higher value to the customer.

OCT Detection Methods And Principles

The preferred embodiment uses OCT detection methods which operate by interferometrically detecting backscattered and reflected light from a sample. All OCT systems comprise at a minimum a light source 110, interferometer with sample arm 120 and reference arm 130, and a detector 140 to acquire the interferometric signal, as illustrated in FIG. 1A.

The preferred embodiment uses a scanner for scanning the sample light across the sample. The scanner in one embodiment is a rotating mirror as is common in ophthalmic OCT, a side viewing rotating probed as is common in intravascular OCT, a forwards looking probe with lateral scanning capability, or any other method for scanning light across the sample. The scanner in one embodiment is a moving stage or conveyor belt, allowing the OCT optics to remain stationary and unactuated. The scanner in another embodiment is a mobile robot, robotic arm, gantry, or other actuated motion generating platform, with either an unactuated sample arm optic or a sample arm optic with integrated scanning capability. Using the example of a galvanometer and mirror based scanner 150 that is common in OCT and shown in FIG. 1C, OCT data acquisition is described next. OCT systems generally focus a light spot on a sample and collect a reflectivity vs. depth profile at a single transverse location on the sample, called an A-scan (FIG. 1D). The light spot on the sample can be scanned across the sample and multiple depth interrogations performed, each depth interrogation being an A-scan. Assembling the sequential A-scans obtained as the beam is scanned across the sample generates a 2D image of the sample, called a B-scan (FIG. 1E) or sometimes called an OCT cross sectional image. Multiple B-scans can be acquired using a raster scanning pattern to collect a 3D volumetric data set (FIG. 1F). Other scan patterns are possible, such as circles, concentric circles, spirals, or parking the scanners in one location to get multiple A-scans from the same location, called M-mode imaging. M-mode imaging is useful for imaging dynamic processes and can achieve a high temporal sample rate to capture fast dynamics. However, M-mode imaging is limited to obtaining information localized to a line in the sample corresponding to the A-scan location because there is no scanning performed. Acquiring multiple 3D data sets from the same location on the sample can generate 4D OCT data to form a volumetric time dependent movie of the sample, but at a reduced frame rate compared to M-mode imaging. Lower order time dependent acquisitions can be acquired, such as repeating a B-scan at the same location, to create a 2D movie. Repeating B-scans is also used to detect small changes in the sample over time, indicative of action or motion within the sample. Repeating B-scans as part of the collection of a 3D volume can generate 3D volumes that characterize motion on a time scale faster than allowed by repeating the full 3D volume. The scan patterns described so far generally relate to point sampling or point scanning OCT methods. It is also possible to perform parallel detection by implementing line scan OCT or full field OCT, using a 1D array camera or 2D array, respectively, or imaging with multiple spots, which are also included in some embodiments of the current invention.

The preferred embodiment of the present invention implements swept source OCT. Many optical designs can be used to construct the OCT interferometer with the preferred design being application and cost specific. Two possible interferometer designs are shown in FIGS. 2A and 2B. These figures show different sample arm light delivery optics, one design for compatibility with the optics in the human eye (FIG. 2A) and one for imaging a more standard sample without integrated optics (FIG. 2B). Sample arm delivery optics and interferometer designs can be interchanged as appropriate to the imaging application. Interferometer designs and sample optics different than those shown are possible and included in an embodiment of the present invention. In general, the interferometer and sample arm optics will be optimized for a specific application or class of applications. Fiber optic components used in the interferometer can simplify alignment and improve stability, although bulk optics interferometers can also be used. One embodiment of the present invention uses an interferometer comprising bulk optics. Another embodiment of the present invention uses an interferometer comprising fiber optic components. OCT systems can be built with bulk optics interferometers or fiber interferometers or a combination of both. The interferometer design illustrated in FIG. 2A works for OCT imaging at all wavelengths, but a portion of the light collected by the sample is redirected to the source through the first fiber coupler 210 and never reaches the detector, resulting in a loss of interferometer efficiency. The design illustrated in FIG. 2B includes circulators 220, 230. High efficiency circulators are available at 1310 nm and other wavelengths, whereas circulators at 850 nm and 1050 nm wavelengths are less efficient. One embodiment of the present invention uses circulators to improve interferometer efficiency.

Swept Source OCT systems operate by sweeping an emission wavelength in time, using the emission as an input to an OCT interferometer, detecting the interferometric signal from the interferometer, and digitizing the signal for analysis, as illustrated in FIG. 3A. For illustrative purposes, the example fringe 310 shown in FIG. 3A is roughly the fringe pattern that would be expected from a single mirror reflection as recorded by a Swept Source OCT system. To understand Swept Source OCT imaging principles and system limitations, it is helpful to consider the OCT signal from a mirror reflection under different imaging configurations. Refer to Eq. 1 below, where $k_m$ is the wavenumber at sample point m, $I[k_m]$ is the instantaneous photocurrent at sample point m, $\rho[k_m]$ is the detector responsively at sample point m, $S[k_m]$ is the instantaneous power on the sample at sample point m, $R_R$ is the reflectivity of the reference mirror, $R_S$ is the reflectivity of the sample mirror, $z_r$ is the depth of the reference mirror, and $z_s$ is the depth of the sample arm mirror. Equation 1 was adapted from J. A. Izatt and M. A. Choma, Section 2.7, W. Drexler and J. G. Fujimoto Ed., "Optical Coherence Tomography: Technology and Applications", 2008. In practice, the photocurrent, I, is generally transformed into a voltage by a transimpedance amplifier before A/D digitization.

$$I[k_m] = \frac{\rho[k_m]}{2} S[k_m](R_R + R_S + 2\sqrt{R_R R_S} \cos(2k_m(z_r - z_s))) \quad \text{Eq. 1}$$

The term inside the cosine function represents the phase of the OCT fringe. As the phase increases (or decreases), the OCT fringe oscillates with a full period of oscillation occurring every $2*\pi$ radians. A wavelength sweep has a starting wavenumber, $k_{start}$ and an ending wavenumber, $k_{end}$. The number of oscillations in the OCT fringe is proportional to the magnitude of the total phase difference, $\Delta\Phi$, over the sweep, which is given by $$\Delta\Phi = 2(k_{end} - k_{start})(z_r - r_s). \quad \text{Eq. 2}$$

Figure 3:
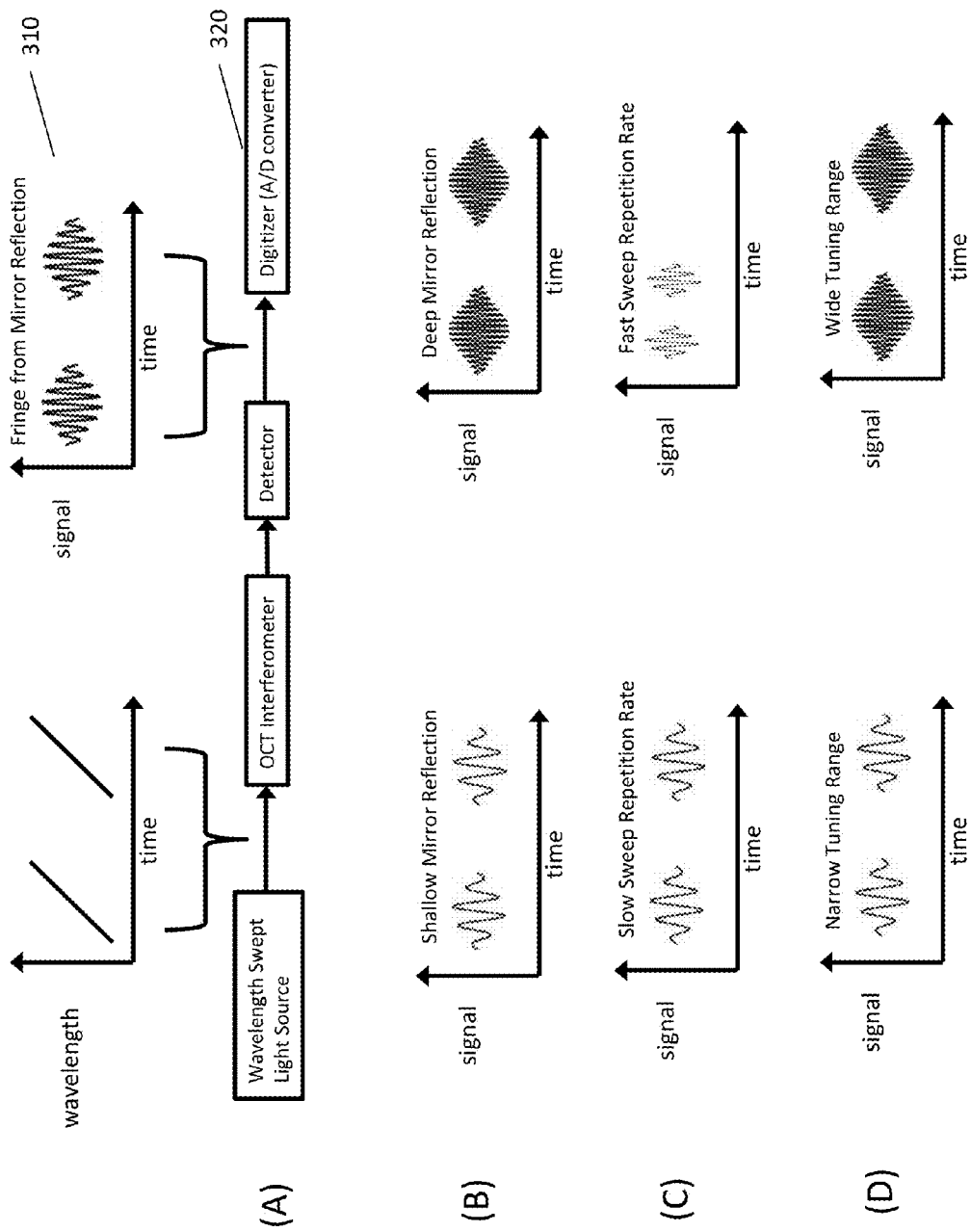
FIG. 3 is a set of drawings and plots illustrating Swept Source OCT fringe formation.
Figure 4:
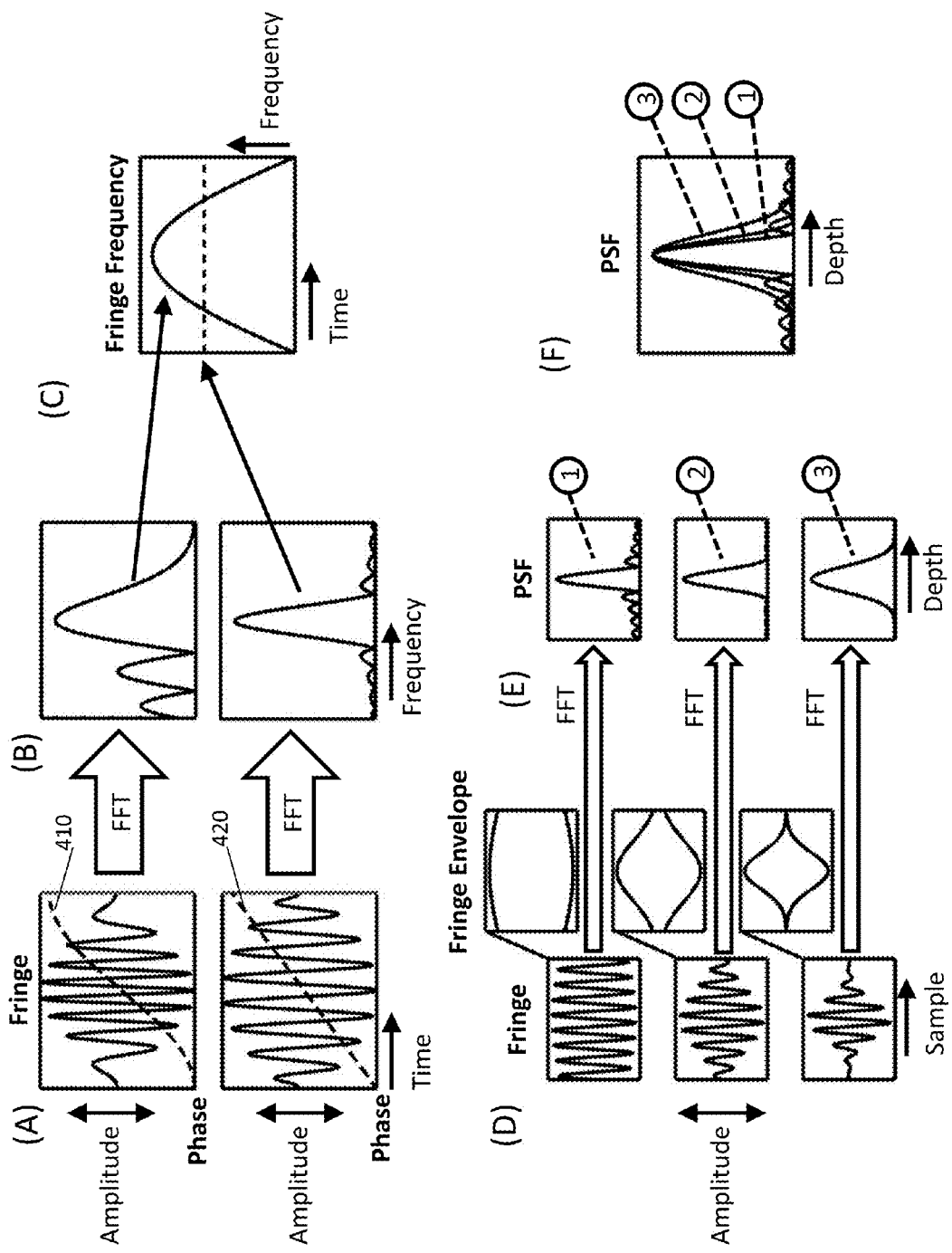
FIG. 4 is a set of plots illustrating sweep trajectory and fringe envelope effects on OCT acquisition and point spread function formation.

Equation 2 shows that the fringe frequency increases with increasing imaging depth (i.e., there is a larger number of oscillations over the sweep) because the $(z_r - z_s)$ multiplier term inside the cosine function increases total fringe phase, as illustrated in FIG. 3B. All other sweep characteristics being equal, the fringe frequency increases with increasing sweep repetition rate for a given mirror position, as illustrated in FIG. 3C, because the same number of fringe oscillations occur over a shorter time. Similarly, with all other sweep characteristics being equal, the fringe frequency increases with increasing wavelength sweep range for a given mirror position, as illustrated in FIG. 3D, because the total phase difference increases due to the larger $(k_{end} - k_{start})$ term. FIG. 4A shows an additional effect on fringe frequency in that the fringe frequency is also determined by the sweep trajectory. A sweep that has slow and fast portions, such as that produced with a sine wave trajectory 410 for example, has a peak fringe frequency where rate of change in wavenumber (k) vs. time is greatest. To the designer of an OCT imaging system, the consequences of these effects on fringe frequency are significant because of limitations and challenges associated with detecting and digitizing the fringe. In order to prevent aliasing of the fringe signal, the analog to digital converter (A/D) 320 must sample at least two times as fast as the fringe frequency, according to Nyquist sampling criteria. It is therefore preferential to linearize the sweep frequency so that the sweep is linear 420 in k-space (wavenumber) vs. time, as shown in FIG. 4A bottom, or to more generally minimize the peak fringe frequency to maximize OCT imaging range for a given maximum digitization rate. As the sampling rate of A/D converters increases, the cost of the A/D itself increases along with the cost, complexity, and timing requirements of the associated support electronics, data streaming mechanisms, and data storage. It is therefore often not feasible to simply choose a fast A/D converter rate and a compromise must be made in maximum obtainable data bandwidth (analog detection bandwidth, A/D rate, data streaming, and storage) according to what the market will support for the intended imaging application.

Figure 2:
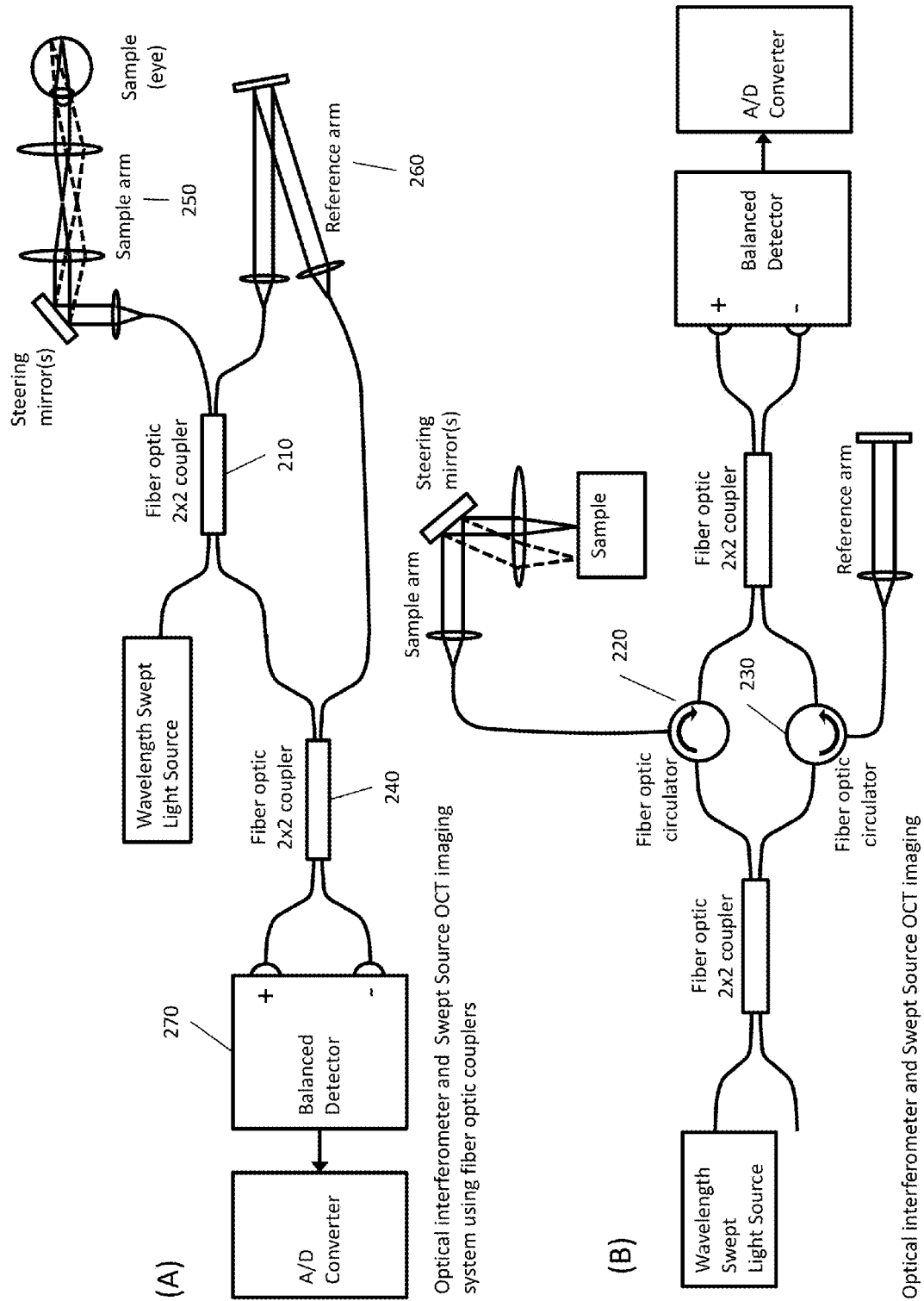
FIG. 2 is a set of drawings illustrating Swept Source OCT system layouts.

For a given maximum acquisition bandwidth and A/D conversion rate, tradeoffs must be made in the OCT system design between instrument imaging range, sweep repetition rate (with associated OCT instrument sensitivity), and axial resolution. A further consideration affecting the OCT axial point spread function and resolution is the shape of the fringe envelope. A fringe with wide spectral envelope (FIG. 4D-1) generates an OCT axial point spread function with fine axial resolution, but large sidelobes (FIG. 4E-1). The sidelobes create ghost images in the OCT data. For the same total sweep range, shaping the spectral envelope to more approximate a Guassian profile (FIG. 4D-2) reduces the sidelobes, but slightly compromises OCT axial resolution. Shaping the spectral envelope further (FIG. 4D-3) produces improved sidelobe performance, but at a cost of OCT axial resolution (FIG. 4E-3). A comparison of OCT axial point spread functions for cases 1-3 is shown in FIG. 4F. Typically, Swept Source OCT systems are designed for a single operating mode that is optimized for a specific application while considering acquisition bandwidth limitations and associated tradeoffs in imaging performance. The design of the OCT instrument is further complicated and constrained by limitations in the swept source technology itself, including bounds in operational speed and sweep bandwidth, which are significantly limited in many swept source laser technologies. In many OCT imaging systems developed to date, the short coherence length of the swept source technology is also a significant consideration which fundamentally precludes long OCT imaging range when using previous swept source technologies. The preferred embodiment of the present invention addresses these design considerations affecting OCT imaging capability and performance and overcomes many of the shortcomings of previous technologies.

Agile Imaging System

The preferred embodiment uses SS-OCT detection methods in an OCT imaging system and exploits the advantages of new Vertical Cavity Laser (VCL) based tunable source technology. The VCL tunable source technology achieves a combination of ultrahigh sweep speeds, wide spectral tuning range, adjustability in sweep trajectory and extremely long coherence length, which cannot be simultaneously achieved with any other previously demonstrated OCT light source technology.

Figure 5:
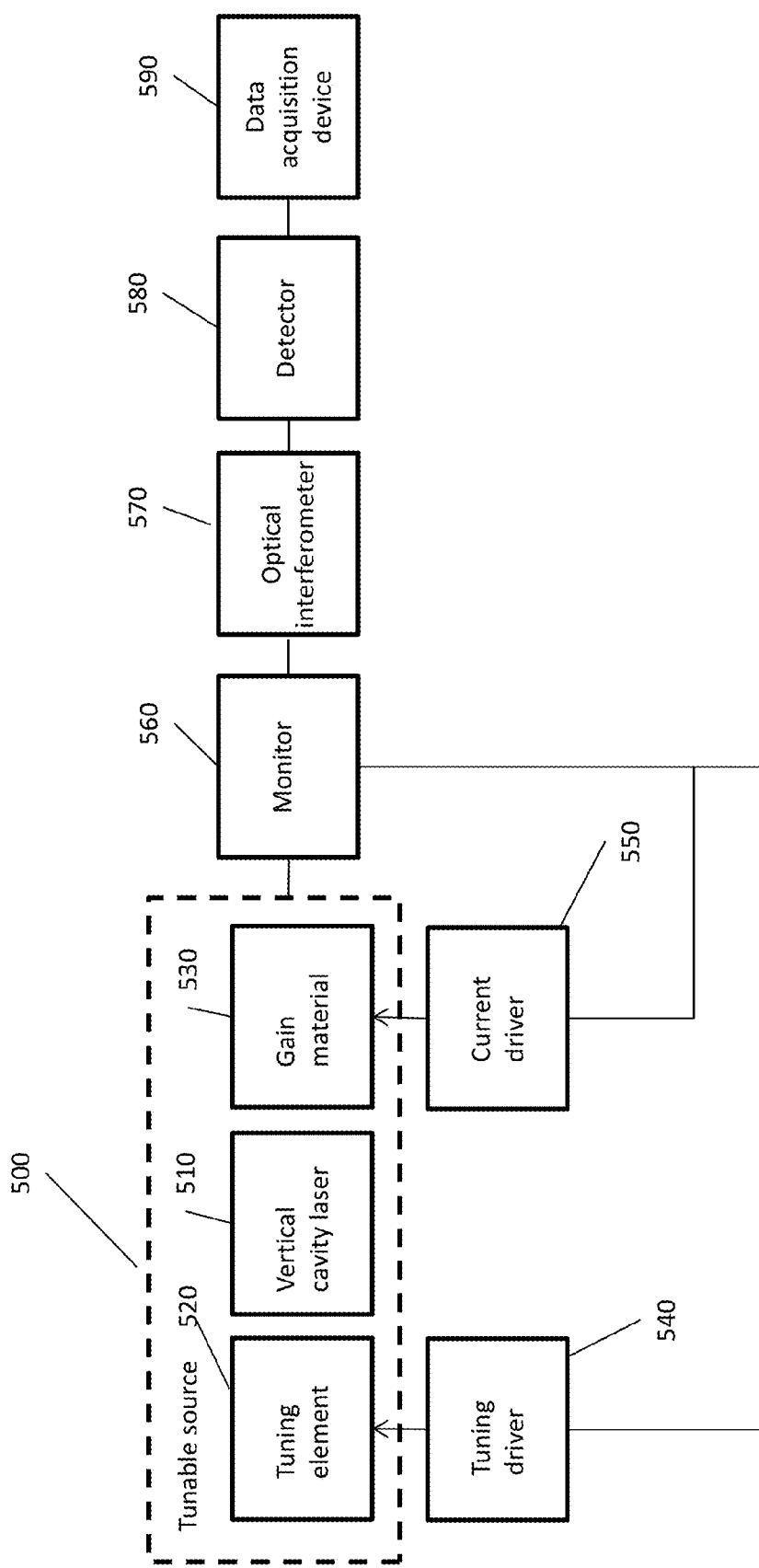
FIG. 5 is a block diagram of an imaging system.

For the purposes of introducing an embodiment of the invention, FIG. 5 provides an overview of the Agile Imaging System. In the preferred embodiment of the present invention, a light source in the OCT imaging system comprises a tunable source 500 comprising a wavelength tunable VCL source 510 and intracavity tuning element 520 generating a single longitudinal mode output that is tunable over an emission wavelength range for generating wavelength sweeps. The single longitudinal mode output emission allows the coherence length of the VCL source 510 to be significantly longer than other tunable sources of previous OCT technologies. The long coherence length of the source enables the extended imaging range of an embodiment of the present invention. The wavelength or frequency of the light emission is determined by the intracavity tuning element. The preferred embodiment of the present invention also comprises a tuning driver 540, the tuning driver being capable of generating one or more wavelength tuning waveforms to affect the tuning element 520 in the laser which determines the sweep trajectory, sweep speed, sweep repetition rate, sweep linearity, and emission wavelength range. An input signal to the tuning element 520 provided by the tuning driver 540 affects the tuning of the tuning element 520. Different input signals applied to the tuning element 520 generate different wavelength tuning responses as a function of time. The dynamics of the tuning mechanism define an input-output relationship for the tuning element. The output wavelength tuning will be a function of time and follow a sweep trajectory that is often repeated. This trajectory will have associated sweep speed, sweep repetition rate, sweep linearity, and emission wavelength range. By using different drive waveforms applied to the tuning element through a tuning driver, different tuning responses can be realized. The tuning response is the wavelength of emission as a function of time. The preferred embodiment comprises at least one current driver 550 that supplies current to a gain material 530 within the tunable source to adjust output optical radiation power. The gain material 530 may be internal to the VCL 510, for example in the case of an electrically pumped VCL. The gain material 530 may be external to the VCL 510, for example in the case of an optical amplifier. The gain material 530 may be external to the VCL 510, for example in a pump laser, as is the case when using an optically pumped VCL. For illustrative purposes, the gain material 510 is shown as a component in the block diagram, although the actual design and fabrication of the tunable source 500 define the relative geometry and precise location of the gain material. In cases where it is desirable to shape the gain or output spectrum, the current to the gain material can be changed as a function of time. The preferred embodiment of the present invention comprises a monitoring detector (monitor) 560 to measure attributes of the tuning response and provide feedback to correct for disturbances to the tunable source or to generate tuning waveforms to support multiple modes of OCT imaging. In FIG. 5, the line connecting the monitor 560 to the tuning driver 540 and current driver 550 represents feedback of information. The details of the feedback mechanisms and embodiments for using the information are described later. The preferred embodiment also comprises an optical interferometer 570 with reference arm and sample arm illuminated by the tunable source, one or more optical detectors 580 that convert the optical interference fringe signals from the optical interferometer into electric analog signals, and a data acquisition device 590 to convert the electric analog signals output from the one or more detectors into digital data. The embodiment of the present invention applies to all forms of OCT that use a wavelength swept tunable source.

Tunable Source

Figure 6:
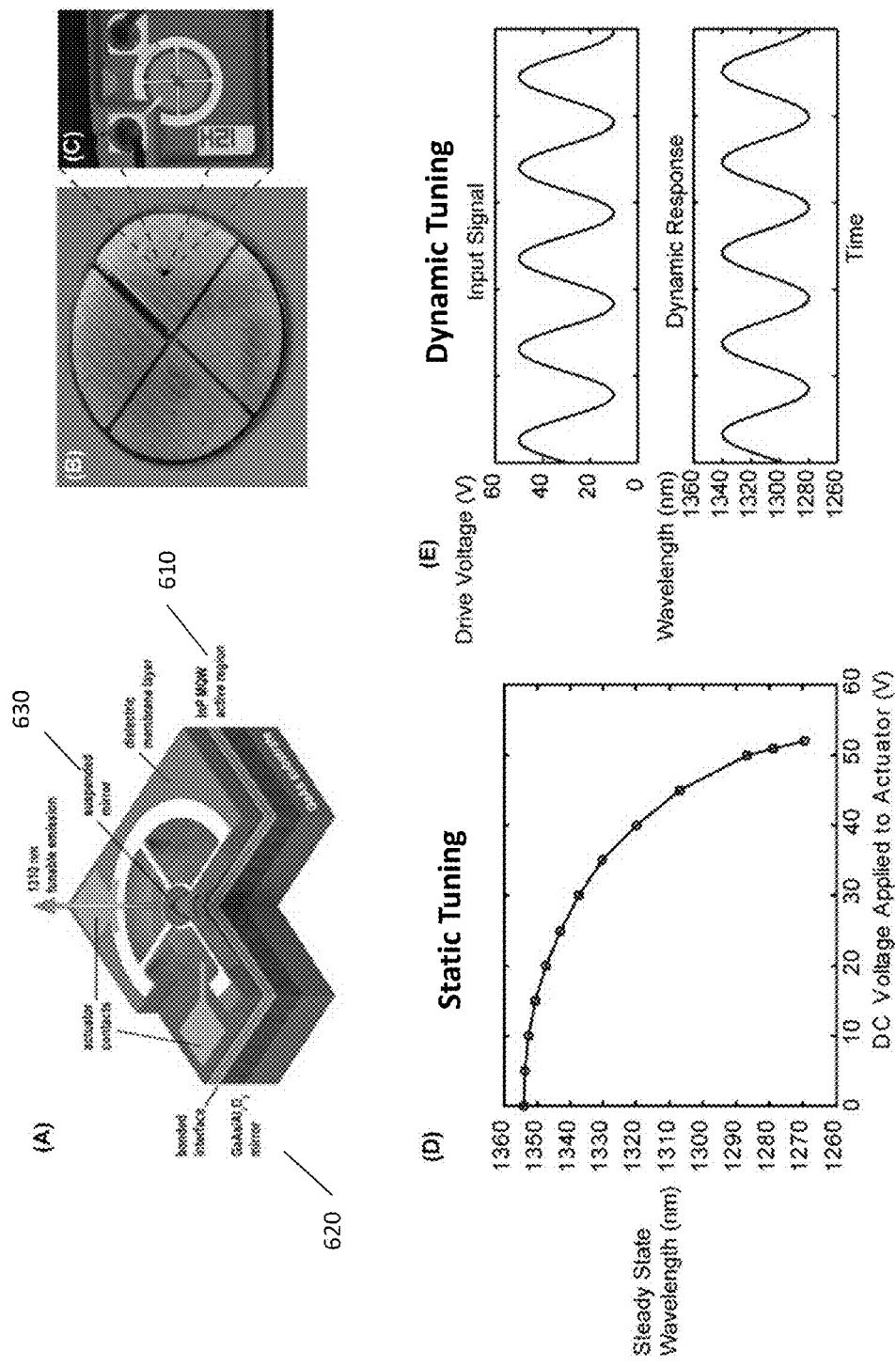
FIG. 6 is set of drawings, photographs, and plots illustrating a MEMS-tunable Vertical Cavity Surface Emitting Laser (MEMS-VCSEL).

The tunable source generates light that is directed to the input of the monitoring detector and OCT interferometer. In the preferred embodiment, the tunable source comprises a VCL. In one preferred embodiment, the VCL is a Vertical-Cavity Surface-Emitting Laser (VCSEL), or alternately called MEMS-tunable VCSEL, as illustrated in FIG. 6A. The VCSEL is manufactured using wafer fabrication techniques, as shown in FIG. 6B. A magnified image shows a single VCSEL device from the wafer in FIG. 6C. The gain material 610 in this preferred embodiment is optically pumped with light from an external pump laser of suitable wavelength for stimulating the gain material. The VCSEL laser cavity is formed by locating the gain material between two mirrors. A bottom mirror is stationary 620. A top mirror 630 acts as the output coupler and is suspended by a flexible structure. The mirrors form a Fabry-Perot filter such that the wavelength of tuned emission is proportional to the separation distance of the mirrors. Applying voltage across actuator contact pads creates an electrostatic attractive force at the MEMS actuator which pulls the top mirror down, thereby reducing the cavity length and tuning a shorter wavelength of emission. FIG. 6D shows static wavelength tuning of a VCSEL device obtained by applying a DC voltage across the actuator. The attractive force, $F_a$, is nonlinear in voltage, V, and deflection, $\delta$, where g is the undeflected actuator gap distance, $\in$ is the permittivity, and A is the area, as shown in Eq. 3.

$$F_a = \frac{V^2 \varepsilon A}{(g-\delta)^2} \qquad \text{Eq. 3}$$

The restoring force of the actuator, $F_s$, is generally linearly proportional to deflection, following the equation for a spring, $F=k_s\delta$, where $k_s$ is the spring constant of the actuator. At a particular critical DC voltage and corresponding deflection, the electrostatic attractive force exceeds the restoring force of the MEMS flexible structure and the actuator becomes unstable. A rapid acceleration of the actuator causes the top half of the actuator to collide with the bottom part of the actuator, an event referred to as "pull-in" or "snap-down" in the MEMS electrostatic actuator community. For many MEMS actuator geometries, snap-down occurs at a deflection approximately one third of the total gap distance for static tuning. For the device characterized in FIG. 6D, snapdown would occur when the deflection vs. voltage curve becomes vertical, which would be slightly above 52 volts. The DC snapdown voltage and static tuning response curve are specific to different MEMS actuator designs and depend on the material selection and geometry. The deflection during dynamic tuning of the MEMS device can exceed the static snap-down deflection because the voltage can be reduced at higher deflections and the dynamics of the MEMS actuator used to carry the actuator through the snap-down position using the momentum of the actuator. A wavelength sweep suitable for OCT imaging can be obtained by applying a time varying voltage waveform to the actuator, as illustrated in FIG. 6E. In general, the VCL will generate wavelength sweeps at a sweep repetition rate. Faster sweep repetition rates allow faster imaging speeds. Details of preferred tuning waveforms and methods for their synthesis will be described later in this document.

Figure 7:
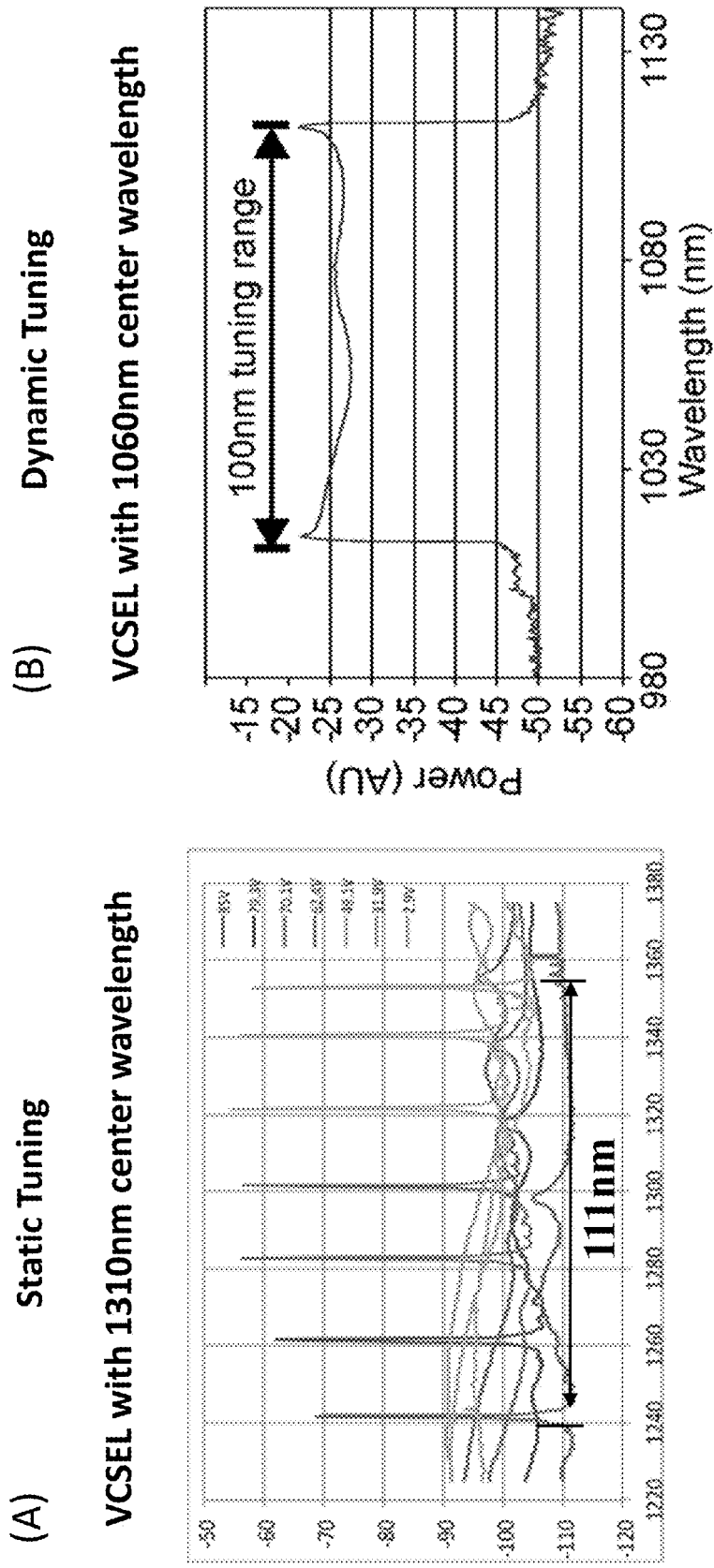
FIG. 7 is a set of plots illustrating wavelength sweep ranges of MEMS-tunable VCSELs.

FIG. 7A shows static wavelength tuning of a VCSEL centered around 1310 nm and FIG. 7B shows dynamic tuning of a VCSEL centered around 1060 nm. Different applications of OCT require different wavelengths for optimal performance. It is known that longer wavelengths exhibit less scattering in tissue and other materials than shorter wavelengths. Scattering is not the only consideration when choosing the appropriate wavelength for OCT imaging. Water absorption can attenuate the light signal in the sample and regulatory safety standards limit the maximum exposure allowed on the sample for in vivo imaging. The water absorption windows around 850 nm and 1065 nm are often selected for OCT imaging of the human retina where the light beam must traverse a round trip through approximately 20-25 mm of water in the vitreous. Wavelengths longer than around 1100 nm are not commonly used for retinal imaging because the water absorbs too much light power. Traditionally, wavelengths shorter than 750 nm have been rarely used for ophthalmic OCT imaging because ANSI standards limit the light exposure allowed on the eye to small power levels at these wavelengths, light is highly scattered at these wavelengths, and the OCT beam is visible to the patient such that the patient often tracks the beam as he or she is being scanned, introducing motion artifacts into the image data. Nevertheless, visible wavelength OCT has been performed and is of interest for medical diagnostics because of the different contrast obtained at these shorter wavelengths. Thus, OCT systems operating in the visible spectrum are of interest. One preferred embodiment of the present invention uses a center wavelength of the emission wavelength range between 380 nm and 750 nm. Infrared light beyond the visible is particularly useful for OCT imaging because of reduced scattering at longer wavelengths. Infrared light is also less visible or not visible to the patient, so the patient is less likely to unintentionally follow or track an infrared beam projected on the eye or retina. Because water absorption starts to increase around 900 nm and peaks around 970 nm, the low absorbing windows of infrared light approaching this absorption peak is particularly useful for OCT imaging. One preferred embodiment of the present invention operates with the center wavelength of the emission wavelength range between 750 nm and 970 nm. Nearly all commercial retinal OCT imaging instruments operated with wavelengths in the 800 nm range. A second water absorption window exists around 1065 nm. OCT imaging at 1065 nm has been demonstrated to achieve increased penetration into the choroid and optic nerve head of the retina and be less susceptible to cataracts when imaging older patients. Regulatory standards allow larger power into the eye at 1065 nm wavelengths than at 800 nm wavelengths. When imaging skin samples and retinal samples, different contrast has been observed between 1065 nm and 800 nm wavelengths. An OCT imaging system using wavelengths centered around 1065 nm and spanning the width of the water absorption window is useful for OCT imaging. One preferred embodiment of the present invention operates with the center wavelength of the emission wavelength range between 970 nm and 1100 nm. OCT imaging of skin and other scattering tissue and material samples is commonly performed using 1310 nm wavelengths. OCT has also been performed at 1550 nm wavelengths. One preferred embodiment of the present invention operates with the center wavelength of the emission wavelength range between 1200 nm and 1600 nm. Recent research results have indicated that OCT at longer wavelengths is of interest for OCT. One preferred embodiment of the present invention operates with the center wavelength of the emission wavelength range between 1800 nm and 2100 nm. As the wavelength increases, a larger wavelength sweep is required to achieve comparable OCT axial resolution. Thus, shorter wavelengths are often used and preferred for fine resolution OCT imaging and longer wavelengths are often used and preferred for deep penetration OCT imaging through scattering tissue and materials. VCLs can be designed to operate at all of these wavelengths.

Figure 8:
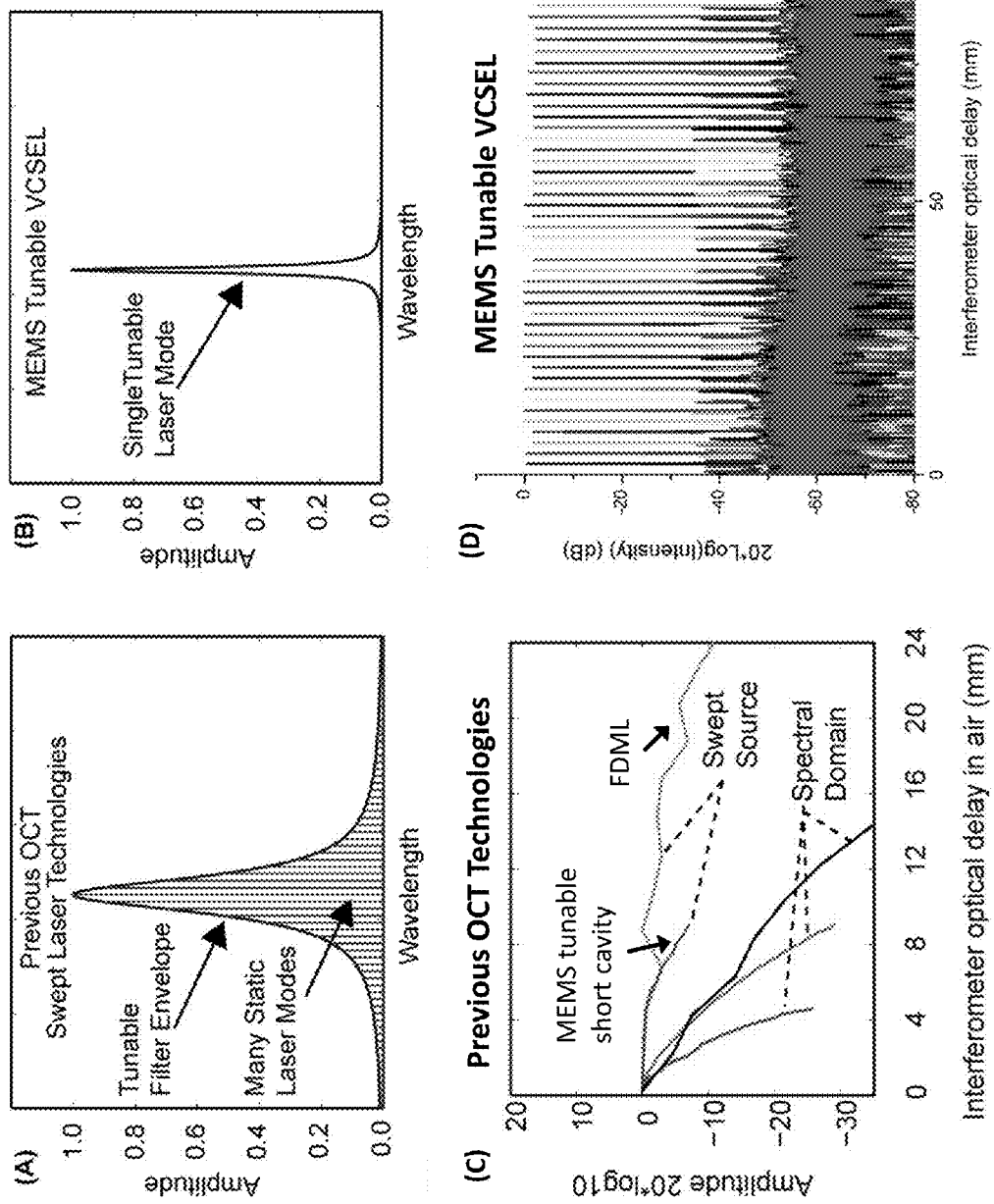
FIG. 8 is a set of drawings and plots illustrating multimode and single mode tuning principles and coherence length of OCT imaging technologies.

One significant advantage of the tunable VCL technology in the preferred embodiment is a long coherence length. The long coherence length of the source enables the generation of clean interferometric fringe cycles at long optical path length delays, much longer than previous technologies. FIG. 8A illustrates tuning of previous light sources technologies demonstrated for Swept Source OCT. The relatively long centimeter to meter cavity length of previous technologies generates multiple longitudinal laser modes within the cavity. A tuning mechanism, consisting of either an intracavity filter or a tunable wavelength selective end mirror, filters out a cluster of the longitudinal tuning modes to form the laser output emission, as illustrated in FIG. 8A. The VCL used in the preferred embodiment operates in a different regime in which a few-microns-long Fabry-Perot cavity comprises the entire laser cavity, pushing the free spectral range (FSR) beyond the tuning range of the laser and enabling mode-hop-free single mode tuning over the entire FSR, as illustrated in FIG. 8B. FIG. 8C shows the OCT sensitivity loss vs. single pass interferometer delay for previous OCT technologies using Spectral Domain and Swept Source OCT. Notice that there is a drop of at least 10 dB for the Swept Source technology at 24 mm (FDML) and 10 mm (MEMS tunable short cavity laser), and much more than 20 dB drop for the Spectral Domain OCT over only 4-12 mm of optical path delay. In significant contrast, FIG. 8D shows the OCT sensitivity drop of the VCSEL used in the preferred embodiment to drop less than 2 dB over 100 mm of interferometer optical delay, at least an order of magnitude better performance than any previous OCT imaging technology. The long coherence length of the VCL enables the long imaging image of an embodiment of the present invention. The long coherence length also simplifies fringe calibration and optical clocking, which will be described later in this document.

Figure 9:
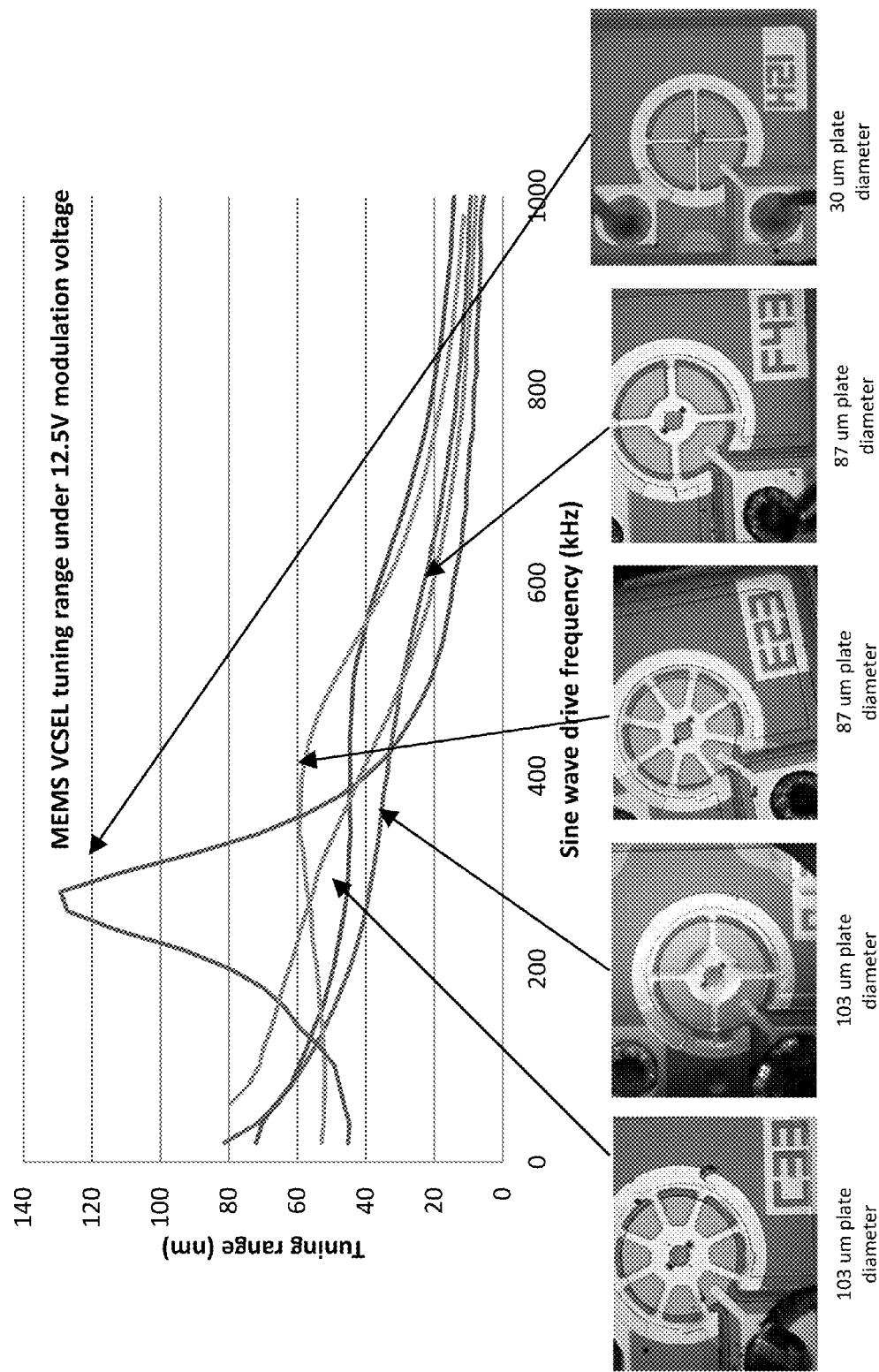
FIG. 9 is a set of plots and photographs illustrating the effect of MEMS actuator geometry on the dynamic response of the MEMS actuator.

In the preferred embodiment of the current invention, the VCL laser operates over a wide range of imaging speeds and is capable of generating wavelength tuning profiles that are preferential for OCT imaging. The design of the actuator in the VCL is important for achieving a wide range of tuning profiles, sweep repetition rates, and wavelength sweep ranges. FIG. 9 illustrates the effect of varying the actuator geometry in a VCSEL on the frequency response of the tuning mechanism. For a small plate diameter of approximately 30 μm, the device shows a lightly damped (high Q factor) resonant peak around 290 kHz. This device has a strong preference for operating near 290 kHz with a sine wave sweep trajectory and has a dynamic response consistent with a second order spring-mass-damper system, $M\ddot{x}+B\dot{x}(t)+k_s x(t)=F(t)$, where M is the lumped mass of the actuator, B is the lumped viscous damping, $k_s$ is the lumped spring constant, and $F(t)$ the force as a function of time, t. Increasing the plate diameter increases the damping coefficient, B, but it also starts to add squeeze film damping effects. The dynamic real stable pole and real stable zero associated with squeeze film damping become apparent in the dynamic response. Consequently, the strong resonant peak observed in the VCSEL with 30 μm plate diameter is greatly broadened, as seen in the frequency response curves for the 87 μm and 103 μm designs. At the same time, the larger 87 μm and 103 μm designs have a higher resonant frequency of approximately 400 kHz-500 kHz because of actuator stiffening associated with shorter flexure arms. The higher resonant frequency and broader resonant peak (lower Q factor) of the larger actuator plate devices makes them preferable for use over a wide range of scan repetition rates and for shaping the sweep trajectory for multi-operating mode capability. One preferred embodiment of the present invention uses an actuator design with a wide resonant peak with low Q factor and high natural resonant frequency. The wide range of sweep repetition rates and sweep ranges obtainable with the VCL source enable multiscale imaging capability for measurement over orders of magnitude dimensional scales using a single device. For applications where a very long imaging range is required, the mass of the actuator can be made large and the stiffness small to achieve a stable sweep at low repetition rates of several kHz. One preferred embodiment of the present invention uses a large mass actuator and low stiffness to achieve stable sweeping performance at <20 kHz sweep repetition rate.

Figure 10:
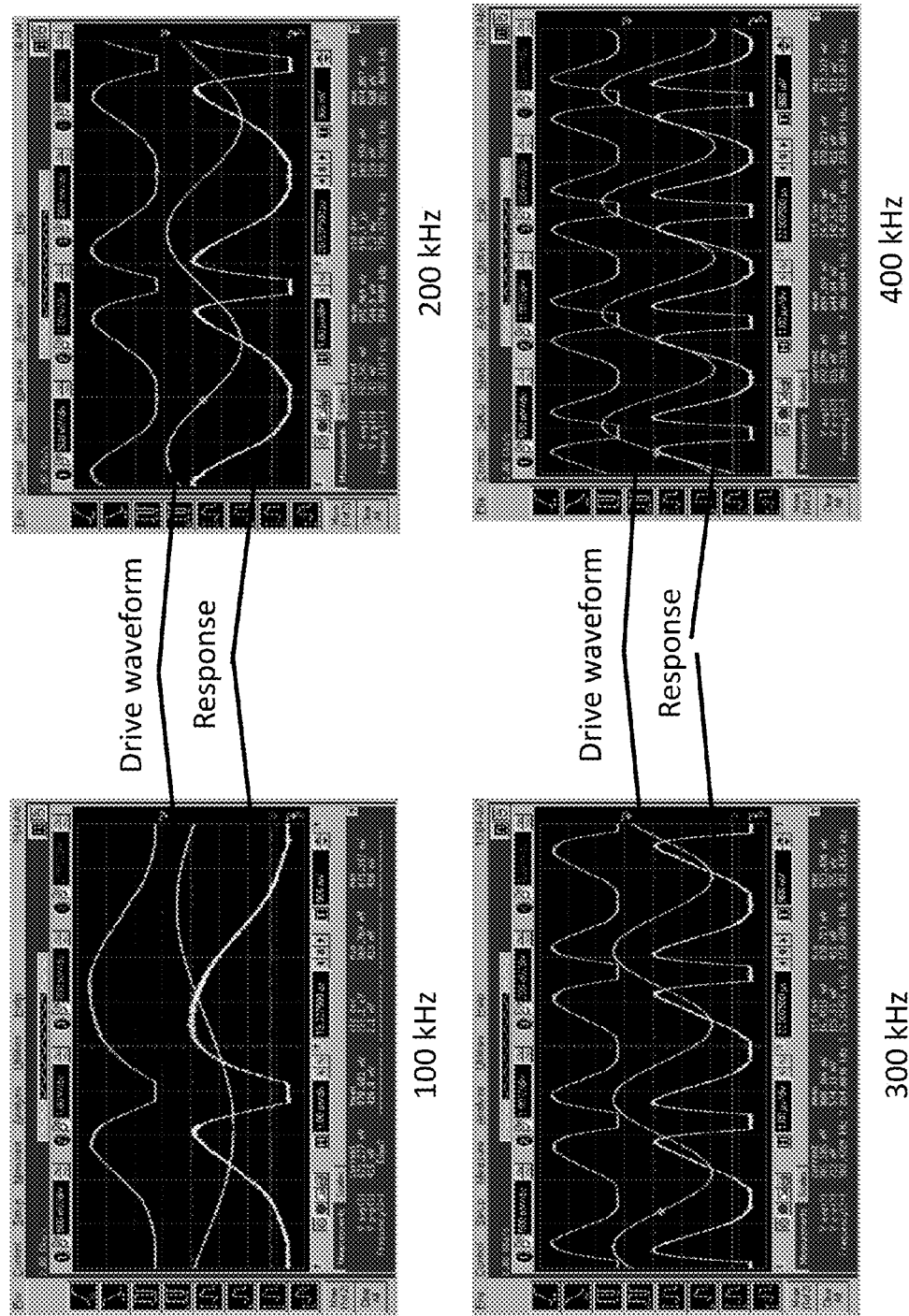
FIG. 10 is a collection of oscilloscope screen images showing a single tunable source being driven at different sweep repetition rates from 100 kHz to 400 kHz.
Figure 11:
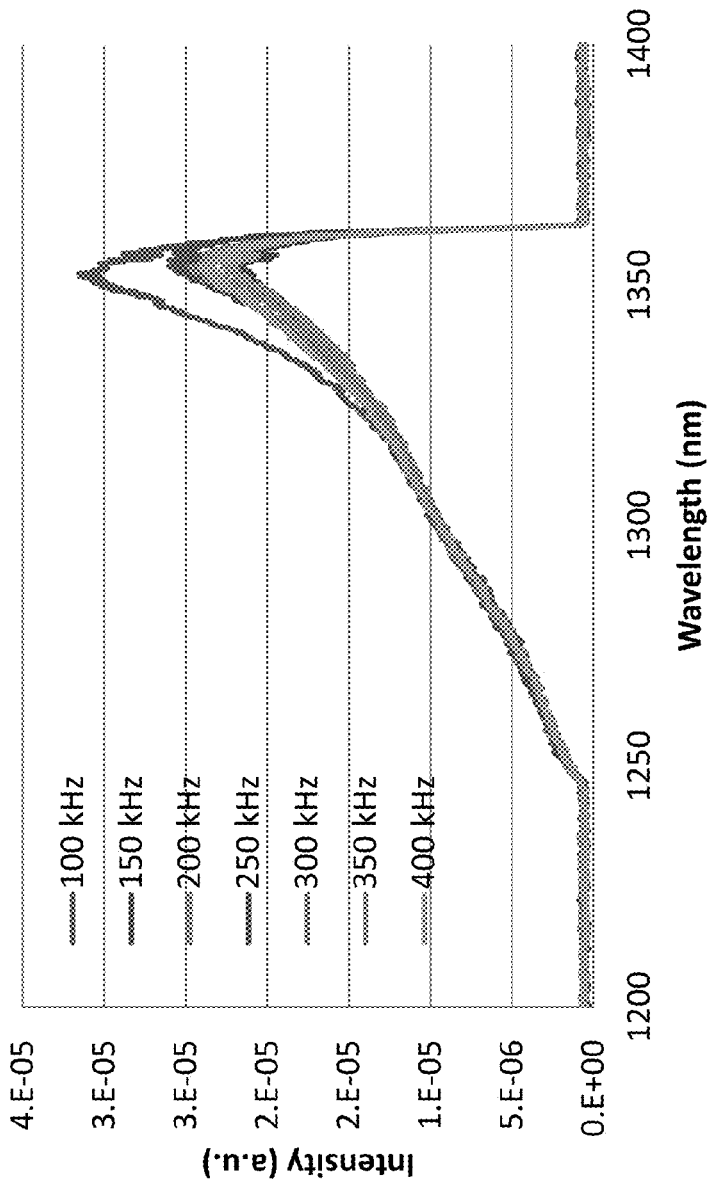
FIG. 11 a plot showing the spectral response of a single tunable source being driven at different sweep repetition rates from 100 kHz to 400 kHz.

Experimental data showing a single VCSEL device being operated over a range of sweep repetition frequencies from 100 kHz to 400 kHz is shown in FIG. 10. The input drive waveform is a sine wave drive waveform as indicated in the figure. The laser cavity intensity shows the sweep trajectory, also indicated in the figure. The corresponding spectra from the 100 kHz to 400 kHz operating points are shown in FIG. 11. The spectra are almost identical with a slight variation originating from the different sweep profiles spending different amounts of time near the long wavelengths, indicating the ability of a single VCSEL to operate over a wide range of sweep repetition rates, an important characteristic of the swept light source used in the preferred embodiment to achieve variable operating speed.

Figure 12:
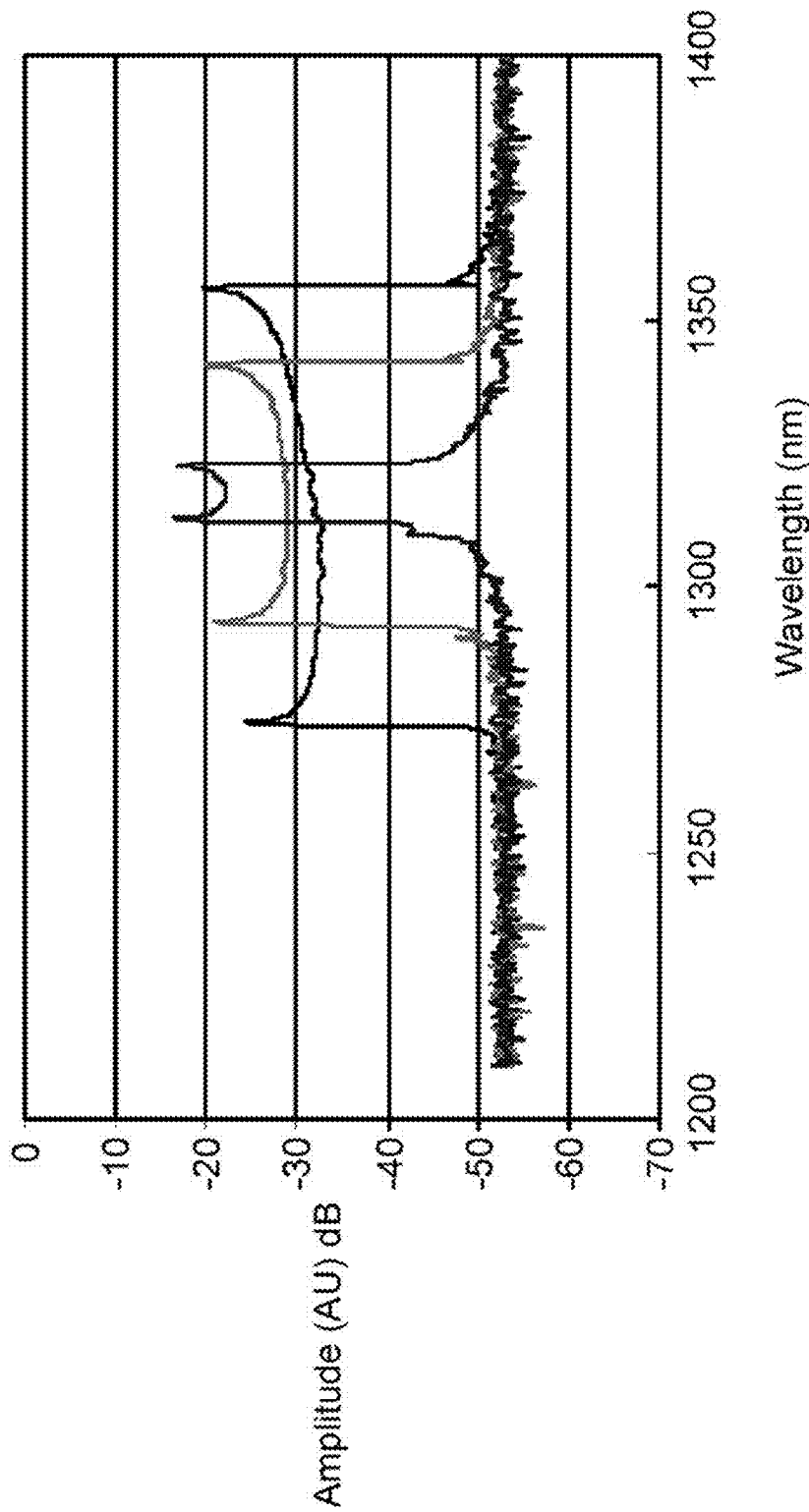
FIG. 12 is a plot showing variable wavelength range tuning of a single tunable source.

Experimental data showing a single VCSEL device being operated over different sweep ranges is shown in FIG. 12. The spectra show even power distribution over many different sweep ranges, indicating the ability of a single VCSEL to operate over a wide range of sweep ranges, an important characteristic of the swept light source used in the preferred embodiment to achieve variable sweep range and resolution imaging.

Figure 13:
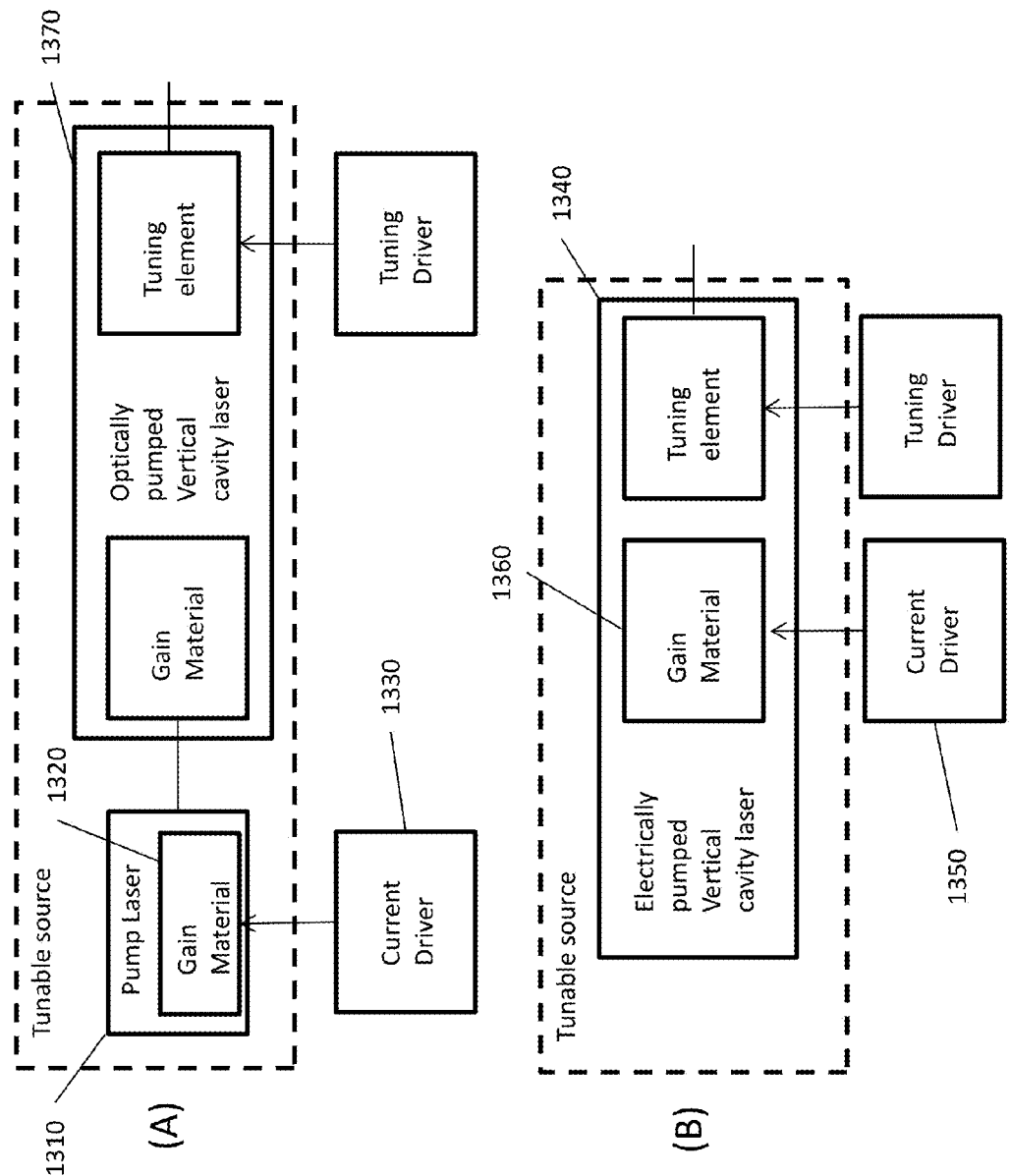
FIG. 13 is a set of block diagrams illustrating embodiments of the tunable source of the present invention.

The tunable source of the preferred embodiment contains at least one gain material inside the cavity of the laser. This gain material can be optically or electrically pumped. In the case of optical pumping, the light from a pump laser stimulates the gain material. One preferred embodiment of the present invention uses optical pumping of the gain material in the VCL. FIG. 13A shows an example of an optically pumped VCL 1370 in an Agile Imaging System. The optical pump laser 1310 itself has its own gain material 1320 that is stimulated by a current driver 1330. In the case of electrical pumping, electrical current stimulates the gain material 1360 directly. An optically pumped VCL is easier to fabricate, but requires an external pump laser and supporting optics and electronics. The choice of pump wavelength affects the spectral gain response of the gain material in the cavity. A pump wavelength of 980 nm is suitable for a VCL centered around 1310 nm and using indium phosphide gain material. A pump wavelength of 780 nm-850 nm is suitable for a VCL centered around 1065 nm and using indium gallium arsenide gain material. The design and fabrication of an electrically pumped VCL is more challenging than an optically pumped VCL, but ultimately there is a potential cost savings and size advantage achieved by eliminating the pump laser and associated optics and electronics. One preferred embodiment of the present invention uses electrical pumping of the gain material 1360 inside the VCL. FIG. 13B shows an example of an electrically pumped VCL 1340 where the gain material 1360 is electrically pumped by a current driver 1350 in an Agile Imaging System.

Figure 14:
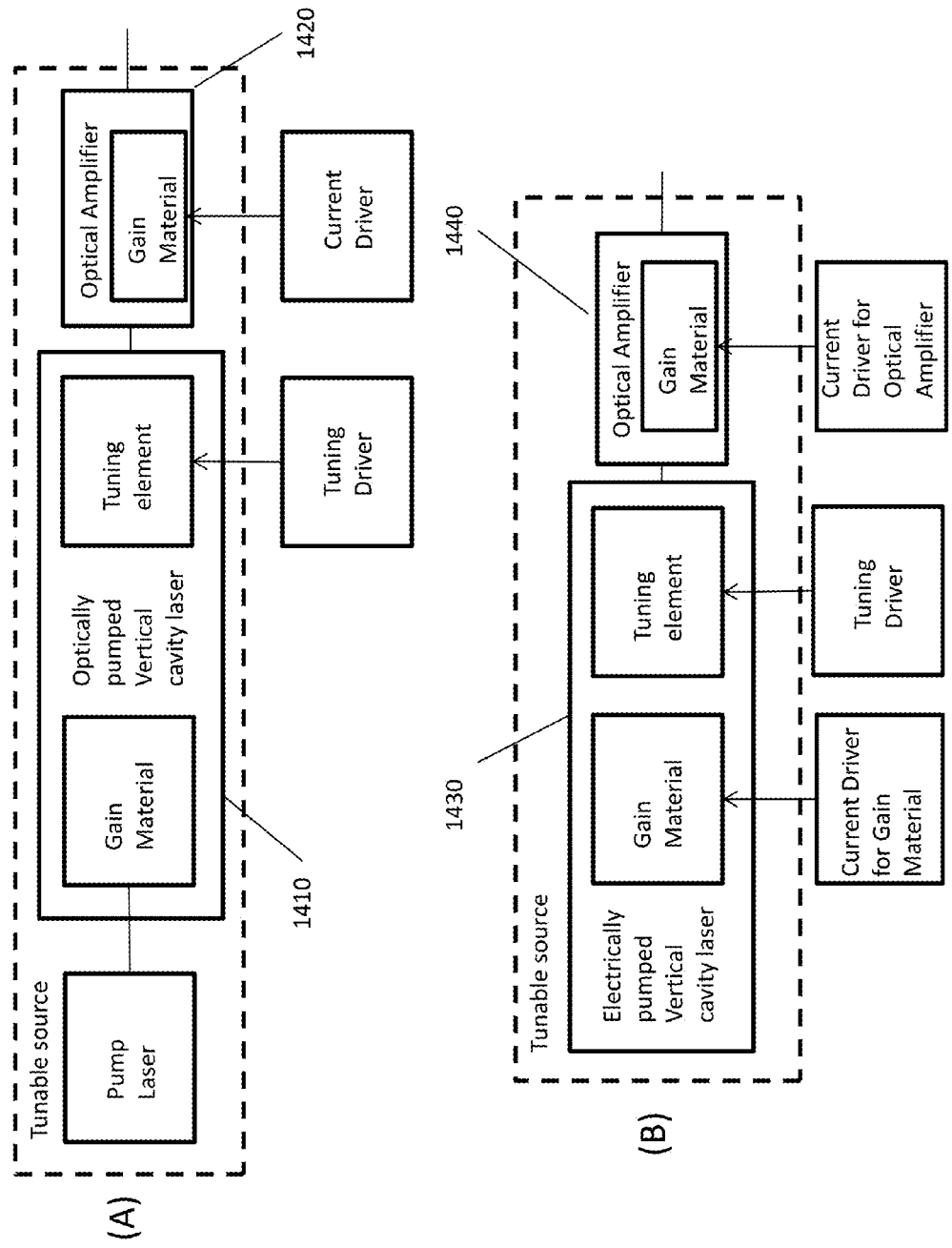
FIG. 14 is a set of block diagrams illustrating embodiments of the tunable source of the present invention comprising optical amplifiers.

The signal to noise and sensitivity of an OCT system depends on several factors, including the efficiency of the collection of light from the sample directed to the detector and the power of emission illuminating the sample. In the case when the power incident on the sample is upper bounded, high light collecting efficiency interferometer designs use a splitting ratio that directs a high percentage of light from the sample to the detector, but require higher light source power to achieve suitable power levels of sample illumination because the splitting ratio works to decrease light on the sample from the light source. The output power of the VCL alone may or may not be sufficiently high for the OCT imaging application. To increase output emission power, the tunable source in one preferred embodiment comprises one or more optical amplifiers. In one preferred embodiment, the tunable source comprises at least one optical amplifier for higher output power to increase power on the sample to achieve high OCT sensitivity. In one preferred embodiment, the tunable source comprises at least one optical amplifier for higher output power to allow high light collecting efficiency interferometer designs for improved system sensitivity performance. Examples of optical amplifiers are Booster Optical Amplifiers (BOA), Semiconductor Optical Amplifiers (SOA), Vertical Cavity Semiconductor Optical Amplifiers (VCSOA) and doped fiber, however, any optical amplifier can be used to increase the emission power output of the tunable source. In one preferred embodiment, the tunable source comprises a pump laser, optically pumped VCL, and one or more optical amplifiers. FIG. 14A shows an example system comprising an optically pumped VCL 1410 and an optical amplifier 1420. In one preferred embodiment, the tunable source can also comprise an electrically pumped VCL and one or more optical amplifiers. FIG. 14B shows an example system comprising an electrically pumped VCL 1430 and an optical amplifier 1440.

The optical amplifier amplifies the light injected into its input port. However if the gain material is not saturated, then spontaneous emission from the gain material itself will also be amplified. This amplified spontaneous emission (ASE) contribution of light counts as exposure on the sample, but does not contribute to the useful OCT fringe formation. The untuned light can therefore decrease the sensitivity of the instrument when regulatory exposure limits on the sample apply. This untuned contribution of light can also add noise to the measurement. Therefore one preferred embodiment uses a tunable source that comprises at least one amplifier that is used in a predominately saturated operating regime.

When there is no input to the optical amplifier, it will generate light that is solely amplified spontaneous emission (ASE). This ASE can be measured, for example, by removing input to the amplifier and using an optical spectrum analyzer to measure the ASE spectrum. The ASE spectrum is often used to characterize an optical amplifier and is often shown in the data sheet for commercial amplifiers. However, the ASE spectrum does not necessarily represent the gain profile of the amplifier. For this reason, it can be beneficial that the center wavelength of ASE be shifted from the center wavelength of tuning To obtain a balanced output spectrum from a BOA, for example, it can be desirable that the center wavelength of ASE be short wavelength shifted relative to the center wavelength of the VCL. An embodiment of the present invention includes the case where the optical amplifier center wavelength of the ASE is offset from the center of the tuning wavelengths for improved gain response over the wavelengths of tuning. In one preferred embodiment, the center wavelength of ASE is short wavelength shifted relative to the center wavelength of the VCL source. Large tuning ranges require large bandwidth gain response. Large bandwidth gain response can be obtained with multi-quantum state amplifiers. One preferred embodiment uses one or more optical amplifiers that incorporate a quantum well gain region with at least two confined quantum states.

In the preferred embodiment, a current driver supplies current to a gain material within the tunable source and the current can be adjusted to change the output optical radiation power. Details of adjusting the current to a gain material and methods for synthesizing preferred waveforms are described later in this document.

Figure 15:
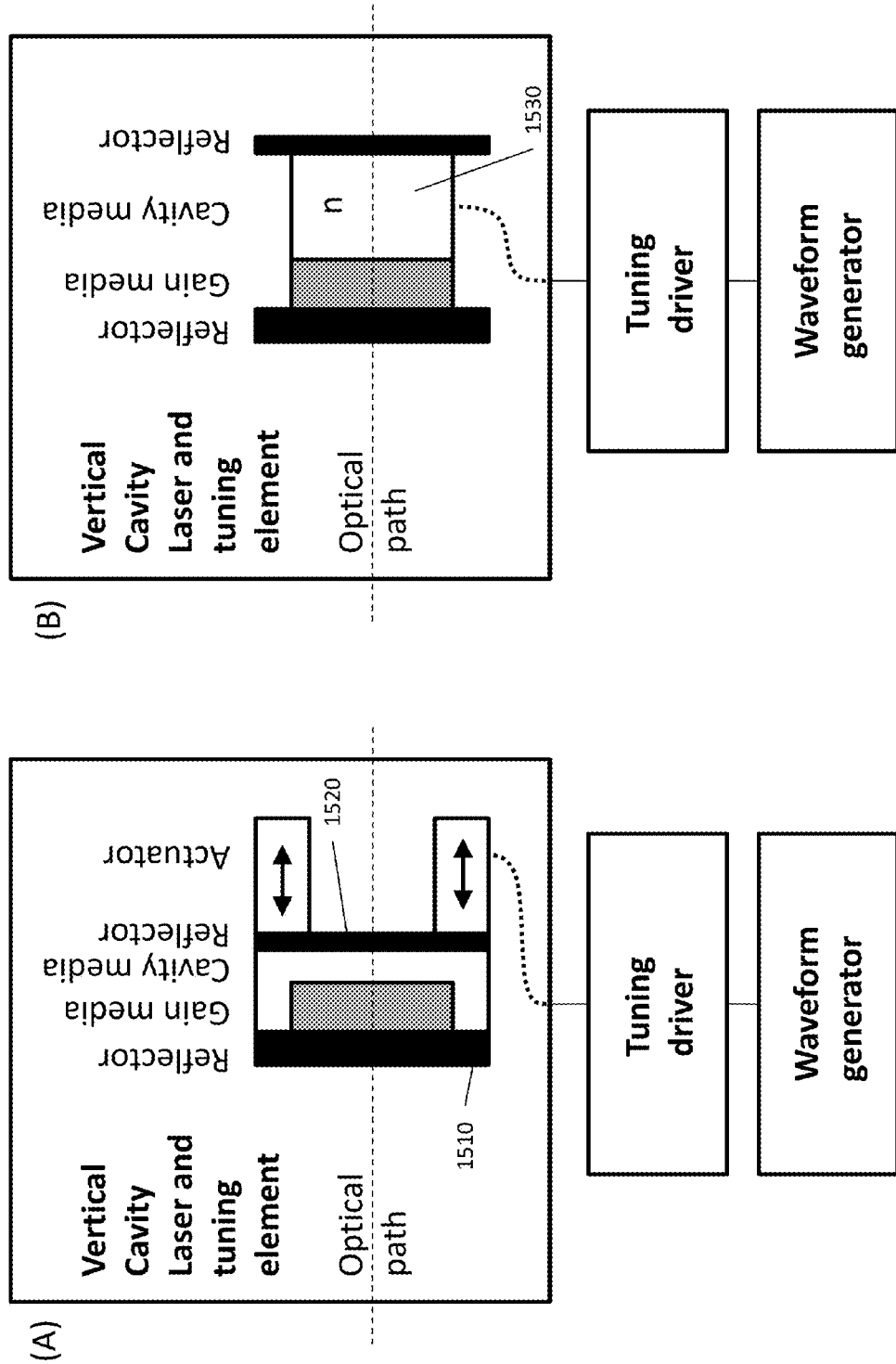
FIG. 15 is a set of block diagrams of a wavelength tuning subsystems.

The preferred embodiment of the present invention uses a VCL source that is tunable in the wavelength of output emission. As the optical path length of the optical cavity in the VCL source changes, the source tunes different wavelengths. In one preferred embodiment, optical path length is changed by changing the physical distance between the two laser mirrors defining the cavity. FIG. 15A shows an example VCL with adjustable path length achieved by changing the physical distance between two laser mirrors 1510, 1520. In another preferred embodiment, the optical path length is changed by changing the index of refraction, n, of any one or more materials between the two laser mirrors defining the optical cavity. FIG. 15B shows an example VCL with adjustable path length achieved by changing the index of refraction of any one or more materials 1530 between the two laser mirrors defining the optical cavity. There are many implementations that can achieve a change in optical path length of the optical cavity of the VCL. One preferred embodiment comprises a tuning element that is an electrostatically actuated MEMS structure or mechanism moving at least one laser mirror defining the optical cavity length of the VCL source. Another preferred embodiment comprises a tuning element that is a piezoelectric transducer actuated structure or mechanism moving at least one laser mirror defining the optical cavity length of the VCL source. Another preferred embodiment comprises a tuning element that is a transducer actuated structure or mechanism moving at least one laser mirror defining the optical cavity length of the VCL source, the transducer being capable of micron level motion. The tuning element may physically adjust the spacing between the two mirrors defining the laser cavity, as previously described, or the tuning element may change the index of refraction between the two mirrors defining the optical cavity in the laser while leaving the physical spacing between the two mirrors the same. One preferred embodiment comprises a tuning element that is a liquid crystal device capable of adjusting the optical path length of the optical cavity of the VCL source. Another preferred embodiment comprises a tuning element that is a semiconductor material capable of adjusting the optical path length of the optical cavity of the VCL source. Another preferred embodiment of the present invention comprises a tuning element that is a device or material capable of adjusting the optical path length of the optical cavity of the VCL source by a change in index of refraction. In one preferred embodiment, multiple mechanisms are combined for adjusting the optical cavity length of the laser. For example, one preferred embodiment comprises a piezoelectric transducer combined with an electrostatically actuated MEMS structure to adjust the spacing between the mirrors and could further be combined with a material that undergoes a change in index of refraction. It is understood that all combinations of devices and materials that affect the optical path length of the cavity of the laser of the VCL are incorporated under the present invention.

A significant advantage of the VCL source over previous tunable source technologies is that the micron scale cavity length of the VCL source enables very many round trips through the optical gain material to take place in a short time. Most traditional bulk optics and short cavity laser designs shown in the past have been limited in speed because of the relatively long time for ASE to build up to tuned laser emissions. Whereas longer cavity lasers are limited in their maximum sweep, the VCL source is able to achieve gain material saturation quickly to enable sweeping at much faster rates. One preferred embodiment of the present invention can operate at all speeds allowed by the dynamics of the tuning element. The fast photon dynamics of the VCL source also enable high quality bidirectional wavelength tuning One embodiment of the present invention performs OCT imaging using both directions of wavelength sweep. In certain applications, such as long range imaging or Doppler OCT, it is preferable to image with only one direction of sweep. One embodiment of the present invention performs OCT imaging using either the forwards or backwards direction of wavelength sweep. The forwards sweep is the sweep from short to long wavelength and the backwards sweep is the sweep from long to short wavelength. It is possible that the Agile Imaging System of an embodiment of the present invention be capable of imaging with both directions of wavelength sweep or one direction of wavelength sweep, possibly mixing modes during operating, the choice of operating mode being made based on the requirements of the imaging application at hand.

The design of the tunable source also affects the performance of the imaging system. The sidemode separation is determined by which mode the laser cavity is operated in. The preferred embodiment of the present invention operates the laser cavity near m=1 such that the sidemodes are separated from the primary laser line to facilitate suppression or removal of the unwanted sidemodes. In general, it is desirable to suppress the sidemodes to reduce imaging artifacts. One preferred embodiment of the present invention has a side mode suppression ratio higher than 20 dB when the laser output frequency is statically tuned by a tuning control signal. The VCL laser is able to tune a single longitudinal mode, which enables a very long coherence length. The preferred embodiment has a tunable source with a coherence length longer than 30 mm when the laser output frequency is continuously tuned by a tuning control signal. Longer coherence length is possible and desirable for many imaging applications.

Tuning Trajectories and Drive Waveform Synthesis

Figure 16:
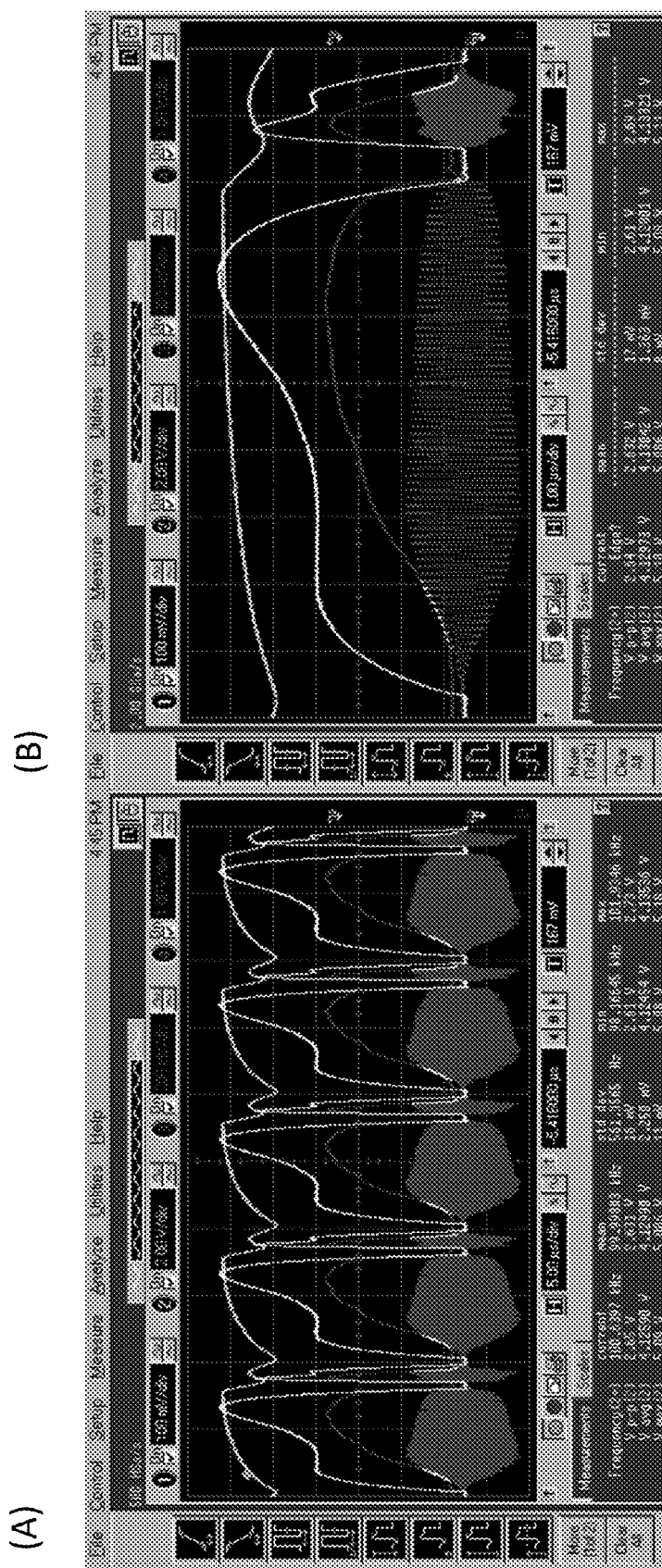
FIG. 16 is a set of oscilloscope screen images showing the tuning response of a VCSEL driven at 100 kHz with a linearized sweep driven by a custom waveform.
Figure 17:
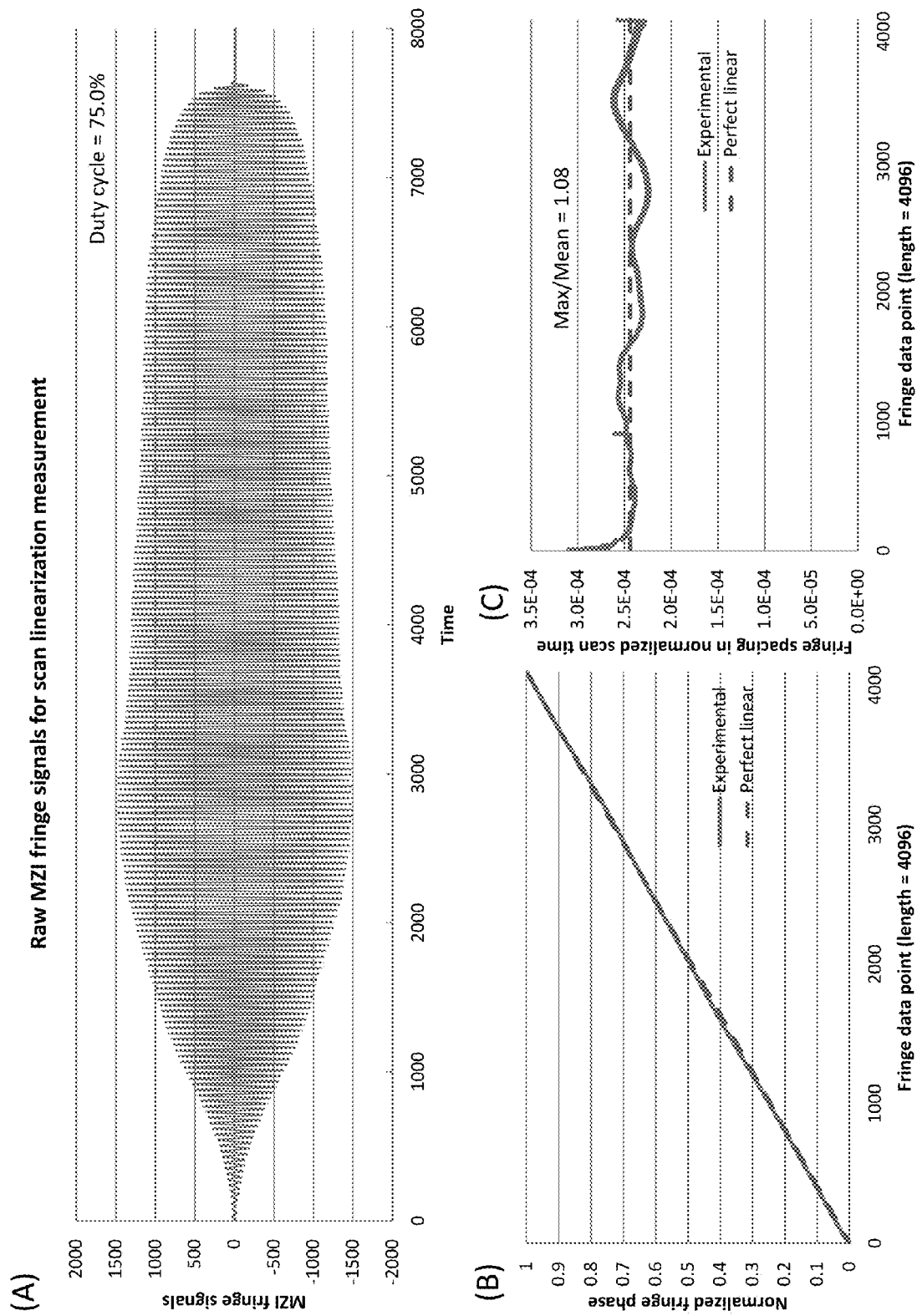
FIG. 17 is a collection of plots showing linearized sweep performance.
Figure 18:
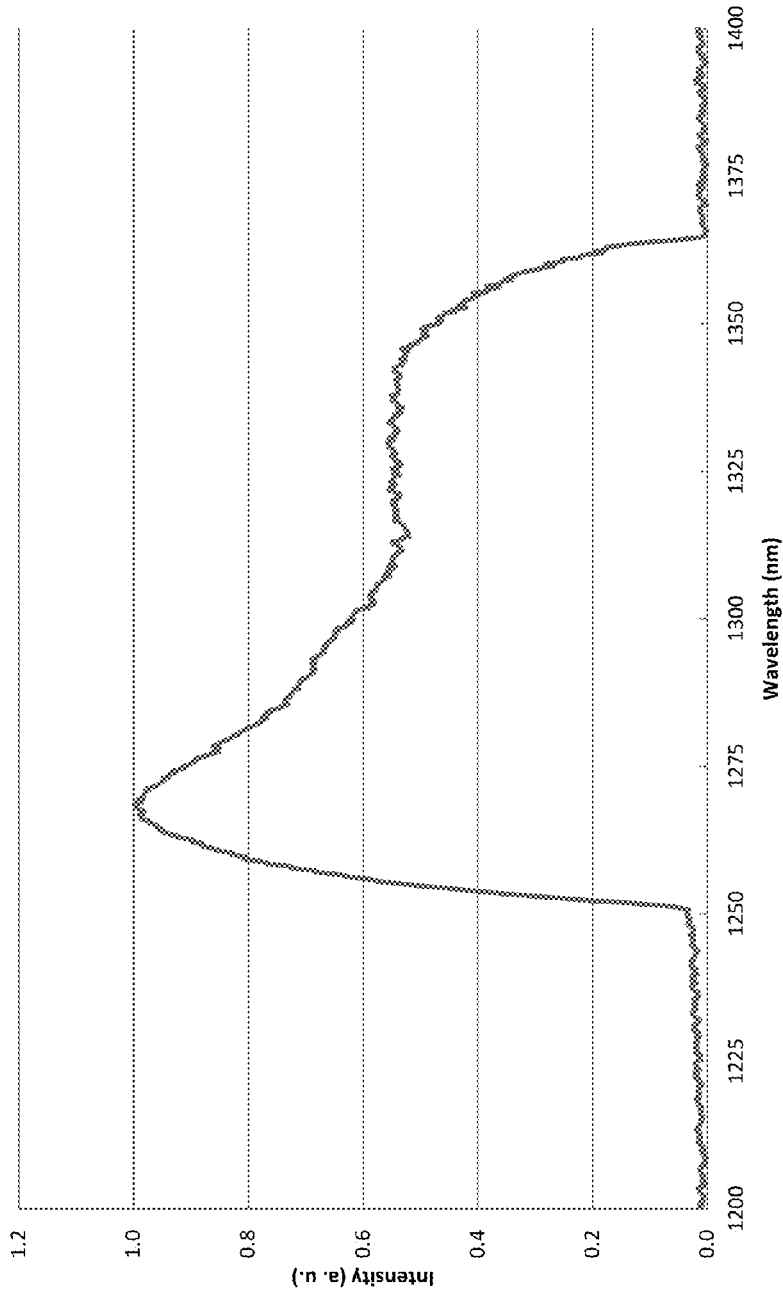
FIG. 18 is a plot showing the optical spectrum of a VCSEL driven at 100 kHz driven by a custom waveform.

The OCT imaging performance in an embodiment of the present invention can be improved if the tuning waveform alters the tuning response of the tuning element from the tuning element's natural dynamics. In Swept Source OCT, the maximal peak OCT fringe frequency defines the maximum imaging range of the instrument because of the requirements of Nyquist sampling and because of upper limits on the A/D data acquisition sampling rate and bandwidth. The preferred embodiment executes a sweep trajectory that acts to minimize peak OCT fringe frequency. Peak fringe frequency can be reduced by extending the time over which the wavelength sweep occurs. Thus, a high duty cycle of imaging sweep time to non-sweep time is beneficial for OCT. Peak fringe frequency can also be reduced by minimizing the peak wavenumber rate of change over a trajectory that connects a starting and ending wavelength, the optimal solution of which is a straight line (ramp) in wavenumber position and a constant in wavenumber velocity. The ideal sweep trajectory would be both high duty cycle and linear in k-space (wavenumber). In practice, the dynamics of the actuator place limits on the acceleration that can be obtained and there are multiple resonant modes that can be excited. Therefore, the optimal sweep trajectory that considers actuator dynamics may not be perfectly linear in order to minimize peak fringe frequency. The preferred embodiment of the present invention acts to generate sweep trajectories that minimize or reduce peak fringe frequency within actuator dynamics. It is sometimes desirable to emphasize a linear sweep and compromise the peak fringe frequency goal. For example, certain A/D converters work best at constant clock frequency when optically clocked by an OCT system. One preferred embodiment generates sweep trajectories that act to linearize the sweep at a potential cost of compromised peak fringe frequency. An experimental example of a fringe of an embodiment of the current invention is shown in FIGS. 16 and 17, which has been driven with a waveform that acts to linearize the sweep trajectory with respect to wavenumber in order to reduce peak fringe frequencies and keep the fringe frequency constant during the sweep. FIGS. 16A and 16B show the drive waveform and fringe response over multiple periods and a zoom over one period, respectively. The sweep is predominately linear in k and the duty cycle is high with a long imaging sweep and a short fly-back sweep to perform unidirectional sweep imaging. FIG. 17A shows a detailed zoom over one fringe, FIG. 17B shows the fringe phase evolution in time, FIG. 17C shows the experimental fringe spacing compared to the optimal fringe spacing, and FIG. 18 shows the corresponding amplified spectrum. In this example, the tunable source has the output frequencies linearized in time with linearization ratio better than about 1.2. This waveform improves the OCT imaging range for a given A/D converter rate over the natural sine wave response of the actuator. One preferred embodiment of the present invention uses tuning waveforms to improve sweep linearity to enable a longer OCT imaging range for a given maximum A/D sampling clock rate.

Figure 19:
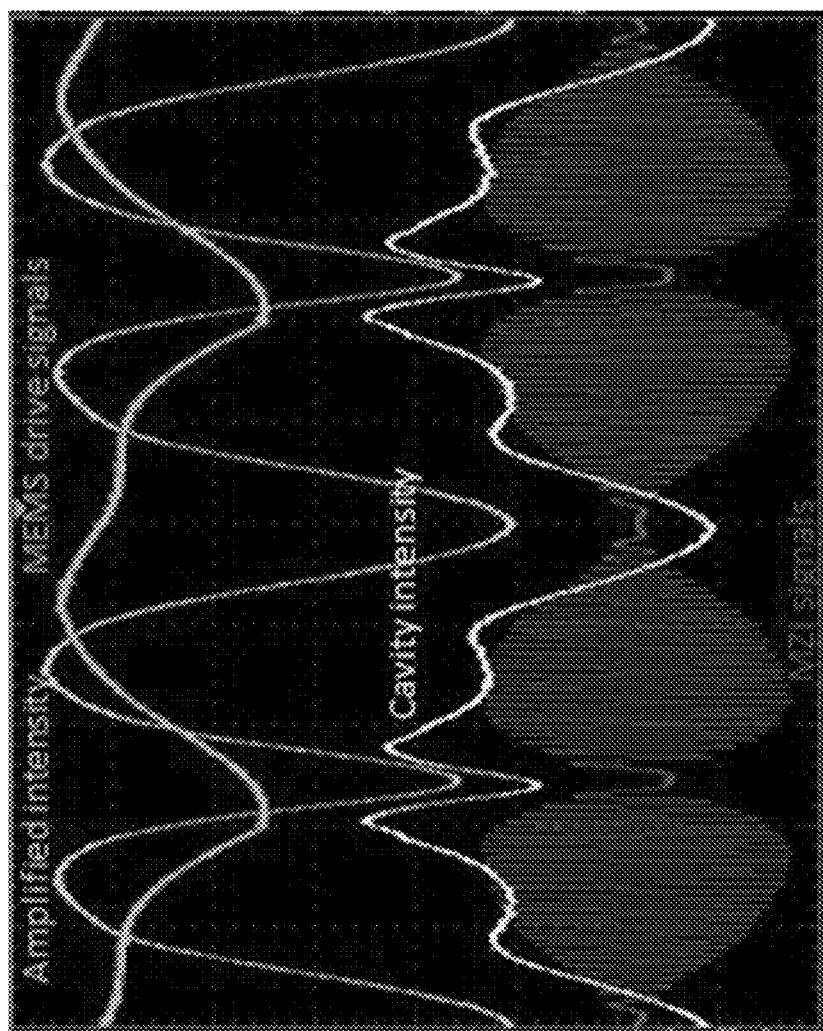
FIG. 19 is an oscilloscope screen capture showing bidirectional and linearized sweep trajectories.
Figure 20:
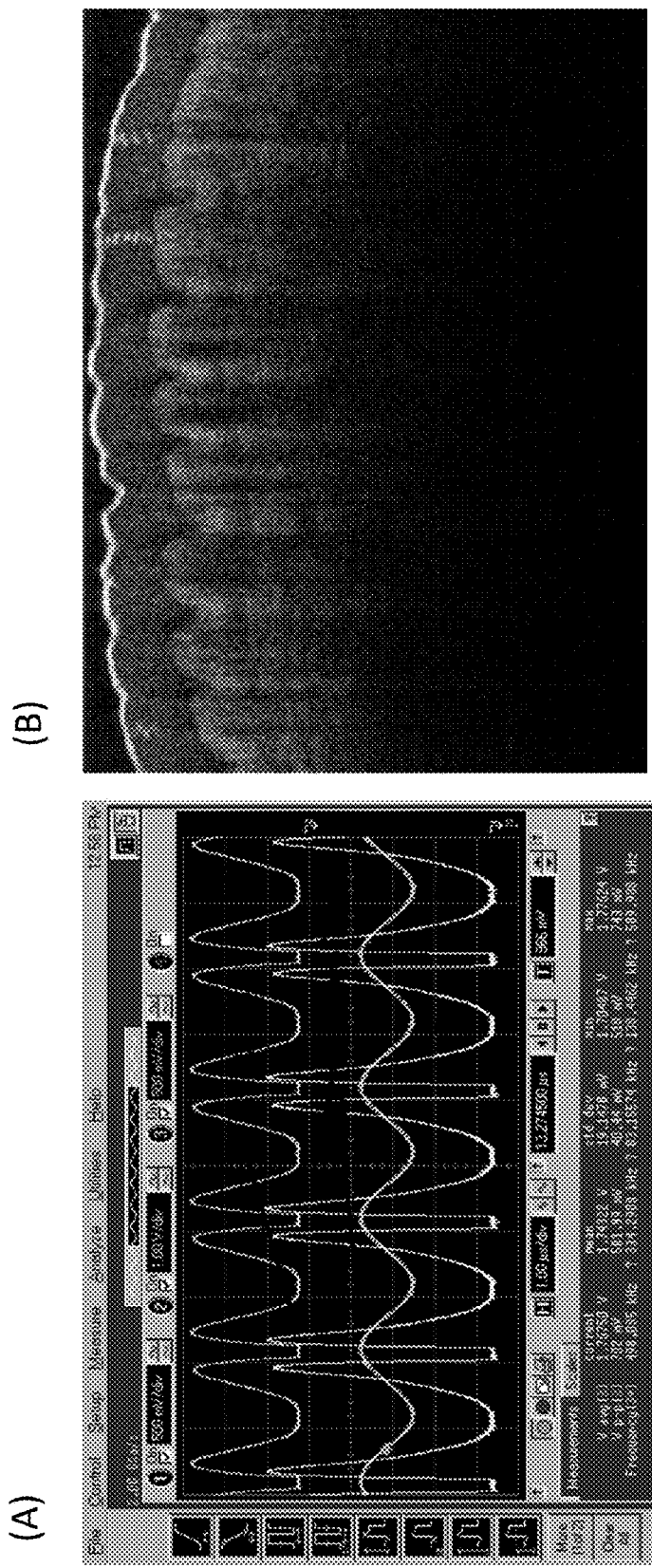
FIG. 20 is a plot and image showing the tuning response of a tunable source and the associated image of a human finger obtained at 500 kHz sweep repetition rate.
Figure 21:
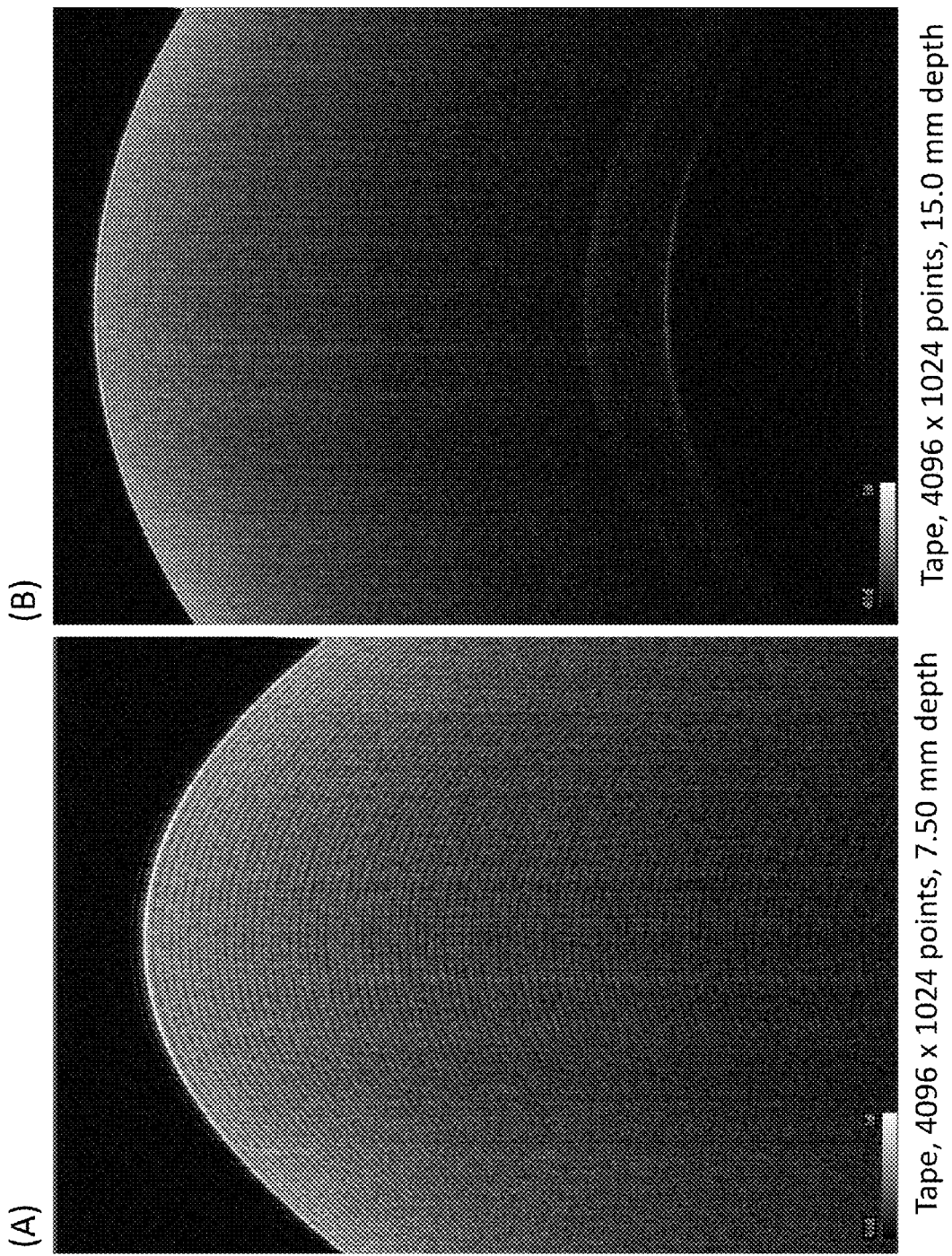
FIG. 21 is a collection of images showing imaging at two different imaging ranges.

High speed applications of OCT generally benefit from using a bidirectional sweep because the tuning element does not have to execute a complete fly-back and return to the starting wavelength, thereby improving duty cycle. FIG. 19 shows experimental OCT fringe data from a Mach-Zehnder interferometer of a linearized, high duty cycle, bidirectional sweep. One preferred embodiment of the present invention acquires data using both the forwards and backwards sweeps. Approaching the resonant frequency of the actuator, it is not always possible to linearize the sweep. FIG. 20A shows the drive waveform and sweep trajectory for a VCSEL device operated at 500 kHz, near resonance, while FIG. 20B shows the corresponding OCT image of a human finger pad acquired at 1 MHz axial scan rate using both sweep directions of this bidirectional sweep. However, long imaging range OCT applications can benefit from unidirectional scanning that reduces the rate of wavelength tuning with time for a given VCL repetition rate. FIGS. 21A and 21B show long range OCT images of a roll of tape. Certain OCT imaging modalities, such as Doppler OCT, can also benefit from a unidirectional sweep because such methods rely on a precise and fixed time difference between wavelengths that cannot be obtained using adjacent bidirectional sweeps. One preferred embodiment uses only the forwards or backwards sweep for OCT imaging. Yet another preferred embodiment of the present invention can switch between using both the forwards and backwards sweeps for bidirectional imaging and only the forwards or backwards sweep for unidirectional imaging, as required by the OCT imaging application.

In OCT, the length of the wavelength sweep, the trajectory of the wavelength sweep, and the sweep repetition rate all contribute to the peak fringe frequency, which determines the maximum imaging range for a given A/D acquisition rate. Thus there is an inherent tradeoff between sweep range (associated with OCT axial resolution), sweep repetition rate, and imaging range in Swept Source OCT imaging. There is also an inherent tradeoff between OCT system sensitivity and axial scan rate. For these reasons, it is desirable to be able to change the sweep repetition rate of the laser to accommodate and optimize for different imaging applications.

In the case of one preferred embodiment where the VCL uses an electrostatic MEMS tuning element, it is possible to change the trajectory within approximately one sweep period when the sweep repetition rate is in the 1's, 10's, or 100's of kHz range. The waveform to the drive element can be changed between acquisition of data sets, but also during a data acquisition. One embodiment of the present invention allows the acquisition of a mixture of operating modes within a single data set. For example, a volumetric 3D acquisition could repeat B-scans and alternate between long imaging range, relaxed axial resolution and short imaging range, fine resolution acquisition to obtain additional information about the sample. By trading either sweep speed or sweep range, the imaging range can be adjusted while staying within the acquisition bandwidth. Mixing imaging modes with respect to changing sweep range and sweep repetition rate together during acquisition illustrates the high degree of flexibility and agility of the present invention. However, one preferred embodiment operates the current invention such that the tuning waveform sweeps the VCL source at a predominately fixed repetition rate. Another preferred embodiment operates the current invention such that the tuning waveform sweeps the VCL source over a predominately fixed wavelength tuning range, preserving axial resolution. One preferred embodiment operates the current invention at a fixed repetition rate, fixed wavelength sweep, and fixed trajectory. This mode of operation can be beneficial for an OEM supplier that reuses a standard OCT engine in multiple products. In the more general case, one embodiment comprises a tunable source that is driven with variable drive waveforms to achieve different operating modes with respect to sweep repetition rate. Also in the more general case, one embodiment comprises a tunable source that is driven with variable drive waveforms to achieve different operating modes with respect to sweep range.

The waveform driving the tuning element can be synthesized from an analog source or a digital source. The key feature of the electronics that generate the waveform is ability to adjust the shape of the waveform by changing input parameters. A preferred embodiment of the current invention uses a D/A converter to generate the waveform from a digital stream of data that can be read from a stored representation of the data or synthesized on the fly. A microprocessor, microcontroller, FPGA, DSP, circuit with memory and counting (addressing) capability, or similar digital processing unit can be connected to the D/A to control data flow and load waveform data. The drive waveform can be expressed as a mathematical function or it can be a sequence of arbitrary waveform values. A sequence of individually controllable arbitrary waveform values, such as would be represented as a memory array within which each value could be adjusted individually, can be expressed as a series of delta functions. Another preferred embodiment of the present invention uses a bank of analog oscillators, the amplitude and phase of which can be adjusted, and generates the waveform by summing the output of the oscillators with a DC offset voltage. Proper drive electronics are included to interface the waveform signal to the tuning transducer or tuning material. The preferred embodiment of the present invention uses a tuning waveform that alters the tuning response of the tuning element from the tuning element's natural dynamics to achieve a tuning response that is preferable for imaging by improving at least one of the following: sweep repetition rate, sweep speed, sweep acceleration, sweep range, sweep linearity, and sweep duty cycle. In the most general case, the preferred embodiment determines a tuning response to improve OCT imaging performance.

Very many different drive waveforms can be used to drive the tunable source of the present invention. In one preferred embodiment, a tuning trajectory of a mathematical model can be optimized and the resulting drive waveform of the optimized model applied to the experimental apparatus. This approach works well for certain tuning element dynamics and when the model closely matches the experimental dynamics. It is also possible to optimize the waveform experimentally with the tunable source in the optimization loop. In either case, a waveform is parameterized and applied to the model or the experimental hardware. It is possible to adjust the parameters of the waveform by hand. However, in the preferred embodiment, the parameters of the waveform are adjusted by an optimization algorithm.

Figure 22:
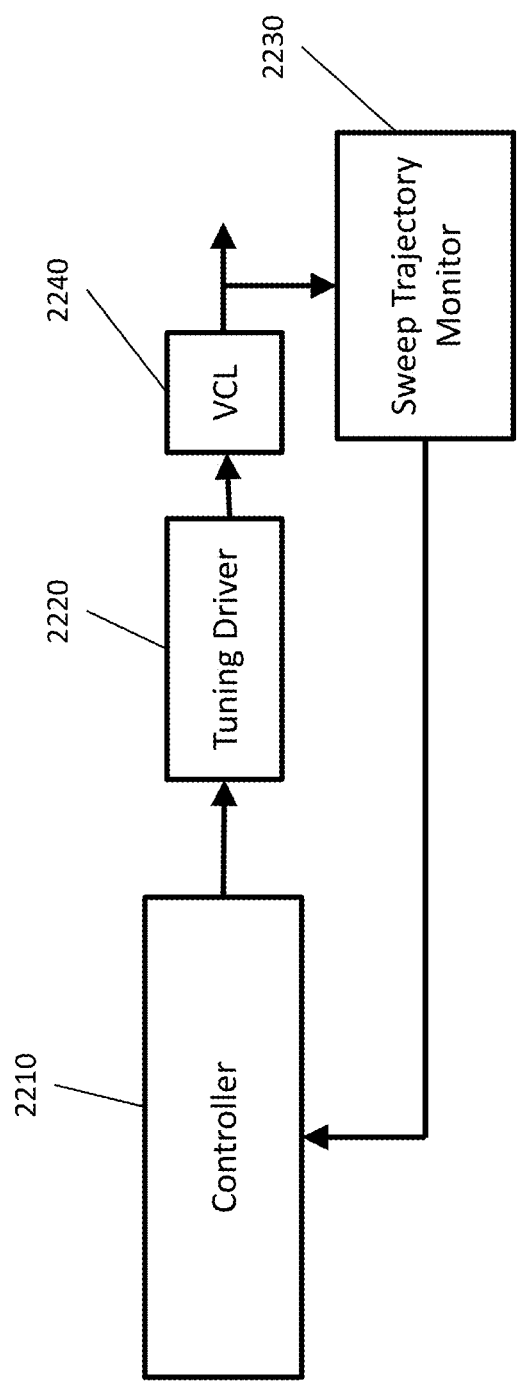
FIG. 22 is a block diagram of closed loop method of waveform generation.
Figure 23:
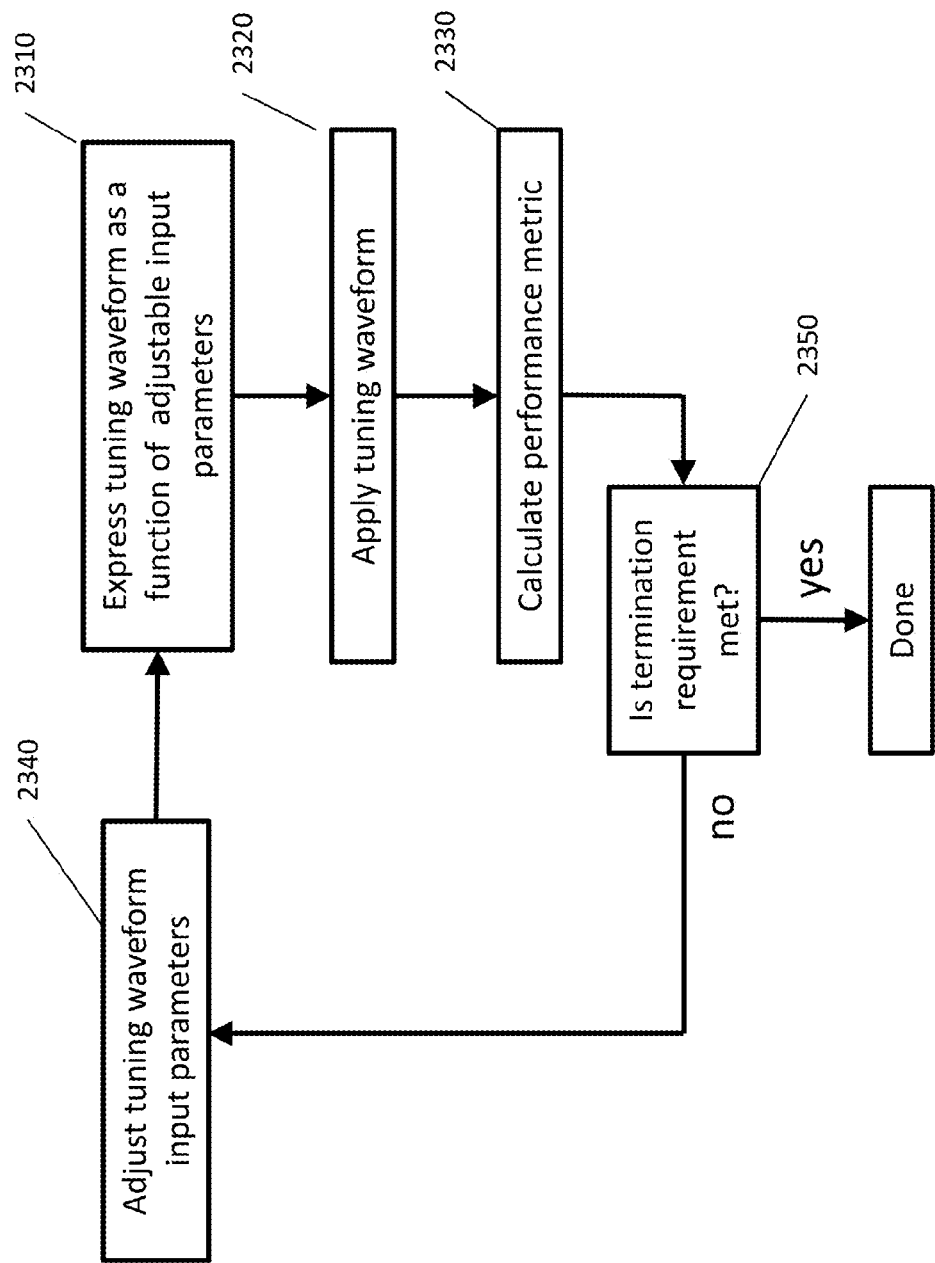
FIG. 23 is a flow chart illustrating a method for tuning driver waveform synthesis.

One embodiment of the present invention automates waveform synthesis by measuring optical properties of the output emission from the VCL with a monitor 2230 and adjusting the trajectory to the tuning driver 2220 that drives the VLC 2240, as illustrated in FIG. 22. The adjustment can be made by a controller 2210 that takes the monitor signal as input and uses the information in the monitor signal to adjust the waveform. The controller can be a processor, FPGA, microcontroller, analog circuit or other electronic circuit that can compute a proper correction. The controller can be embedded in the tuning driver or can be an external computational unit. The controller can also be a computer connected to or otherwise communicating with the OCT imaging system. FIG. 23 shows a flow chart of one method to synthesize a waveform given the feedback arrangement of FIG. 22. One embodiment of the present invention uses a method for synthesizing drive waveforms that comprises expressing the tuning waveform as a function of adjustable input parameter values to create a tuning waveform expression 2310, applying the tuning waveform to the tuning element or a mathematical model of the tunable source dynamics to generate at least one experimental measurement or simulated wavelength sweep 2320, calculating a value of a performance metric or an objective function based on the experimental measurement or the simulated wavelength sweep 2330, adjusting the value of the input parameters to optimize the value of the performance metric or objective function 2340. In general, the method repeats the steps multiple times as part of an optimization process with an adjustment or correction applied to the input parameters for each iteration until a termination criterion is met 2350. In the preferred embodiment, the design goals are most generally formulated into an objective function or performance metric to be optimized. Constraints can also be applied on the inputs and outputs to the system and included in the objective function or as constraints to the optimization process. Further, it is possible to combine multiple performance metrics and to form a multi-objective metric of performance.

The waveform can be expressed using mathematical formulas or simply be an array of data with every data point adjustable, or groups of data points adjustable. One embodiment uses a tuning waveform comprising a combination of basis functions, the tuning waveform altering the tuning response of the tuning element from the tuning element's natural dynamics. Equation 4 shows a generic representation of a voltage waveform, V, expressed as a function of time, t, that is a combination of n basis functions, $b_i(t)$, where each $a_i$ is the basis coefficient for the ith basis function and acts as the adjustable input parameter that define the drive waveform.

$$V(t)=(t)+a_1 b_1(t)+a_2 b_2(t)+a_3 b_3(t)+ \ldots +a_n b_n(t) \qquad \text{Eq. 4}$$

The method for synthesizing a drive waveform may comprise an expression including a DC offset value as an adjustable input parameter. The method for synthesizing a drive waveform may comprise an expression comprising a summation of sinusoidal functions with different frequencies, the sinusoidal functions having adjustable amplitude and phase as adjustable input parameters, or equivalently comprising both sine and cosine functions with fixed phase to provide phase adjustability by balancing sine and cosine relative contribution. The method for synthesizing a drive waveform may comprise an expression comprising a chirped cosine function with adjustable input parameters. The method for synthesizing a drive waveform may comprise an expression comprising spline functions with control points as adjustable input parameters. In the more general case, the method for synthesizing a drive waveform may comprise an expression comprising mathematical functions with input values as adjustable input parameters, including, but not limited to the selection of one or more of: square root functions, $N^{th}$ degree root functions where N is an integer, decimal, or fractional value, exponential functions, logarithmic functions, squared functions, $N^{th}$ power functions where N is an integer, decimal, or fractional value, trigonometric functions, step functions, impulse functions, gamma functions, Gaussian functions, linear functions, triangular functions, piecewise functions, and other functions known in the art of signal representation. In the most general case, the method for synthesizing a drive waveform may comprise an expression comprising mathematical functions with input values as adjustable input parameters. There are many possible mathematical functions that can be implemented. What follows are a few practical examples. Equation 5 shows a DC value combined with a sum of sinusoidal functions. The frequency of the sinusoidal functions are the fundamental of the sweep repetition rate, $\omega$, and the harmonics:

$$V(t)=a_1+a_2 \sin(\omega t+a_3)+a_4 \sin(2\omega t+a_5)+a_6 \sin(3\omega t+a_7)+ \ldots +a_{n-1}\sin((n/2-1)\omega t+a_n) \qquad \text{Eq. 5}$$

To compensate for the voltage squared term in the actuation force (see Eq. 3), it can be beneficial to calculate the voltage as the square root of a mathematical function, as shown in Eq. 6 in order to improve rates of convergence.

$$V(t) = \sqrt{\begin{array}{l} a_1 + a_2\sin(\omega t + a_3) + a_4\sin(2\omega t + a_5) + \\ a_6\sin(3\omega t + a_7) + \ldots + a_{n-1}\sin((n/2-1)\omega t + a_n) \end{array}} \qquad \text{Eq. 6}$$

Another useful waveform contains piecewise concatenation of chirped cosine functions, as shown in Eq. 7 and used to generate the drive signals shown in FIGS. 16A, 16B, 19, and 20. Each of the m segments of the waveform is defined by a chirped cosine function and the parameters $A_n$, $s_n$, $P_n$, $L_n$, $D_n$ and $E_n$ chosen such that the functions are smooth in position and higher order derivatives at the boundaries, where $A_n$ is the relative amplitude of the nth composition waveform, $s_n$ is a phase shifting factor within the power term for the nth composition waveform, $L_n$ is a scaling factor on the duration of the nth composition waveform, $D_n$ is the relative phase delay factor of the nth composition waveform, $P_n$, is the power factor of the nth composition waveform, $E_n$ is the relative offset of the nth composition waveform, $t_n$, the piecewise switching time for each of the m chirped cosine functions, and t is the time:

$$V(t) = V_{DC} + V_{AC} \cdot V_P(t) \quad \text{Eq. 7}$$

where $$V_P(t) = \begin{cases} A_1 \cos((t-s_1)^{p_1} \cdot L_1 + D_1) + E_1 & \text{if } t \geq 0 \text{ and } t < t_1 \\ A_2 \cos((t-s_2)^{p_2} \cdot L_2 + D_2) + E_2 & \text{if } t \geq t_1 \text{ and } t < t_2 \\ A_m \cos((t-s_m)^{p_m} \cdot L_m + D_m) + E_m & \text{if } t \geq t_{m-1} \text{ and } t < t_m. \end{cases}$$

In the above method described by Eq. 7, $t_m$ is generally equal to the period of the drive waveform and t is reset to zero to repeat the waveform when t≥tm. $V_{DC}$ is a DC offset term and $V_{AC}$ is a scaling factor on the repetitive waveform component, $V_P(t)$. As shown in FIGS. 16 and 19, small perturbations to the waveforms can be included to counteract resonances in the MEMS actuator to achieve a preferred sweep behavior.

It is possible to identify a mathematical model of the dynamics of the tuning element such that the mathematical model and the experiment behave substantially the same. The mathematical model may be derived from first principles with modeling parameters adjusted to match experimental data. The mathematical model may also be obtained by using system identification methods. One useful modeling approach identifies linear approximating models at different deflection positions using subspace identification methods from the field of motion control and interpolates the linear models as a function of tuning position. As part of the methods for synthesizing a waveform, the waveform may be applied to the experimental apparatus or to the model to determine or predict the wavelength tuning response.

In the preferred embodiment of the present invention, performance metrics are associated with a wavelength tuning response. For example, in OCT, it is desirable to minimize the maximal peak fringe frequency to achieve long range imaging for a given constraint on acquisition system bandwidth. In one preferred embodiment, the experimental measurement from the monitor is an interferometric fringe from the tunable source emission as the tuning element sweeps. The zero crossings of the fringe indicate locations of equal wavenumber spacing. One preferred embodiment defines the performance metric as the minimal optical fringe zero-crossing spacing in time or equivalence thereto, which is maximized to reduce fringe velocity. The fringe velocity can also be determined from a Hilbert transform applied to the fringe data. Similarly, one preferred embodiment of the present invention uses the maximum peak fringe frequency as a performance metric to be minimized. Given a vector of estimated fringe frequencies, $\vec{f}$, where the estimate is calculated from an experimental measure of the experimental apparatus or from a simulation model over the imaging portion of the sweep, and a vector of adjustable input parameters, $\vec{a}$, the performance metric, G, to be minimized is given by $G(\vec{a})=\max(\vec{f}(\vec{a}))$. Minimizing the fringe frequency itself is not sufficient for defining the optimization goals because the optimizer would drive the wavelength sweep range down to zero to minimize the fringe frequency. It is therefore necessary to require the optimizer to minimally span the desired sweep range during the optimization. Desired starting (short) and ending (long) wavelengths can be defined as $w_{desired}^{start}$ and, $w_{desired}^{end}$ respectively and included in the optimization as constraints. For example, the exterior penalty method of constraining a numerical optimization could be used where $p_{start}(\vec{a})=w_{actual}^{start}(\vec{a})-w_{desired}^{start} \leq 0$ and $p_{end}(\vec{a})=w_{desired}^{end}-w_{actual}^{end}(\vec{a}) \leq 0$, and where $w_{actual}^{start}(\vec{a})$ and, $w_{actual}^{end}(\vec{a})$ are determined from an experimental measurement or estimation of the starting and ending wavelengths, respectively. Combining the performance metric with the penalty functions and an adjustable penalty parameter, c, the objective function becomes $$o(\vec{a})=G(\vec{a})+c[\max(0,p_{start}(\vec{a}))^2+\max(0,p_{end}(\vec{a}))^2].$$

As the adjustable penalty parameter, c, is increased in value, the effect of the exterior penalty function becomes more prominent. There is a balance between minimizing peak fringe frequency and achieving the desired sweep range as formulated. Typically, one would progressively increase the value of c until sufficient wavelength tuning range was achieved. In practice, it is desirable to set $w_{desired}^{start}$ and, $w_{desired}^{end}$ a little beyond the desired tuning range wavelengths so that moderate values of c can be used while still reaching the tuning range goals. A traditional formulation of an exterior penalty function method has been described. Other methods of optimization, including other formulations of exterior penalty methods, interior penalty methods, and other methods for achieving the design goals are also included in the present invention.

Alternatively, a predefined trajectory can be determined and the tracking error of the model or experiment minimized as the performance metric. One preferred embodiment of the present invention defines a desired response trajectory and acts to minimize the tracking error between an experimental response trajectory and the desired response trajectory. The trajectory can be defined with respect to wavelength or wavenumber. Since a MEMS tunable VCSEL tunes wavelength proportional to actuator displacement, for convenience, wavelength is used for this example, although an equivalent formulation exists with respect to wavenumber and the two methods can be used interchangeably. The desired trajectory should account for limitations in the actuator dynamics with respect to maximum velocity, maximum acceleration, and maximum slew rate of the drive electronics. The desired trajectory should also be smooth (continuous derivative) with respect to position. To avoid exciting resonances in the MEMS actuator, the desired trajectory should also be smooth in higher order derivatives of positions, such as velocity and acceleration. Very many methods have been developed in the field of motion control for generating efficient trajectories to achieve rapid convergence to position or velocity goals in the presence of flexible actuated systems. The trajectories achieve smoothness goals by piecewise concatenation of trajectory segments with consideration of maintaining smoothness at the points of transition and abiding by velocity and acceleration constraints, for example, trapezoidal profiles, S-curves, cycloids, half cosine, polynomial, and other parameterized curves. An example desired trajectory for unidirectional scanning would join a starting and ending wavelength with a segment of constant velocity in wavenumber to achieve a linear portion of the sweep. At the end of the sweep, the trajectory reverses direction without exceeding actuator acceleration limits. A fly-back portion of the sweep returns the MEMS tuning element to a position slightly beyond the starting wavelength position so that the MEMS tuning element can again reverse direction and accelerate to the required velocity and position of the start of the next constant velocity wavenumber sweep. Given an experimental wavelength trajectory, $\vec{P}_{exp}(\vec{a})$, and a desired wavelength trajectory, $\vec{P}_{des}$, a tracking error vector, $\vec{P}_{error}(\vec{a})$, can be formed as $\vec{P}_{error}(\vec{a}) = \vec{P}_{exp}(\vec{a}) - \vec{P}_{des}$. An optimization performance metric that is a measure of the size of the tracking error vector is defined. One possible metric is the sum of squared differences (SSD), which is the squared form of the L2 norm. The optimization metric for applying an SSD measure to the error vector would be:

$$G(\vec{a}) = \|\vec{P}_{error}(\vec{a})\|_2^2$$

Higher powered norms, including the infinity norm, can also be used to increase the tracking penalty associated with regions of high tracking error. Any measure of closeness to the desired trajectory can be used as the metric, including, but not limited to the maximum tracking error, sum of squared differences of tracking error, and any norm on the tracking error. It is also possible to apply different weighting to different portions of the sweep. For example, using a weighting coefficient or weighting function one could weight the regions of the imaging portion of the sweep higher than the regions of the turnaround and fly-back in order to emphasize the tracking quality of the imaging portion of the sweep.

If the analytical expression of the waveform generates voltages that exceed the capability of the drive electronics, then the sensitivity of the expression to small perturbations, such as the finite difference perturbations associated with many optimization algorithms, is diminished, which can reduce effectiveness of the optimization process. During the optimization, it can be advantageous to constrain the output voltages generated by the drive waveform expression to avoid saturation of the voltage amplifier and to avoid generating negative voltages. Given a maximum and minimum voltage, $V_{max}$ and $V_{min}$, respectively, and a vector of voltages in the waveform, $\vec{V}$, an additional constraint can be included in the optimization objective function. A maximum and minimum constraint function, $p_{v\,max}(\vec{a}) = V_{max} - \max(\vec{V})$ and $p_{v\,min}(\vec{a}) = \min(\vec{V}) - V_{min}$ can be defined and included in the objective function as:

$$O(\vec{a}) = G(\vec{a}) + c_{voltage}[\max(0, p_{v\,max}(\vec{a}))^2 + \max(0, p_{v\,min}(\vec{a}))^2].$$

Figure 24:
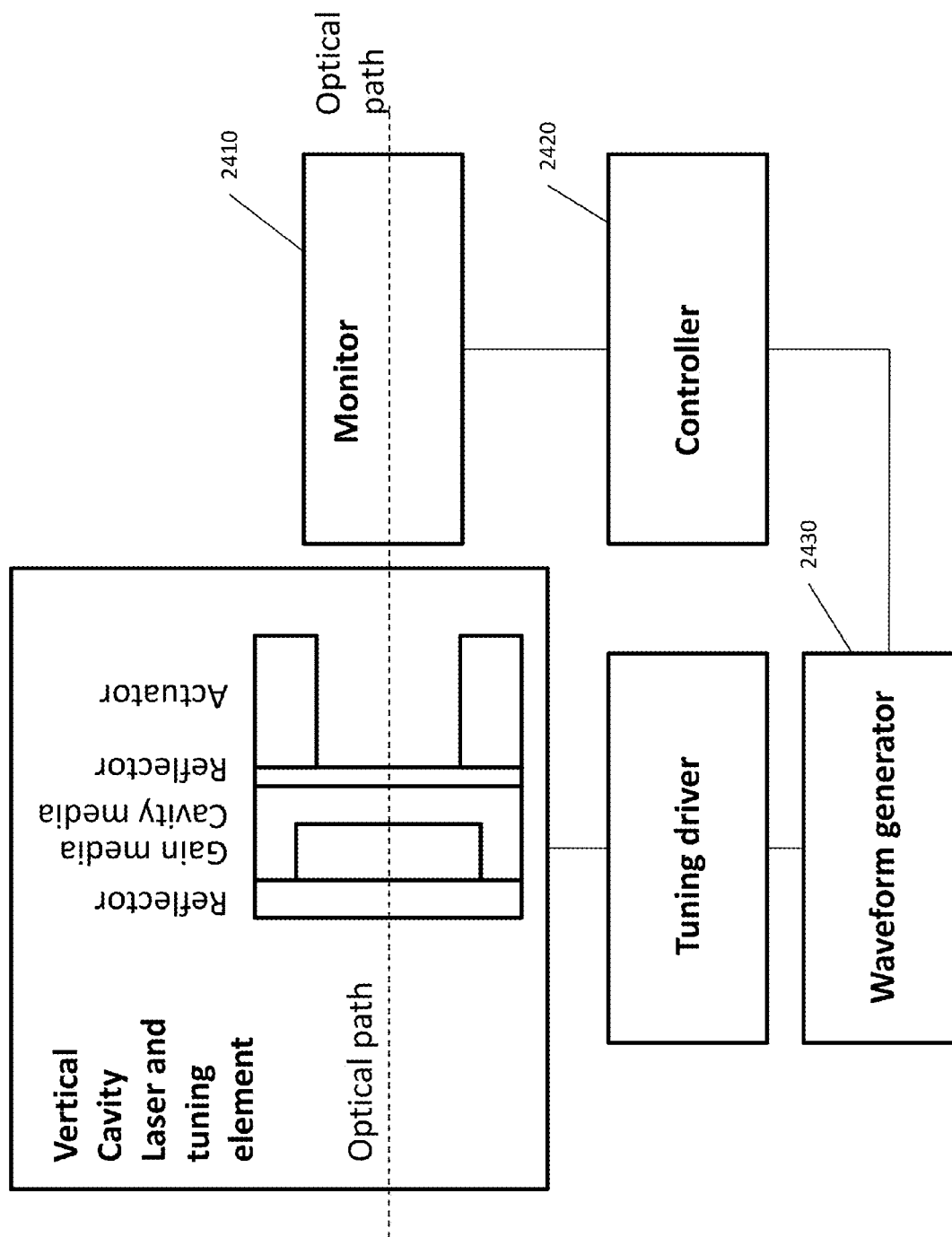
FIG. 24 is a block diagram of a closed loop wavelength tuning subsystem.
Figure 25:
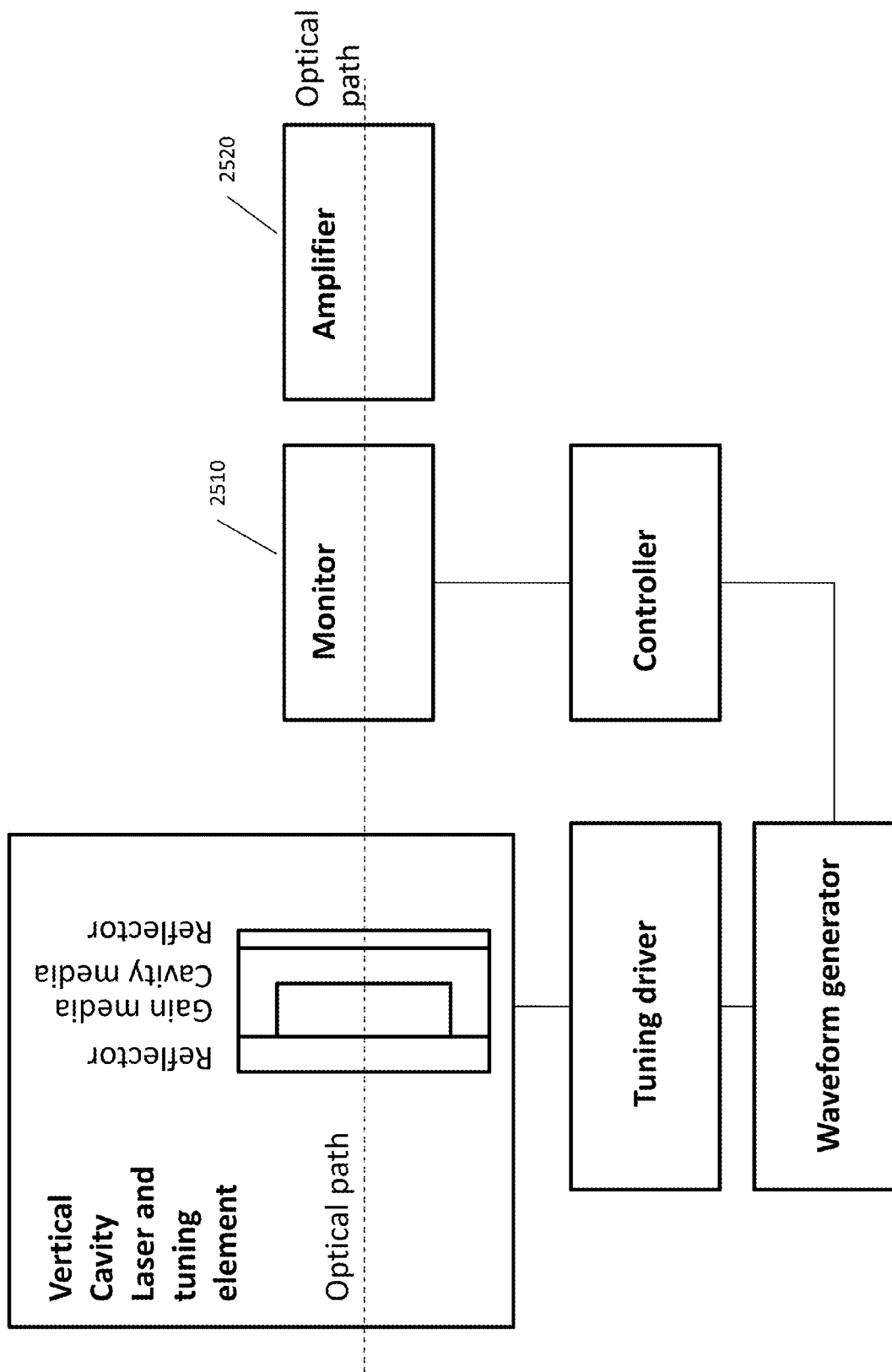
FIG. 25 is a block diagram of a closed loop wavelength tuning subsystem with optical amplifier.

Calculation of the performance metric requires an estimate of the sweep trajectory, or a measurement of a characteristic of the sweep trajectory. The measurement will generally be associated with the wavelength vs. time response from the tunable source emission or simulated output as the tuning element sweeps. A monitor is included in the present invention to measure the sweep response. FIG. 24 illustrates a block diagram of a tunable source with an optical monitor 2410 measuring the output of the VCL. The optical monitor is referred to as a monitoring detector, monitoring module, or monitor, all of which are equivalent in this application. The monitor takes a small portion of light from the output of the VCL for measurement purposes and passes the majority of the light to the OCT interferometer for imaging purposes. Information about the sweep is use as input from the monitor to a controller 2420, which in turn generates a waveform trajectory 2430 to be applied to the experimental apparatus. FIG. 24 illustrates monitoring the output of the VCL directly. FIG. 25 illustrates monitoring 2510 the output of the VCL before amplification 2520.

Figure 26:
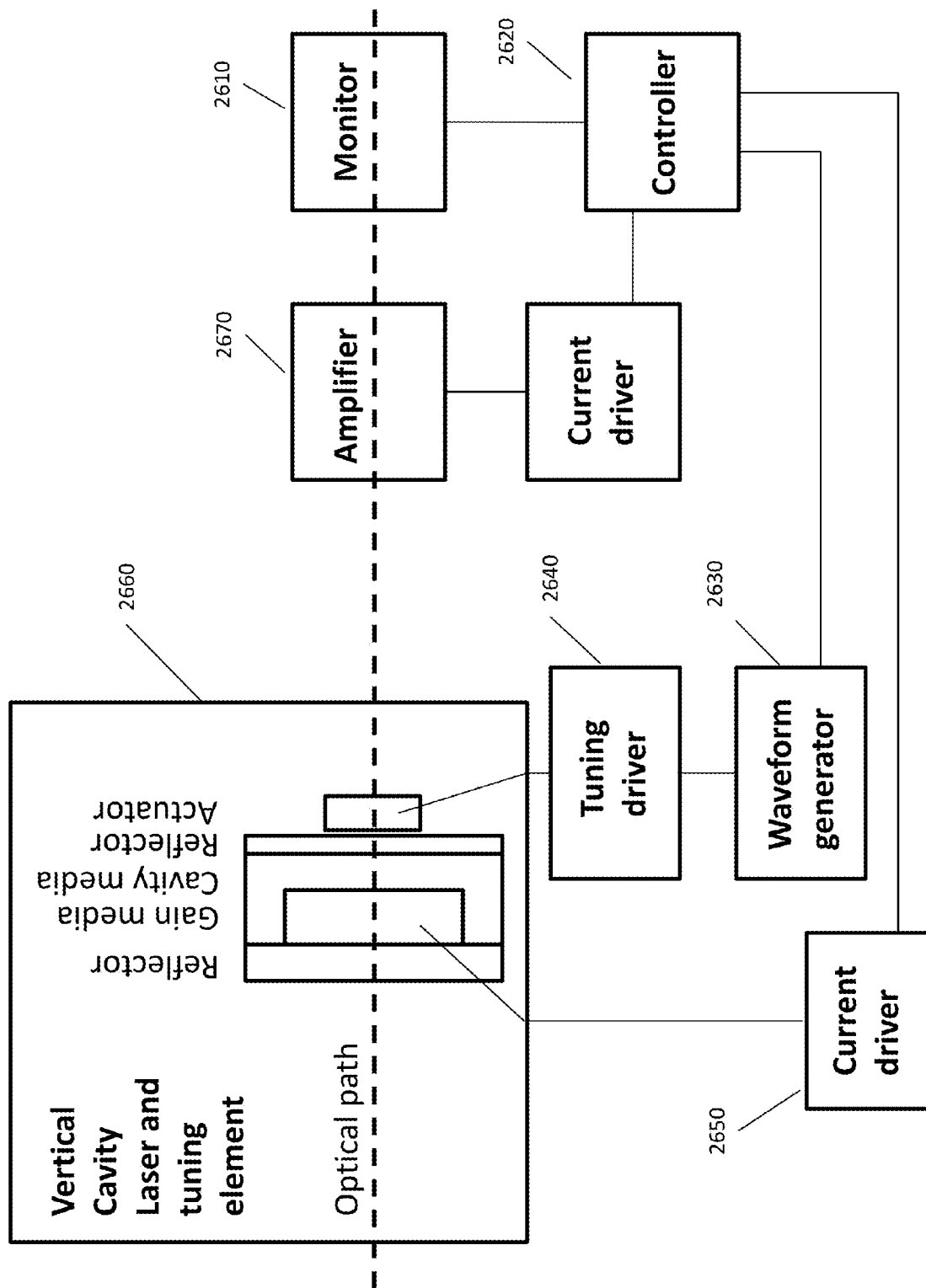
FIG. 26 is a block diagram of a closed loop wavelength tuning subsystem with optical amplifier and current driver.

Monitoring the output of the VCL directly or before amplification can result in an improved measurement without potential influence of ASE from an amplifier. FIG. 26 illustrates monitoring 2610 the output of the VCL after post amplification 2670, which can be desirable if ASE from the amplifier does not detrimentally affect the measurement. FIG. 26 shows a monitor 2610 and controller 2620 connected to a waveform generator 2630, tuning driver 2640 and current driver 2650 for the VCL 2660 and optical amplifier 2670. The waveform generator in this diagram could be a D/A converter while the current driver 2650 could be turned on or off from the controller, for example to blank out a sweep. In general, the D/A converter and controller can be integrated into the tuning driver. The D/A converter and controller can also be separate from the current driver. It is also possible that a D/A converter be included before or as part of the current driver to provide waveform generation capability for the current driver. In general, the D/A converter and a controller can be integrated into the current driver or exist before the current driver.

Figure 27:
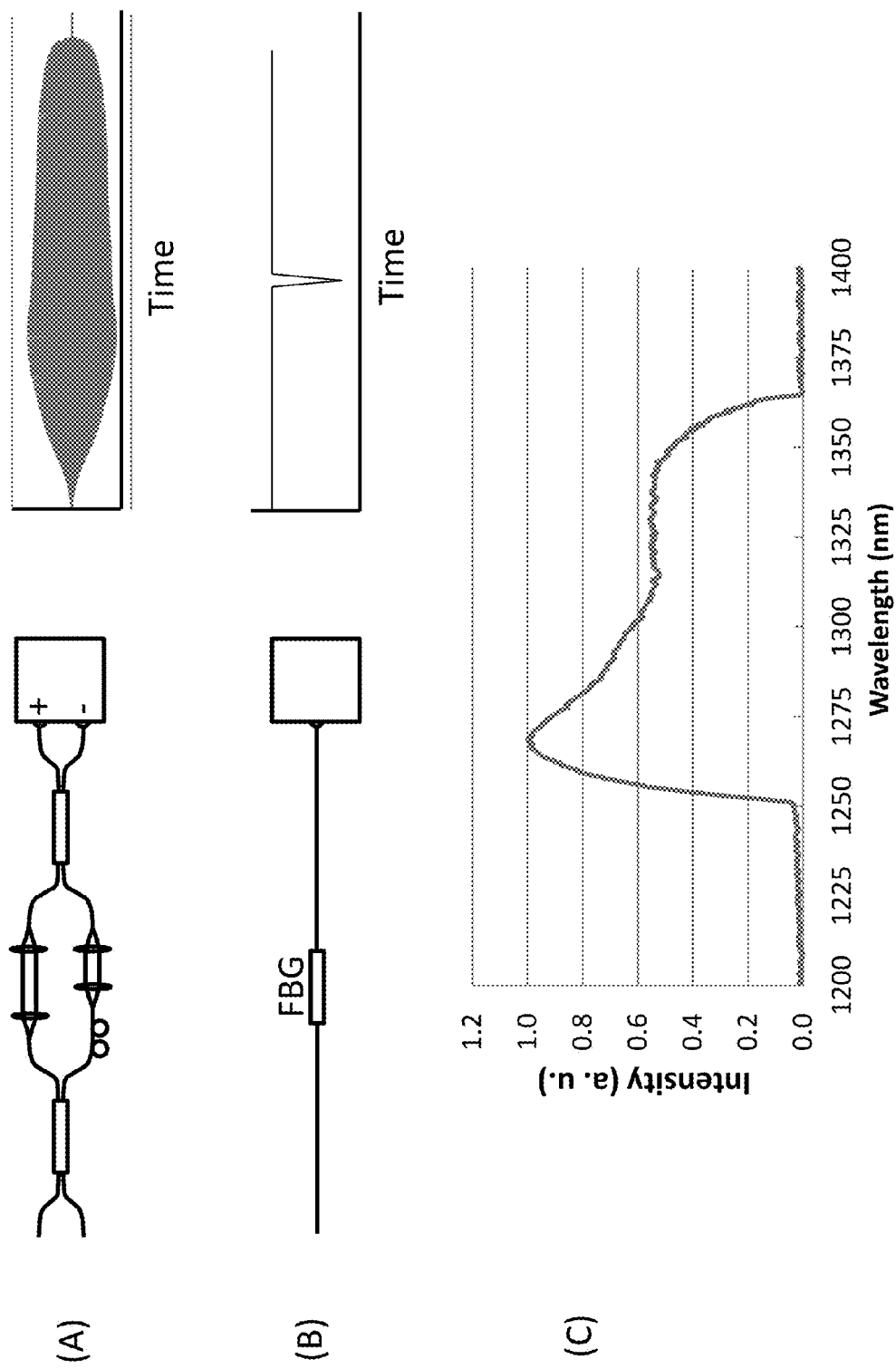
FIG. 27 is a set of drawings and plots illustrating a method of sweep measurement based on an interferometric fringe.
Figure 33:
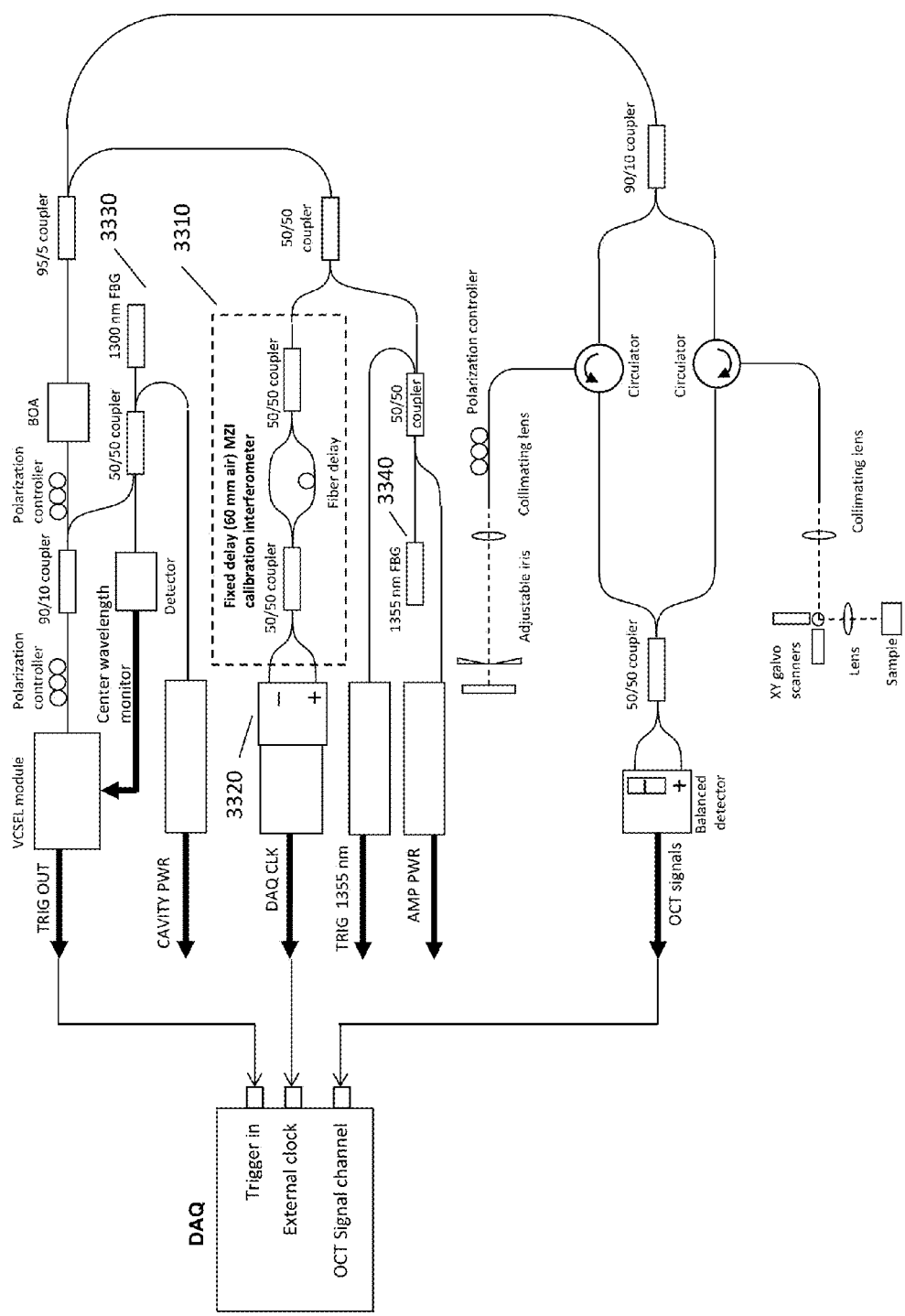
FIG. 33 is a block diagram of an OCT imaging system showing details of an imaging system that use circulators, an optical wavelength trigger, and optical clocking.

FIG. 27 illustrates a method for measuring the tuning response of the VCL source as part of the monitor. As the wavelength is swept, a Mach Zehnder interferometer generates an interferometric fringe, as shown in FIG. 27A. If the Mach Zehnder interferometer is dispersion balanced, then the fringe zero crossings (or phase) represent equal k (wavenumber) intervals. If the optical path length of the MZI is known or has been experimentally calibrated, then the size of the k interval is also known. If the MZI is not dispersion balanced, as would be the case with an all fiber MZI, then the dispersion can be calculated or experimentally determined and used to estimate k intervals. The calibration signal can come from a fiber Bragg grating, as illustrated in FIG. 27B. An FBG 3340 for this purpose is shown in FIG. 33. Simultaneous acquisition of a wavelength calibration signal allows absolute calibration of the wavelength sweep vs. time by counting wavenumber increments from the calibrated wavelength. A Fiber Bragg Grating, Fabry-Perot filter, grating and detector, or any other optical filter can also be used to generate a wavelength selective signal. The calibration signal can also come from a measurement of the sweep spectrum as acquired by an optical spectrum analyzer or other spectral analysis device, as shown in FIG. 27C. If the fringe does not have any stationary points (direction reversals in the sweep), then the maximum and minimum extreme spectral signal represent the starting and ending wavelengths of the sweep and the wavenumber either increases or decreases monotonically to allow direct counting of k intervals to calibrate the sweep trajectory. The wavelength calibration signal can acquired with an A/D converter that is clocked off the same signal as the A/D converter acquiring the MZI fringe. The calibration signal can also come from a counting circuit that locates the signal in time relative to the MZI fringe. The acquired data can be filtered in processing or electronics to improve the ability to resolve the spectral peak.

Figure 28:
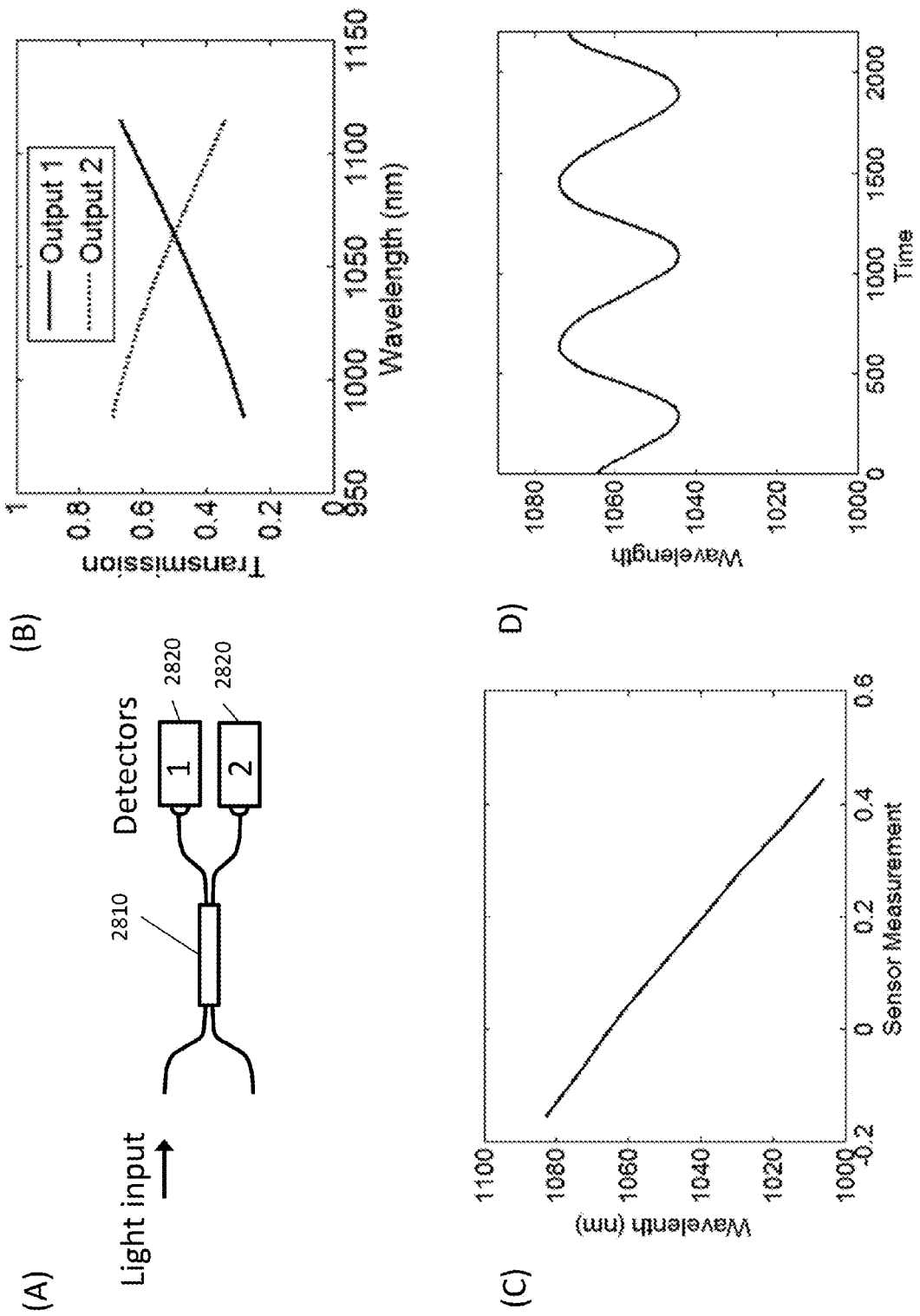
FIG. 28 is a set of drawings and plots illustrating a method of sweep measurement based on detection of split power levels.

A different wavelength measuring method and experimental apparatus is shown in FIG. 28. A fiber optic coupler 2810 receives input light and splits the light into two paths, each path being detected by a photodetector 2820, as shown in FIG. 28A. The splitting ratio of a fiber coupler is wavelength dependent. FIG. 28B shows an experimental measurement of the transmission of a fiber optic coupler operating near 1050 nm wavelengths. The power through the coupler is conserved such that as the power transmitted by output 1 decreases, the power transmitted by output 2 increases accordingly. A normalized sensor measurement, $S_{est}$, and a power estimate, $P_{est}$, can be calculated as a function of time, t, from the output of the two detectors, $D_1$ and $D_2$ connected to the fiber coupler outputs that is invariant to power levels and wavelength dependence of the detectors, $g(S_{est})$, as $$S_{est}(t) = \frac{D_1(t) - D_2(t)}{D_1(t) + D_2(t)}$$

and $$P_{est}(t) = g(S_{est}(t)) * (D1(t) + D2(t)).$$

There is a one-to-one relationship between the sensor measurement, $S_{est}$, and the wavelength of measured light, which can be determined by experimental measurement of the outputs of the sensor and a wavelength measuring instrument at a set of calibration points, as shown in FIG. 28C. Given a sensor measurement, the corresponding wavelength of light can then be determined by interpolating the data shown in FIG. 28C to determine the wavelength of input light. Knowing the wavelength of light allows the wavelength dependent gain of the detector, $g(S_{est})$, to be calculated. Acquiring the data from the two detectors with an A/D converter for each detector channel allows a time history of the wavelength of light to be recorded. Calibrating the points in the time history of the sensor measurement allows the wavelength of light vs. time to be estimated, as experimentally shown in FIG. 28D. Power can be similarly computed. One preferred embodiment of the present invention uses a fiber optic coupler in the wavelength sensor of the monitor. Other methods of implementing the wavelength sensor that use a wavelength sensitive light splitter or filter are also possible. Wavelength dependent filters can transmit a portion of the light to a first detector and reflect the other portion of light to a second detector. One preferred embodiment of the present invention uses filters made from dielectric or multilayer coatings in the wavelength sensor. One preferred embodiment includes a monitoring detector that comprises a wavelength dependent component for splitting the light as a function of wavelength into multiple channels and the relative power of the different channels of light measured. One preferred embodiment includes a monitoring detector that comprises a wavelength dependent component for splitting the light as a function of wavelength into multiple channels and the relative power of the different channels of light measured to estimate the wavelength vs. time of the sweep. One preferred embodiment includes a monitoring detector that comprises a wavelength dependent coupler, beam splitter, or filter for splitting the light as a function of wavelength into multiple channels and two detector diodes to measure the relative power of the different channels of light to estimate the wavelength vs. time of the sweep.

The preferred embodiment synthesizes a waveform based on a set of waveform parameters, applies the waveform, calculates a performance metric on the response, and updates the waveform parameters with the goal of improving the sweep performance. In one preferred embodiment, the steps are repeated multiple times and the input parameters are adjusted by an optimization algorithm. In one preferred embodiment, the steps are repeated multiple times and a correction applied to the input parameters for each iteration. An appropriate optimization algorithm can be chosen from any of the many optimization algorithms known in the field of numerical optimization. In the preferred embodiment, the optimization algorithm can be selected from any one or more of the following: Newton's method, quasi-Newton methods, gradient descent, parallel stochastic gradient descent, conjugate gradient, genetic algorithms, simulated annealing, hill climbing, or any other optimization algorithm known in the art of numerical optimization. Many optimization algorithms alternate between determining a search direction vector and performing a line search along the search direction vector. In one preferred embodiment, the optimization algorithm executes a line search along a search direction vector as part of the optimization. In one embodiment, the optimization process continues while the swept source is running, constantly attempting to improve performance and maintaining the desired trajectory. In another embodiment, the optimization algorithm iterates until a termination criterion is met. In one embodiment, the optimization is performed at the factory before sale of the OCT instrument to obtain the desired sweep trajectory or trajectories. The waveforms are saved and the instrument plays the waveforms back in the field. In another embodiment, the optimization algorithm iterates during use of the imaging system to generate a new desired tuning trajectory. This may occur after sale of the instrument as required by the users application or imaging task at hand.

It is possible that the tunable source be operated in different environmental conditions. It is also possible that a component in the tunable source the might age. In one embodiment, the optimization algorithm iterates during use of the imaging system to compensate for changes to the tuning element dynamics. In one preferred embodiment, waveforms are synthesized and stored for playback, a method that works well if the actuator dynamics do not change with time or environmental conditions. In another preferred embodiment, the optimization process can be performed during operation or deployment for maintaining a desired trajectory in the presence of changing dynamics or generating new trajectories, possibly on the fly.

It is possible to sense changes in the sweeping performance and make small modifications to the driving waveform to compensate without performing a complete optimization. One preferred embodiment uses a closed loop control to maintain the desired sweep trajectory in the presence of environmental changes, temperature changes, internal charging, aging of the device, or any other perturbation to the actuation or dynamics of the device. More specifically, the preferred embodiment uses a tunable laser with a closed loop control to maintain the desired sweep trajectory in the presence of environmental changes, temperature changes, internal charging, aging of the device or other perturbation, the closed loop control reading a wavelength sensitive trigger signal and appropriately adjusting the drive waveform to the actuator or transducer of the tuning mechanism of the VCL source by changing a single or small subset of the waveform parameters. One preferred embodiment changes the DC voltage of the drive waveform as the waveform parameter in the closed loop. It is possible that a component within the tunable source develops an electrical charge during operation. One preferred embodiment of the present invention uses a drive signal to the tuning element that can reverse electrical polarity to compensate or nullify the effects of electrical charging of the actuator. The preferred embodiment of the present invention in general uses a tuning element in the laser that is of a design that is resistant to charging.

As mentioned previously, it is possible to combine multiple individual metrics for a multi-objective optimization. The method of the preferred embodiment includes the case where the performance metric or objective function comprises the maximal peak optical wavenumber velocity during the sweep or equivalence thereto. The method includes the case where the performance metric or objective function comprises the maximal peak optical fringe frequency or equivalence thereto. The method includes the case where the performance metric or objective function comprises the minimal optical fringe zero-crossing spacing in time or equivalence thereto. The method includes the case where the performance metric or objective function comprises the degree of linearization of the sweep with respect to wavenumber vs. time or equivalence thereto. The method includes the case where the performance metric or objective function comprises the duty factor of the sweep or equivalence thereto. The method includes the case where the performance metric or objective function comprises the sweep range or equivalence thereto. The method includes the case where the performance metric or objective function comprises a measure of the difference between the experimental or simulated sweep trajectory and a desired sweep trajectory or equivalence thereto. The method includes the case where the performance metric or objective function comprises a measure of the difference between the experimental or simulated sweep trajectory and a desired sweep trajectory, where any measure of closeness to the desired trajectory can be used as the metric, including, but not limited to the maximum tracking error, sum of squared differences of tracking error, and any norm on the tracking error, or equivalence thereto.

Spectral Envelope Shaping

The spectral envelope of the wavelength sweep and associated interferometric fringe determine the shape of the OCT axial point spread function (PSF), as illustrated in FIGS. 4D and 4E. As shown in case 1 of FIGS. 4D and 4E, significant sidelobes are generated if the spectral envelope has a sharp or hard edged transition at the start or end of the sweep. These sidelobes generate artifacts (replicated ghost images) in the OCT data, can be misleading with respect to interpreting the OCT data, and can cause image processing segmentation errors, resulting in erroneous distance or thickness measurements. The sidelobes can be reduced by shaping the envelope spectrum to approximate a Gaussian profile or any one of many windowing, apodization, or tapering functions, such as Hamming, Hann, cosine, Blackman, Nuttall, or any other windowing function known in the art of signal processing. Shaping the spectral envelope to an approximate Gaussian, as shown in FIGS. 4D and 4E case 2, significantly reduces the sidelobes when compared to case 1. Narrowing the Guassian envelope to drive the starting and ending edge transitions to a smooth transition near zero further reduces the sidelobes, as shown in case 3 of FIGS. 4D and 4E. However, there is a progressive loss of OCT axial resolution with increasing apodiziation, as shown in FIG. 4F. In general, more aggressive shaping of the spectrum with apodization results in a reduction of sidelobes, but at a cost of OCT axial resolution. However, if the spectral envelope is not well balanced between short and long wavelengths, or there is a dip in the spectrum, spectral shaping can both decrease sidelobes and improve OCT axial resolution by obtaining a more preferential spectral shape and spectral width.

It is common in OCT systems to shape the spectral envelope in post processing using numerical techniques. However, in the case of OCT imaging where there is a maximum allowed light exposure on the sample, shaping the spectrum in post processing necessarily results in a suboptimal OCT sensitivity because excess light in the apodization attenuated regions of the sweep counts as exposure, thereby reducing the amount of actual light that can be applied in the lesser apodized regions of the sweep. It is therefore preferential to shape the spectrum at the light source so that the light returning from the sample is already of the preferred spectral shape.

The preferred embodiment of the present invention comprises at least one current driver that is capable of affecting the spectral envelope of the wavelength sweep. The current driver stimulates a gain material in the tunable source to control output emission levels. In one preferred embodiment, the current driver is connected to a pump in the tunable source. In another embodiment, the current driver stimulates the VCL gain material directly. In another embodiment, the current driver stimulates the gain material in an optical amplifier. Appropriately adjusting the current in the current driver during the sweep allows shaping of the envelope of the spectral sweep.

Very many different current driver implementations can be used. The preferred embodiment has a current driver with low noise to reduce laser relative intensity noise (RIN). In cases where it is desirable to shape the gain or output spectrum as a function of time, the current to a gain material can be changed in synchronization with the sweep. In this case, it is desirable that the current driver have high bandwidth to support dynamic shaping of the spectral envelope up to the highest sweep repetition rate of the instrument.

The desired envelope shape depends on the OCT imaging or measurement application. One preferred embodiment of the present invention adjusts the output current of the current driver as a function of time to spectrally shape the output emission to reduce OCT point spread function sidelobes. The absorption of light depends on the sample properties. For example, the water in the vitreous of the eye absorbs light as a function of wavelength. To maintain fine axial resolution, it can be desirable to pre-shape the output spectrum of the light from the sample arm to compensate for properties of the sample such that the light returning from the sample has the desired spectral composition for OCT axial resolution and OCT points spread function sidelobe performance. One preferred embodiment of the present invention adjusts the output current of the current driver as a function of time to spectrally shape the output emission to compensate for optical properties of the sample. Another preferred embodiment of the present invention adjusts the output current of the current driver as a function of time to spectrally shape the output emission to optimize light exposure to the sample when there are light exposure limits.

When both the forwards and backwards sweeps are used for imaging, the spectral envelope for the forwards and backwards sweeps can both be optimized independently. One preferred embodiment of the present invention uses both the forwards and backwards sweeps for imaging with the spectral envelope optimized for each sweep direction independently. When only either the forwards or backwards sweep is used for imaging, it can be advantageous that the output current of the current driver be adjusted as a function of time to blank out either the forwards or backwards sweep of the tunable source. Blanking out the forwards or backwards sweep for unidirectional sweep imaging can reduce accumulated or average light exposure to the sample, allowing power to be concentrated in the active portion of the sweep. One preferred embodiment of the present invention images with a sweep or a portion of a sweep blanked. Another preferred embodiment of the present invention images with a sweep or a portion of a sweep blanked to reduce light exposure to the specimen. One preferred embodiment of the present invention operates with only the forwards sweep used for imaging. Another preferred embodiment of the present invention operates with only the backwards sweep used for imaging. When light exposure to the sample is not of a concern, it is not necessary to blank an unused sweep. If the spectral envelope of the output of the tunable source is satisfactory when the current driver is driven at a constant current, it is not necessary to perform spectral shaping through current control. One preferred embodiment of the current invention operates the current driver such that the output current of the current driver is predominately fixed in time.

Figure 29:
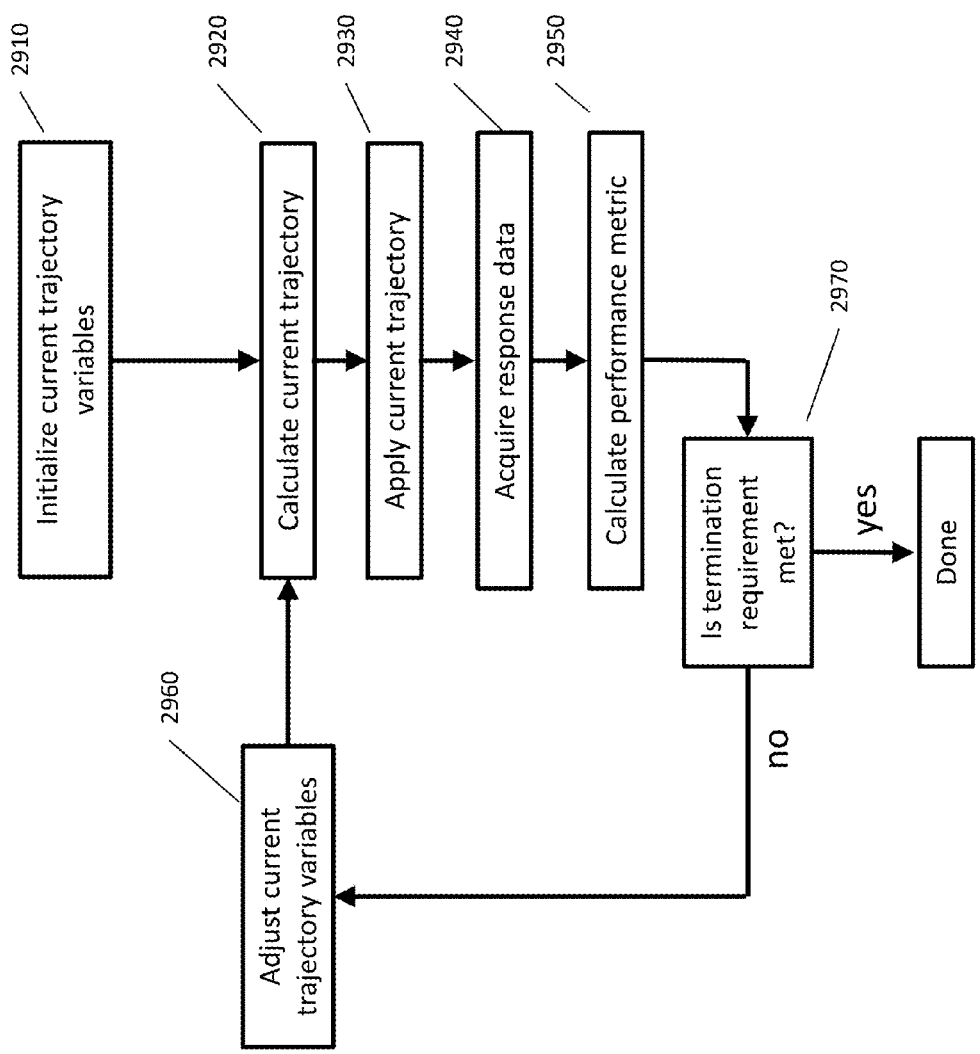
FIG. 29 is a flow chart illustrating a method of current driver waveform synthesis.

The preferred embodiment of the present invention automatically determines a current profile to the current driver based on a measurement of the output emission of the tunable source. The output measurement can come from the monitor portion of the current invention. The adjustment can be made by a controller that takes the monitor signal as input and uses the information in the monitor signal to adjust the waveform. The controller can be a processor, FPGA, microcontroller, analog circuit or other electronic circuit that can compute a proper correction. The controller can be embedded in the current driver or can be an external computational unit. The controller can also be a computer or processing unit connected to the OCT imaging system. FIG. 29 shows a diagram of a method for automatically determining an appropriate current profile. A current profile is defined with respect to adjustable input parameters. The input parameters are initialized 2910. The initialization values of the input parameters can be based on previous experience, a best guess, all constants of the same value, or all zeros. Other initialization values are possible, but it is generally preferable to choose a set of initialization values that are close to a solution to reduce time for optimization. An optimization algorithm adjusts the values of the input parameters 2960, a current trajectory is calculated 2920, the current trajectory is applied to the experimental apparatus 2930, and a response is acquired 2940. A performance metric is then calculated on the experimental response 2950. If a termination requirement is met, then the optimization stops 2970. If a termination criterion is not met, then the optimization proceeds 2960.

If the bandwidth of the current driver is sufficiently fast compared to the desired sweep envelope trajectory, then the dynamics of the current driver can be ignored and the optimization simplified. In one preferred embodiment, the current drive waveform is parameterized as a series of sample points. Each sample point is the input to a D/A converter connected to the current driver, where the waveform is represented as a vector of sample points, $\vec{d}$, and implemented as an array in computer memory. The waveform is applied to the experimental apparatus and the response recorded. In one preferred embodiment, the envelope of the fringe is determined from a Hilbert transform applied an MZI fringe. In another preferred embodiment, the envelope of the fringe is determined from a wavelength sensor, such as that shown in FIG. 28, where the power of the fringe as a function of time is determined by summing the appropriately scaled two detector measurements. Other methods of determining the envelope are included in the current invention. Given a desired fringe envelope vector, $\vec{h}_{des}$, and an experimental fringe envelope $\vec{h}_{exp}$, an error vector can be calculated as $\vec{e}_{env} = \vec{h}_{exp} - \vec{h}_{des}$. If the sampling rate of the drive waveform D/A and the sensor A/D are the same, then the update to the vector of sample points can be calculated on iteration, i, using a gain, α, on the error as $$\vec{d}_{i+1} = \vec{d}_i - \alpha \vec{e}_{env}.$$

A large gain, α, results in rapid and large updates of the drive waveform trajectory on each iteration, but can cause oscillations near the solution. A smaller gain value results in slower initial convergence, but prevents oscillations around the solution. If the dynamics of the current driver are significant, then the phase delay associated with the current driver dynamics can be included in the update by shifting the error vector in time as a function of frequency content. Other waveform parameterizations and optimization algorithms, such as those described for drive waveform synthesis are included in the current invention.

Figure 30:
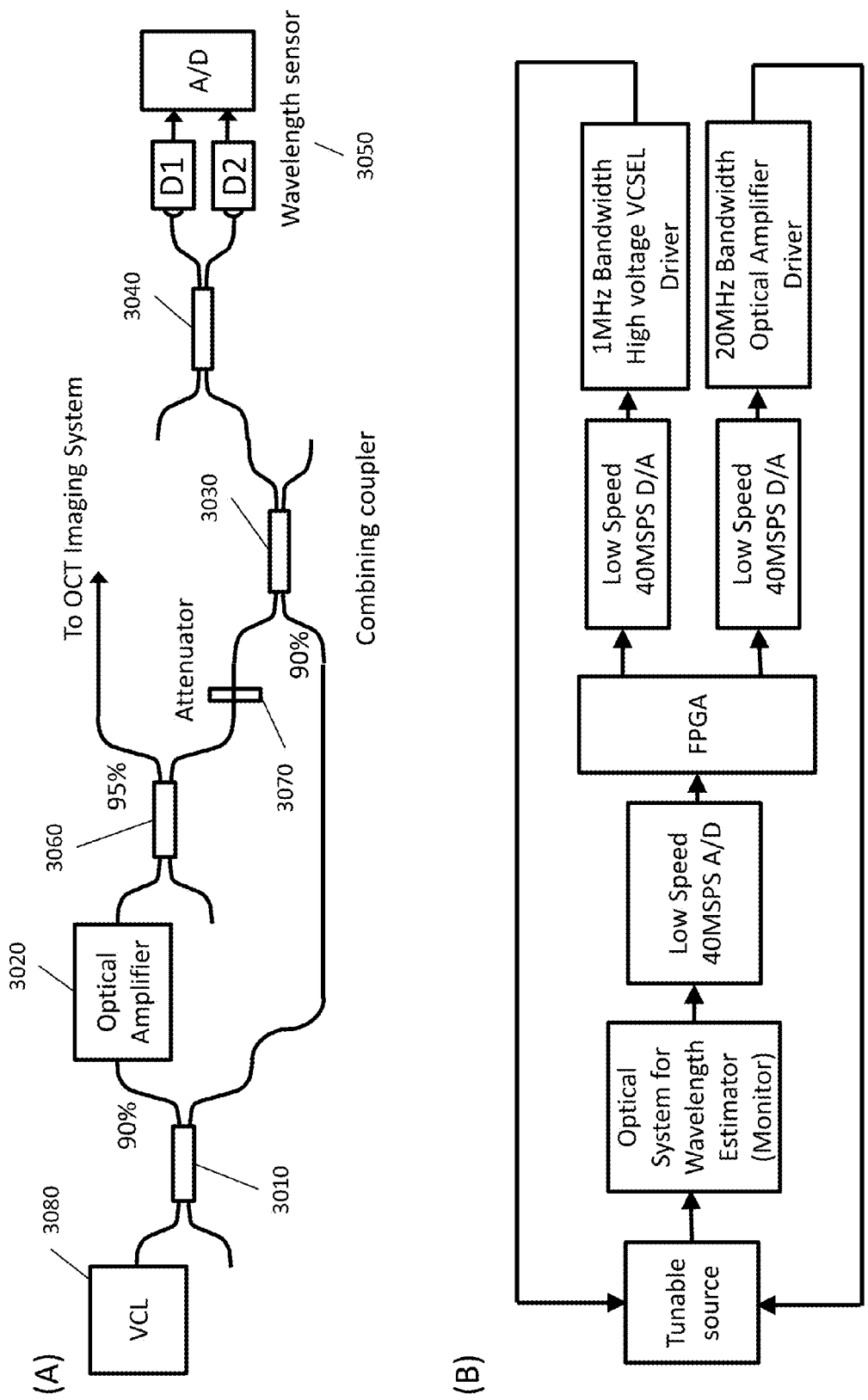
FIG. 30 is a set of drawings illustrating wavelength sweep measurement with feedback for wavelength sweep and envelope control.

It is possible to use a single wavelength sensor to measure properties of the VCL output and of the amplified output, as illustrated in FIG. 30A. A coupler 3010 with high power splitting ratio directs the majority of light from a VCL 3080 to an optical amplifier 3020. The remaining portion of the light from the VCL 3080 to be used for diagnostics is directed to a combining coupler 3030, which is in turn connected to a coupler 3040 that is used in the wavelength sensor 3050. Similarly, a coupler 3060 connected to the output of the optical amplifier 3020 directs the majority of light to the OCT imaging system. The remaining portion of light is directed to the other input of the combiner 3030. An optional attenuator 3070 can be used to approximately match the power from the VCL 3080 and from the optical amplifier 3020 to the detectors. When the current driver is turned off, the optical amplifier does not contribute to the sensor measurement and the output of the VCL is measured directly. The measurement can provide information about the sweep trajectory and the output power vs. time of the VCL. Knowledge of the sweep trajectory and power vs. time allows calculation of the power vs. wavelength of the VCL emission. The time history of the measurements from detector D1 and detector D2 are recorded with only the VCL active and stored in memory. When the optical amplifier is turned on, the sensor measures the combined output of the VCL and the optical amplifier. The time history of the combined VCL plus optical amplifier can be recorded. By subtracting the time history of the measurements that were previously stored for just the VCL from the combined VCL plus optical amplifier measurements, the contribution of the amplifier output can be determined. The information about power vs. time and wavelength vs. time of the amplified output allows the fringe envelope to be estimated. One preferred embodiment of the present invention uses information obtained from the wavelength sensor to calculate a sweep trajectory for use in the drive waveform optimization. One preferred embodiment of the present invention uses information obtained from the wavelength sensor to calculate the fringe envelope profile for use in the current driver waveform optimization. The information obtained from the wavelength sensor can also be used for diagnostic purposes to detect change in the VCL or amplifier. FIG. 30B illustrates how the wavelength sensor can be connected to an FPGA with relatively low speed A/D and D/A capability to implement drive waveform trajectory and current driver waveform trajectory optimization. FIG. 30B shows an FPGA used as the computation unit, but any one of many processors or controllers that can execute an optimization algorithm can be used.

OCT Imaging System and Imaging Modalities

Light from the tunable source 3110 is directed to the monitoring module 3120 and OCT imaging interferometer

Figure 31:
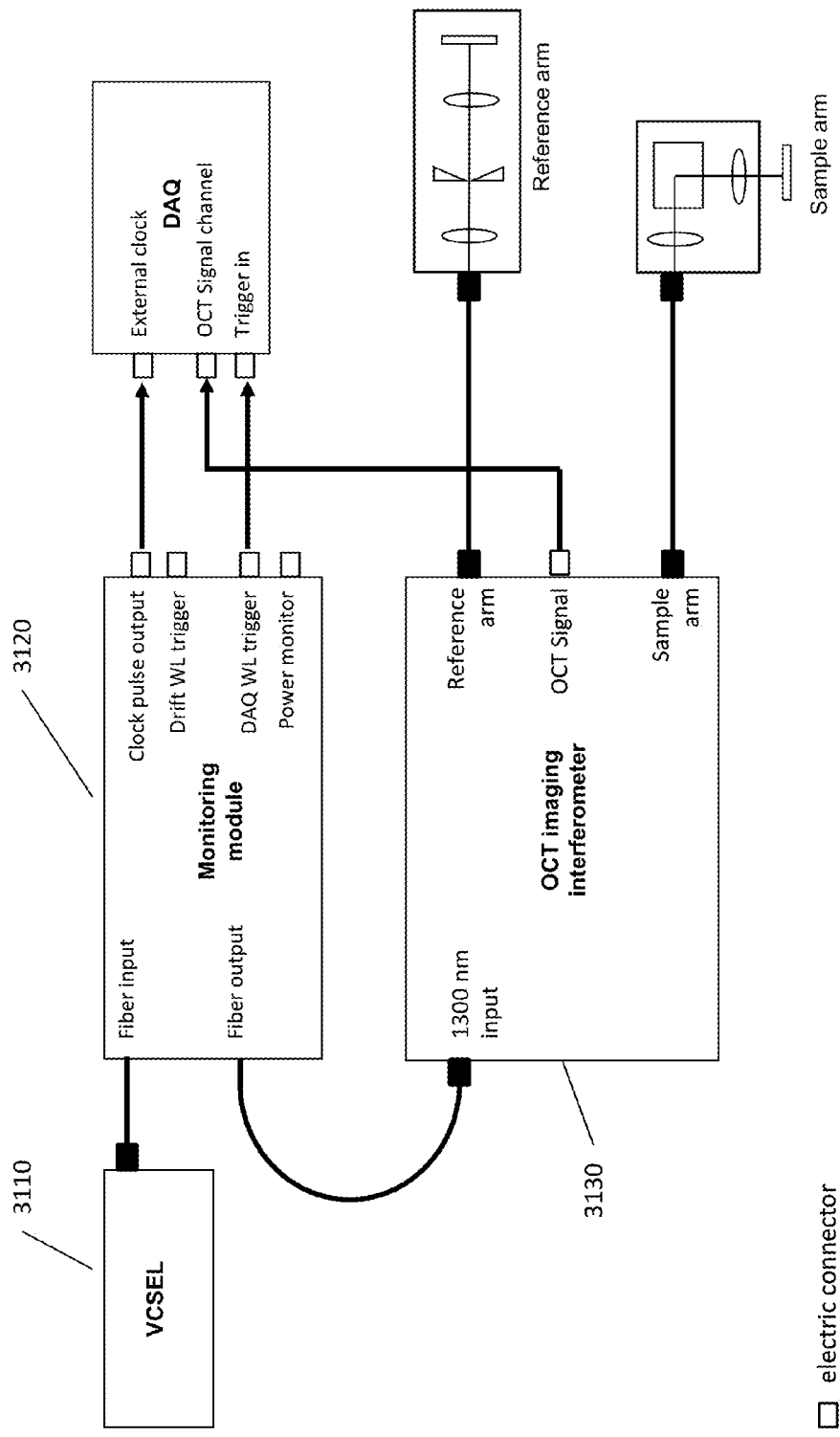
FIG. 31 is a block diagram of an OCT imaging system showing optical and electrical interconnections.
Figure 32:
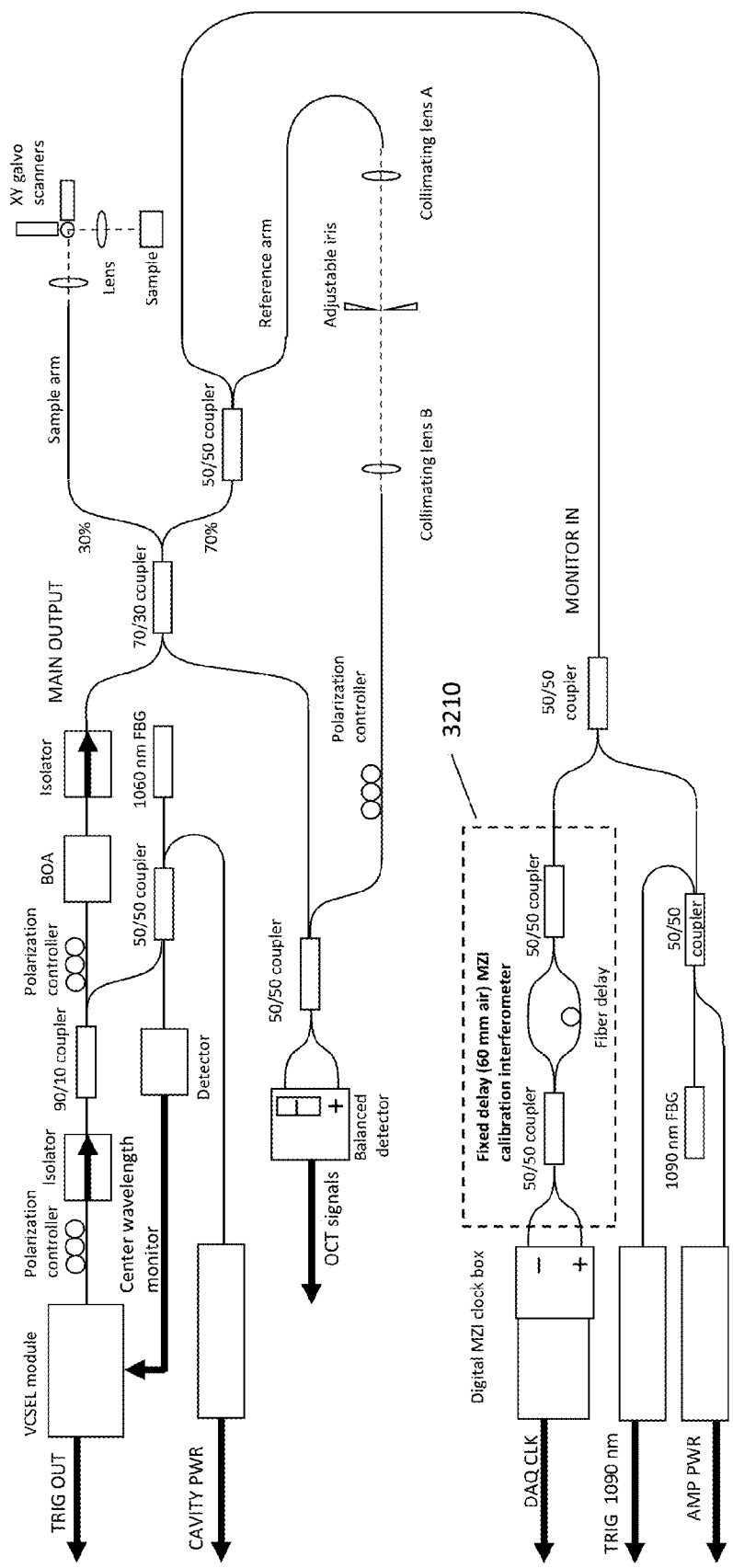
FIG. 32 is a block diagram of an OCT imaging system showing details of an imaging system that uses an optical path delayed reference arm, optical clocking, and an optical wavelength trigger.

3130, as illustrated in FIG. 31. In this particular embodiment, optical clock generation and sweep triggering are integrated into the monitoring module. The preferred interferometer design depends on the operating wavelength, cost constraints, and specific OCT imaging application. One common configuration used for OCT imaging is an interferometer of the Michelson configuration. FIG. 2 illustrates two example interferometer designs, although very many alternative interferometer designs and implementations are possible. Illustrated in FIG. 2A, a first preferred embodiment for the interferometer design uses fiber optic couplers with a first coupler 210 splitting light from the wavelength swept light source into a fiber path to the sample arm 250 and a fiber path to the reference arm 260. Light returning from the sample arm 250 returns through the first coupler 210 to a second coupler 240, the second coupler also receiving light from the reference arm 260. The light interferes at the second coupler and is directed to a balanced detector 270 to acquire the interference pattern. The interference pattern or interferogram contains the depth encoded reflectivity information from the sample. If there are no limits to light exposure levels on the sample, it is desirable to use a first coupler with a 50% (50:50) splitting ratio to optimize the OCT imaging instrument sensitivity. If there are light exposure limits on the sample and available swept source power, increases in collection efficiency and associated OCT instrument sensitivity can be obtained by using a first coupler with unequal splitting ratio. One preferred embodiment of the present invention uses an interferometer that includes a fiber coupler with splitting ratio larger than 60:40 to improve efficiency, the higher ratio path connecting the sample arm to the second coupler. Light from the sample is thus preferentially directed to the detector, with light corresponding to the low ratio side being directed back to the source and lost with respect to detection. The spitting ratio of the second coupler connected to the detector is preferentially near 50:50 and the response is wavelength flattened over the range of operating wavelengths to cancel RIN and balance the background signal. An interferometer of this basic design works well for all wavelengths. A detailed illustration of an interferometer design of this configuration designed to operate at 1050 nm wavelengths is shown in FIG. 32.

At certain wavelengths, such as 1310 nm, circulators have very high efficiency. It this therefore preferable to use an interferometer with circulators 220, 230 to improved light collection efficiency to the detector, as shown in FIG. 2B. One preferred embodiment of the present invention uses an interferometer that includes one or more circulators to improve efficiency. A detailed illustration of an interferometer design of a configuration using circulators and designed to operate at 1310 nm wavelengths is shown in FIG. 33. Other designs using circulators are also possible.

In the present invention, the interferometer can be constructed in many different configurations beyond those shown. However, any configuration of interferometer that interferes light from a reference arm and sample arm is included in the present invention. The reference arm of the interferometer generates an optical path delay in the interferometer. In one preferred embodiment, the reference arm contains a mirror to generate a reference optical path length. In another preferred embodiment, the reference arm contains a fiber loop to generate a reference optical path length. In another preferred embodiment, a common path interferometer design in which the sample arm light and reference arm light share a common optical path is used to generate the reference arm signal. The sample arm can act as the reference arm in the case when a reference reflection is obtained by a reflective surface located along the sample arm. When the sample arm and reference arm share a common path, the reflective surface can also be located outside the sample arm, for example by using a glass coverslip or window touching or near the sample being imaged. In another preferred embodiment, the reference arm contains an air path to generate a reference optical path length. One preferred embodiment of the present invention includes a reference arm in which the reference arm optical path delay or optical path length is adjustable. Examples of ways to adjust the optical path length are to move a reference mirror, to change the distance between collimators, to include a length of fiber, to change an index of refraction, or any other method to change an optical path length. OCT interferometers of the present invention can be built with bulk optics interferometers or fiber optic interferometers or a combination of both bulk optics components and fiber optic components.

OCT interferometer designs according to some embodiments of the present invention will direct the interfered light to one or more optical detectors that convert the optical interference fringe signals from the optical interferometer into electric analog signals. The detectors commonly include photodiodes and a transimpedance amplifier to convert current from the photodiodes to voltage. The analog signals from the OCT system contain the inteferometrically encoded information about the reflectivity vs. depth of the sample at a point of interrogation. The high sweep speeds and long imaging range of the current invention generate high frequency interferometric fringes. Detectors with high bandwidth, low noise, and high gain are desirable to realize the imaging potential of the instrument. The gain should be high enough to overcome digitization noise. One preferred embodiment of the present invention uses at least one optical detector that has greater than 1 GHz bandwidth to support high sweep repetition rate, wide wavelength sweep, and long imaging range applications. The imaging system is flexible and can operate at more traditional OCT imaging speeds and imaging ranges. A preferred embodiment of the present invention for low cost uses at least one optical detector that has greater than 10 MHz bandwidth. A balanced detector and interferometer design can be used to suppress random intensity noise (RIN) from the source for improved signal to noise. Balanced detection can also reduce the low frequency background that results from wavelength dependence in fiber couplers and other beam splitters or combiners. Reducing the background enables better utilization of the A/D converter dynamic range. A preferred embodiment of the present invention uses at least one optical detector that performs balanced detection. Excess detector bandwidth can also be problematic as the high frequency noise is aliased into the measurement. The detector bandwidth should be chosen to match the A/D digitization rate maximum supported Nyquist defined digitization bandwidth.

A data acquisition device is used to convert the electric analog signals output from the one or more detectors into digital data. This digital data stream contains the encoded depth dependent reflectivity information from the sample. The digital data stream can be stored or processed by a processing unit, which could be a computer, CPU, Microcontroller, Digital Signal Processor (DSP), FPGA, or other device capable of processing digital data. Many swept source OCT systems use an interferometer to generate a clock signal for the A/D converter, called optical clocking or k-clocking. The same advantages of balanced detection previously mentioned for the OCT data channel also apply to the clocking module. A preferred embodiment of the present invention uses a clocking interferometer 3310 and clocking detector 3320 that implement balanced detection.

There is often a beam steering element in the sample arm to facilitate scanning the light beam. A preferred embodiment of the present invention includes imaging systems in which the sample arm comprises at least one scanning mirror or other beam steering element to steer the sample arm light beam.

The most common implementation of OCT acquires information about the magnitude of backscattered or back-reflected light and is often called intensity OCT imaging. OCT imaging can also use information encoded in the phase of the OCT fringe, called phase sensitive OCT. Doppler OCT uses phase information from two or more A-scans to determine the axial component of the velocity of scatterers in a fluid flow. Polarization sensitive OCT can also be performed in which information about the birefringent properties of the sample are obtained. Polarization sensitive OCT is often implemented by using two detectors and a polarization sensitive beam splitter in the interferometer. Some, but not all, variations on polarization sensitive OCT illuminate the sample with light of different polarization state. The polarization state can be encoded in alternating sweeps of the laser source. One embodiment of the present invention performs phase sensitive OCT. Another embodiment of the present invention performs Doppler OCT. Another embodiment of the present invention performs polarization sensitive OCT.

The long coherence length of the VCL source enables a long imaging range. However, the imaging range is still governed by the depth of field of the optics in the sample arm. One preferred embodiment of the present invention comprises an axicon lens or similar element in the sample arm to increase the useful imaging range of the optical imaging system. It is also possible to implement dynamic focusing by using one or more actuated optical elements. Another preferred embodiment of the current invention includes an actuated adjustable focusing means.

Adaptable Fringe Calibration

In OCT imaging, the cavity of the laser is often swept as a natural function of wavelength because the cavity length defines the tuning wavelength. Further, actuator dynamics, acceleration limits, and resonant modes may influence the shape of the sweep trajectory and cause sweep-to-sweep variation. In OCT imaging, the interferometric data must be linearized with respect to wavenumber such that the sample points are spaced at equal k (wavenumber) intervals before Fourier transforming to obtain the depth dependent reflectivity information from the sample. An auxiliary MZI is often used to record a fringe encoding the sweep trajectory. It is common that a numerical calibration step be applied to the OCT fringe data before Fourier transforming when the data is acquired at a fixed sampling rate. This numerical calibration step is computationally expensive. One embodiment of the present invention acquires a single reference OCT fringe, determines the proper calibration, and applies the correction for this single calibration to the OCT data acquired from the sample. The application of the correction is performed by interpolating the fringe into equal k intervals from a phase evolution calibration curve. The phase evolution calibration curve can be determined by analyzing fringe zero crossing spacing or by determining the phase from a Hilbert transform, as is common in OCT processing. An alternative approach acquires the data at a non-uniform sampling rate such that the data is precisely sampled at equal wavenumber intervals. One method for acquiring the data in this pre-calibrated manner is to clock the A/D converter with a signal from a clocking interferometer. This method of optically clocking, sometimes referred to as k-clocking, has an additional benefit of optimizing the data acquisition so as to not oversample slow regions of the sweep, resulting in a data reduction and more efficient data storage, transmission, and processing. The optical clocking methods also account for sweep-to-sweep variation. One preferred embodiment of the present invention uses an optical clocking module comprising a clocking interferometer and clocking detector that generates an optical clock signal used to clock the data acquisition device. There are a large number of possible clocking interferometers that can be used in the present invention. Two common interferometer configurations are the Michelson and Mach-Zehnder type. All of the potential interferometer configurations are included in the present invention.

During operation of the OCT imaging system of an embodiment of the present invention, the sweep repetition rate, sweep trajectory, and sweep range may be adjusted. If the rate of change of wavenumber for the different operating modes is significantly different, then a calibration interferometer of fixed optical path delay may not be suitable for all operating modes. If the optical path delay is too short for an operating mode, the fringe frequency and fringe density will be too low to obtain a good calibration if software calibration techniques are used. Similarly, if optical clocking methods are used, an optical path delay that is too short will result in a low sampling rate of the A/D converter that unnecessarily compromises OCT imaging range. If the optical path delay is too long for an operating mode, then fringe frequency and fringe density will be too high and may exceed detector and A/D bandwidth for software calibration techniques. Similarly, if optical clocking methods are used, an optical path delay that is too long will generate A/D clock signals that exceed the capability of the A/D converter.

Figure 34:
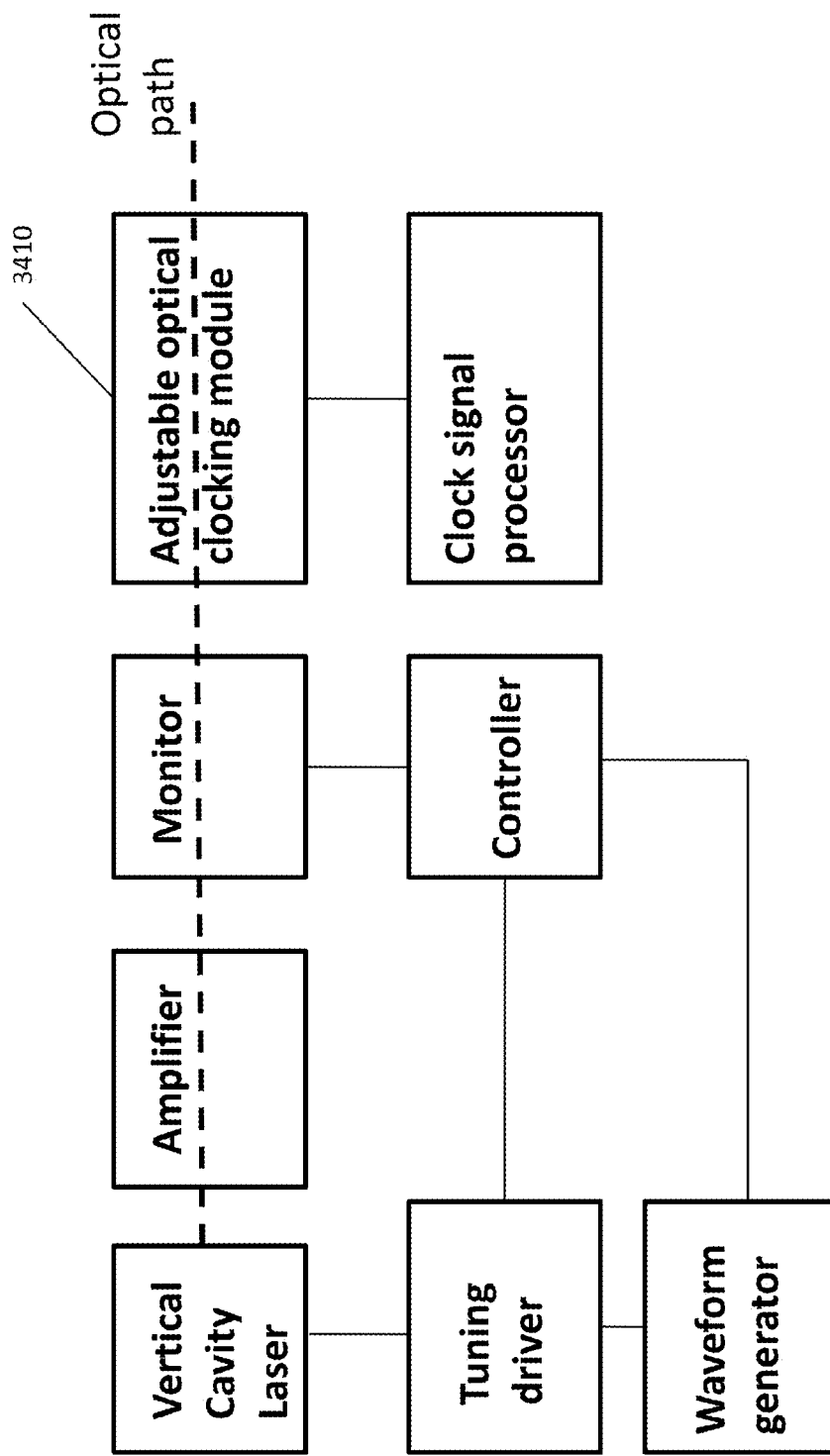
FIG. 34 is a block diagram of a tunable source with adjustable optical clocking module.

To address the limitations of a traditional fixed path length calibration interferometer, the preferred embodiment of the present invention uses an adjustable optical clocking module 3410, as shown in FIG. 34. There are many possible ways the output of the adjustable optical clocking module can be tailored to the desired imaging mode.

Figure 35:
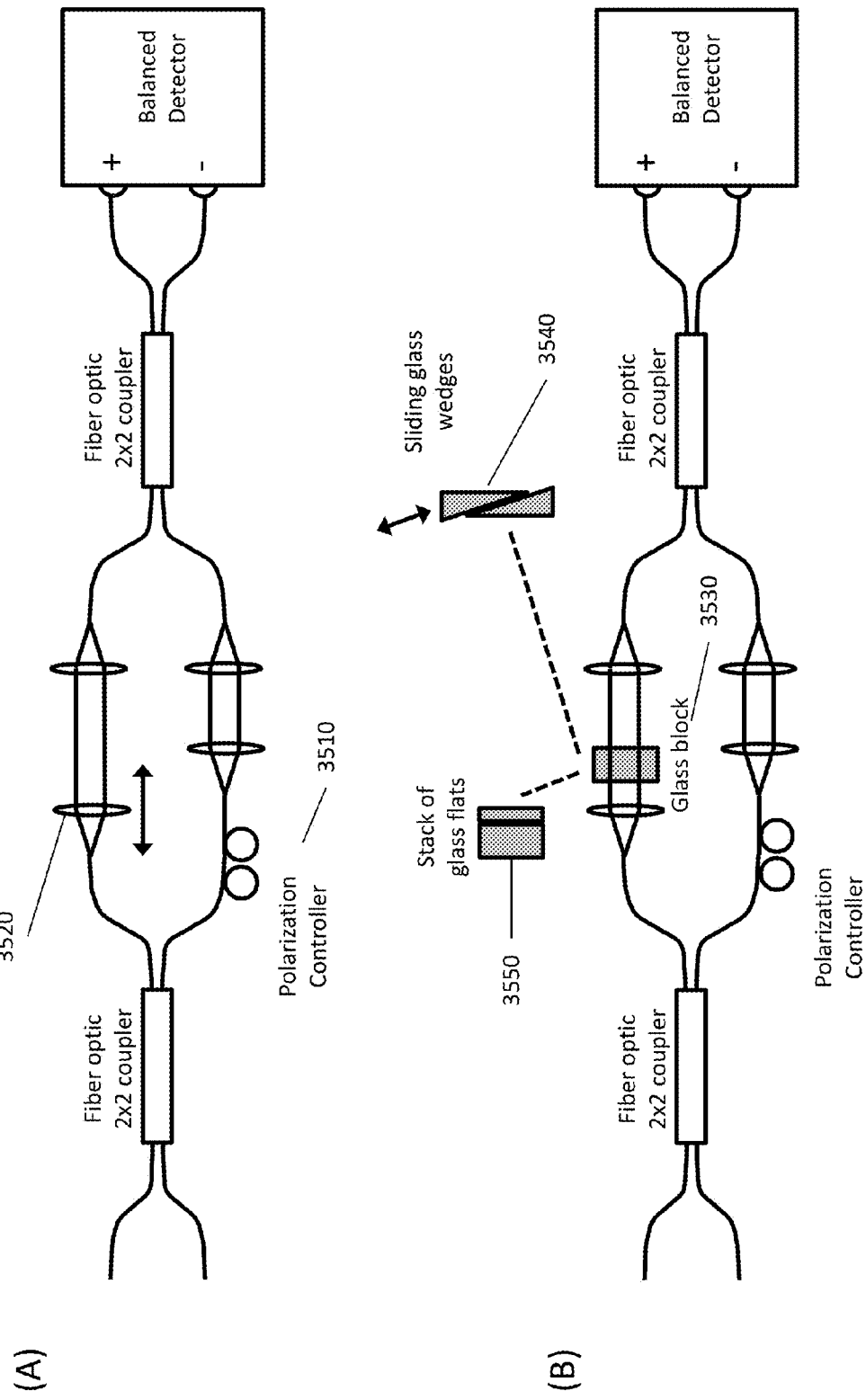
FIG. 35 is a set of drawings illustrating an adjustable path length interferometer and dispersion compensation.

FIG. 35A illustrates a dispersion balanced fiber optic MZI for generating an optical clock or a reference fringe for software calibration. A polarization controller 3510 is included to facilitate alignment of the polarization state between the two arms to maximize the fringe amplitude. With adjustments to the sweep trajectory, the frequency of the clock signal from a clocking interferometer may change accordingly. To accommodate these changes and ensure that the clocking frequency stays within the bandwidth limitations of the acquisition device, the optical path length of the clocking interferometer can be changed. One preferred embodiment of the present invention uses an optical clocking module that supports different sweep trajectories by adjusting the optical path delay of the interferometer. In FIG. 35A, the optical path difference in the interferometer can be adjusted by moving one or more collimators 3520. The movement can be actuated or under manual user control or selection. It is often difficult to match fiber lengths perfectly to obtain adequate dispersion balance between the two interferometer arms to generate a fringe with equally spaced k intervals. FIG. 35B illustrates inserting dispersion compensation glass in one arm of the optical interferometer. Glass blocks 3530, glass prisms, optical flats, stacks of glass blocks 3550, or sliding glass wedges 3540 with adjustability of path length can be used as the dispersion compensating medium. One drawback of the approach illustrated in FIG.

Figure 36:
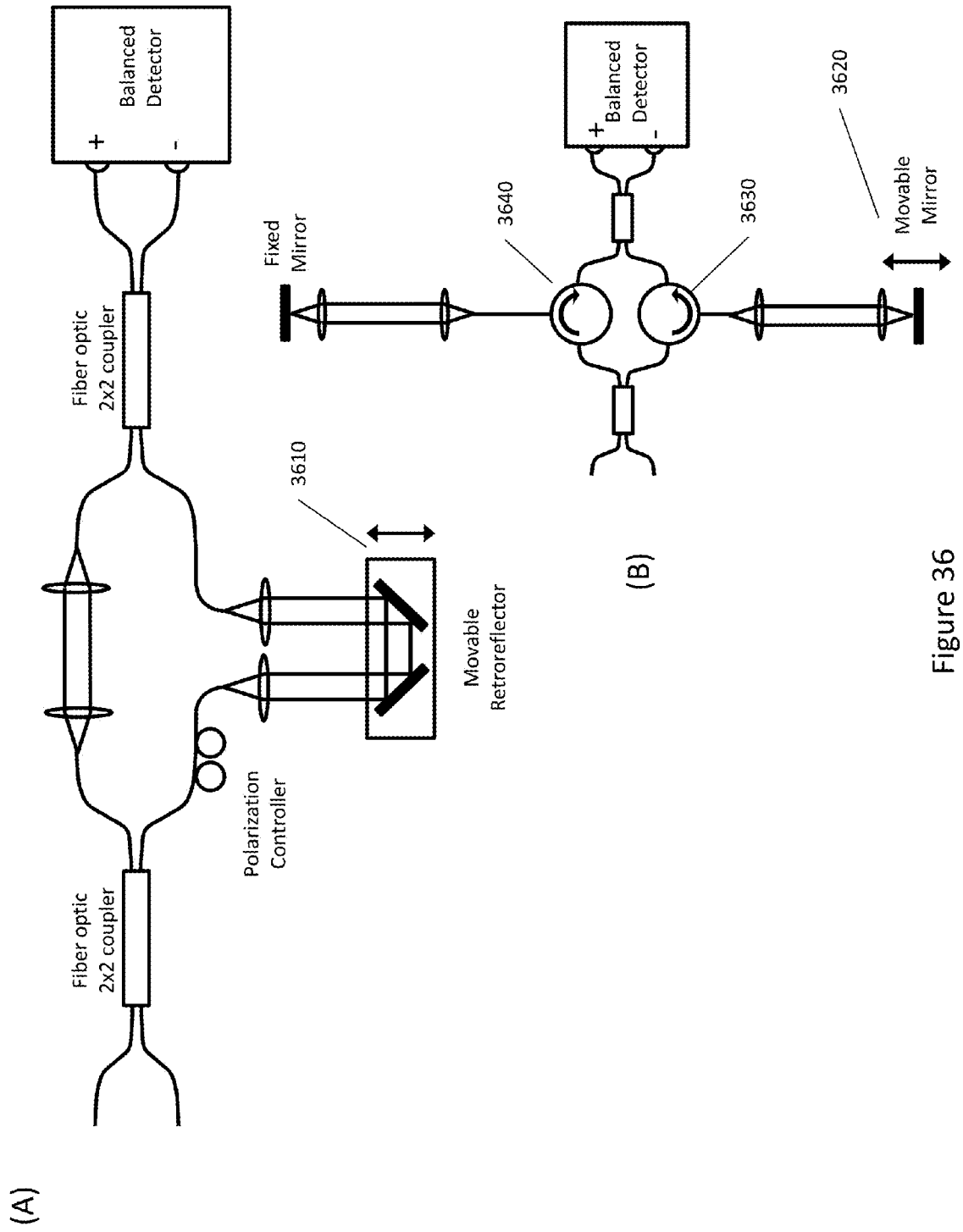
FIG. 36 is a set of drawings illustrating adjustable path length interferometers with a retroreflector and with circulators.

35A is that movement of the collimator can result in a disturbance to the fiber, which can cause a change in the birefringent behavior and decrease fringe amplitude through a polarization mismatch between the two interferometer arms. FIG. 36A shows an improved design that includes a movable retroreflector 3610 and FIG. 36B shows an improved design that uses a movable mirror 3620 and circulators 3630, 3640 in the interferometer. In both of these designs, the mirror can be moved without disturbing the polarization alignment of the system.

Figure 37:
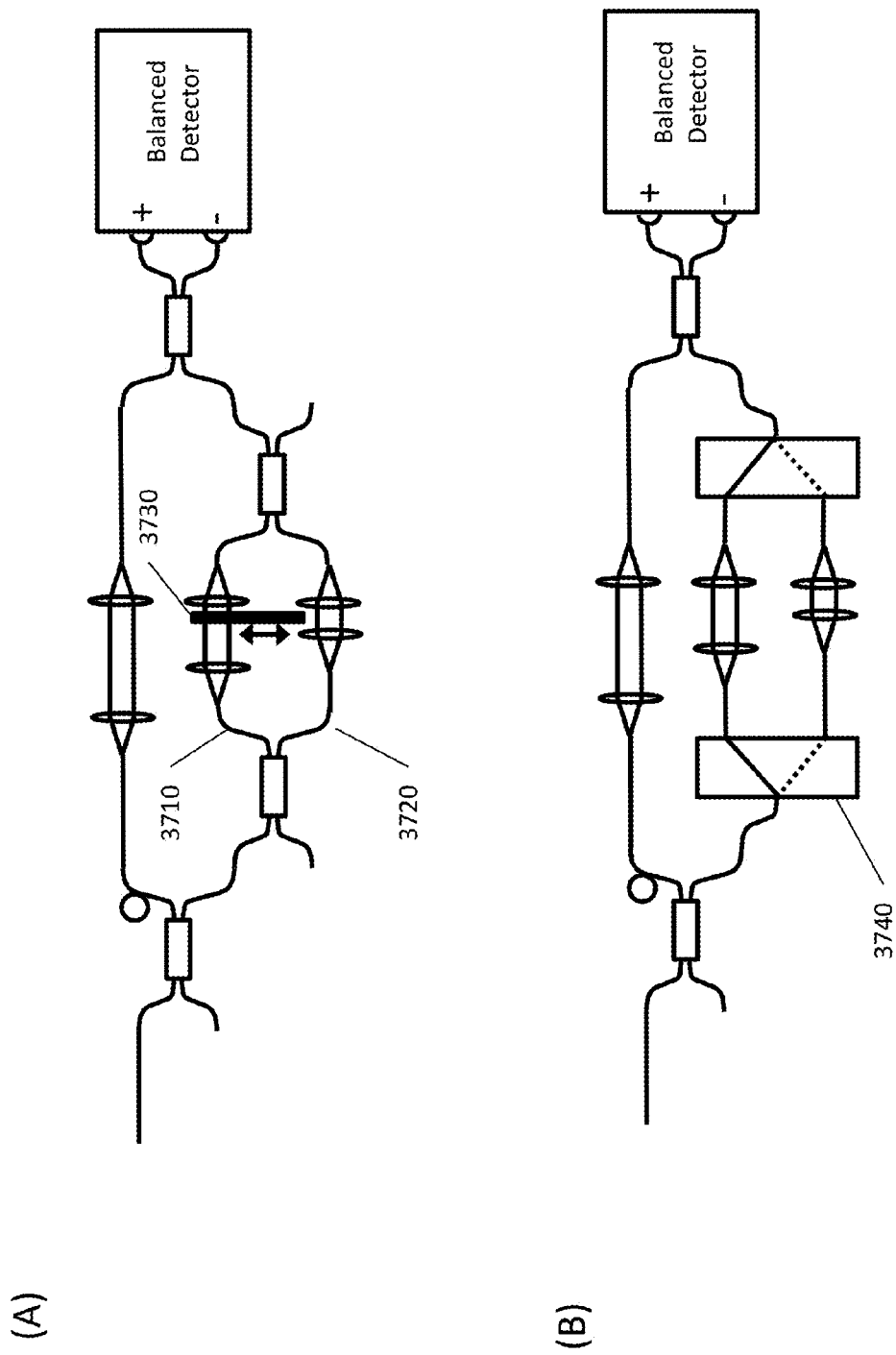
FIG. 37 is a set of drawings illustrating methods for selecting an optical path in one arm of the interferometer.

It is also possible to switch between multiple interferometer paths. FIG. 37 shows methods for switching between different length interferometer paths to adjust the interferometer path length difference. In FIG. 37A, multiple optical paths 3710, 3720 exist in one arm of the interferometer and a light blocking mechanism 3730 selects the path that is active. In FIG. 37B, an optical switch 3740 selects the active path from the multiple paths that are available. FIG. 37 shows selection from two paths. Selection from more than two paths is possible by expanding the interferometer network.

Figure 38:
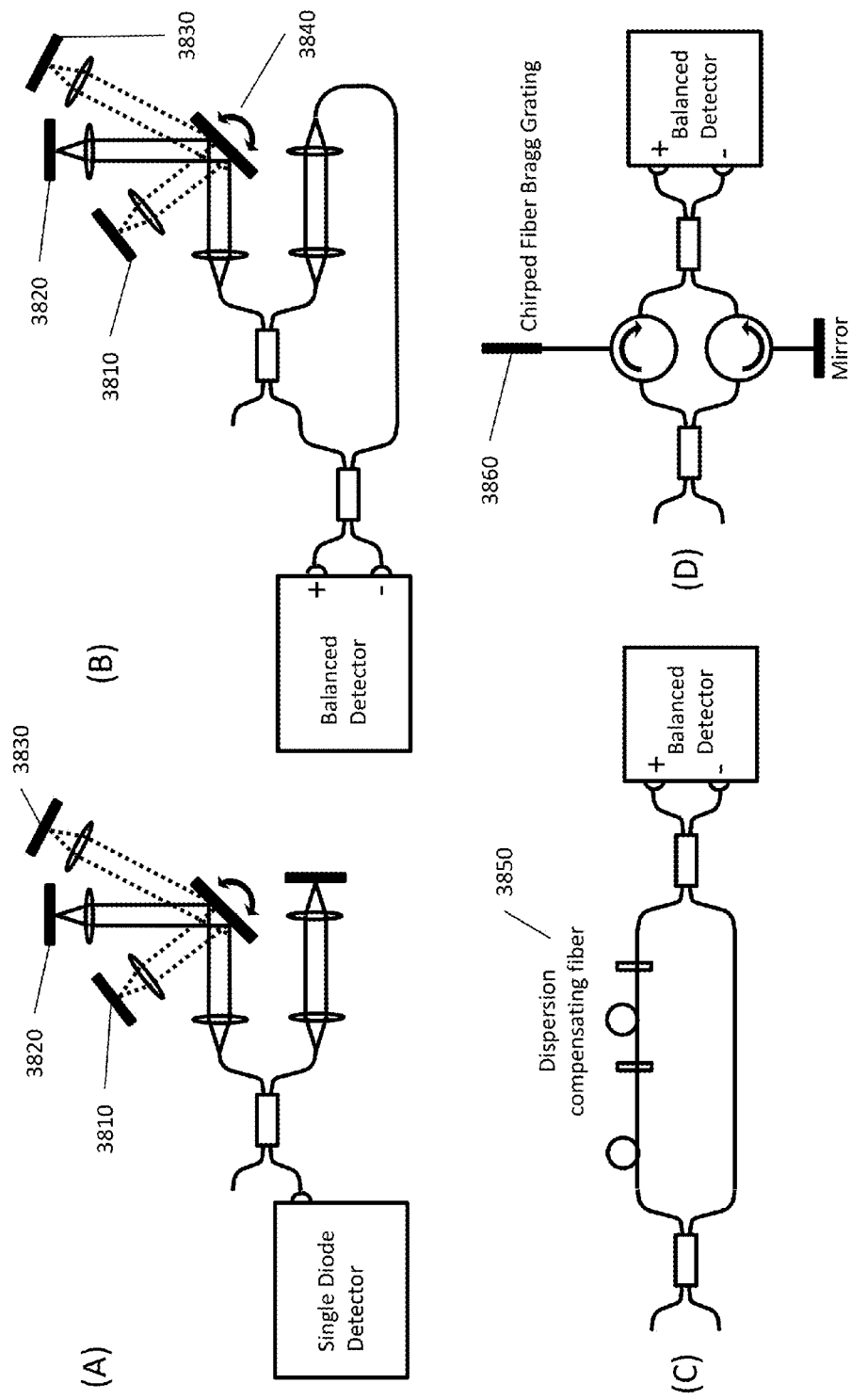
FIG. 38 is a set of drawings illustrating methods for selecting an optical path in one arm of the interferometer or for using dispersion compensation in the interferometer.

FIGS. 38A and 38B illustrate methods for changing the optical path length in one of the interferometer arms by directing the light from one arm to different mirror reflectors 3810, 3820, 3830 located at different optical path lengths. FIG. 38A uses an optical layout suitable for unbalanced detection and FIG. 38B shows an optical layout suitable for balanced detection. In these diagrams, a rotating mirror 3840 selects the optical path. The rotating mirror 3840 can be galvo driven, a MEMS mirror, or any other device for steering the light beam.

Using air spaced interferometer arms is one way to achieve dispersion balancing. All fiber interferometers have advantages in ease of alignment and assembly. FIG. 38C illustrates using dispersion compensating fiber 3850 to dispersion balance the two different length interferometer arms. FIG. 38D shows using a chirped fiber Bragg grating 3860 to implement dispersion compensation. FIG. 38D shows dispersion compensation using a single FBG. Multiple FBGs using circulators with additional ports are also included in the present invention. It is possible to combine an all fiber interferometer design that includes a means for dispersion compensation with any of the ideas presented in this application, including switching light paths, blocking light paths, or frequency multiplying or dividing of the interferometer signal.

Figure 39:
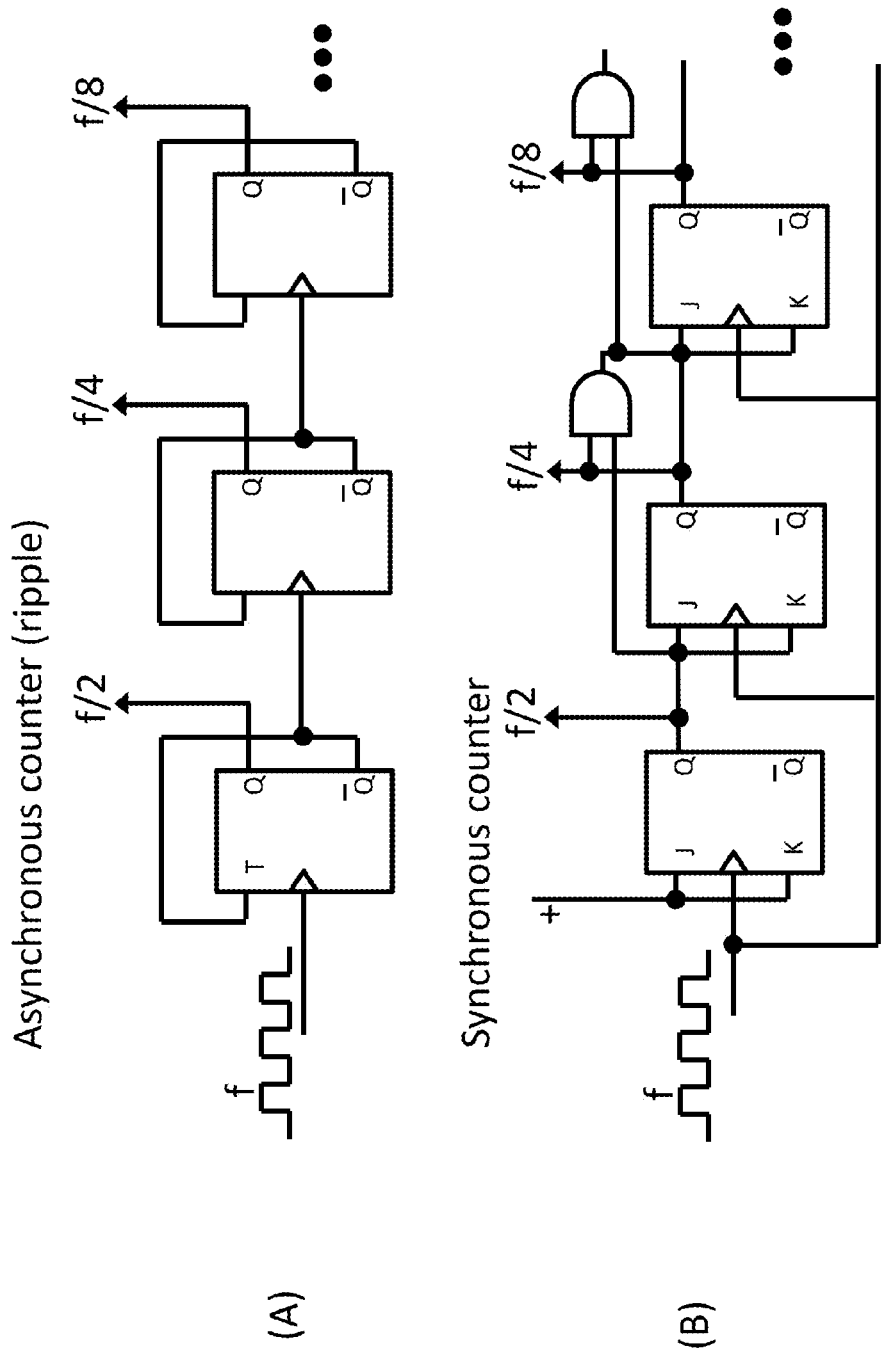
FIG. 39 is a set of electronic schematics showing counting logic.

The clocking interferometer may or may not be adjusted and it is possible that the clocking interferometer be fixed in path length difference. One significant advantage of the tunable VCL technology in an embodiment of the present invention is a long coherence length. This long coherence length of the source enables the generation of clean interferometric fringe cycles at long optical path length delays, much longer than previous technologies. The shorter coherence length of other tunable source technologies has prevented attempts at generating clean interferometric fringes at long optical path delays. Thus, many previous technologies have required electronic frequency doubling of the optical clocking signal to achieve adequate OCT imaging range. An embodiment of the present invention is capable of generating clean interferometric fringes for optical clocking at very long optical delays, which corresponds to high fringe frequencies. Thus, an embodiment of the present invention can perform optical clocking without requiring electronic frequency doubling. Further, the optical clocking frequency can be quite high. Regardless of ability to adjust path length, one preferred embodiment of the present invention uses a signal from the optical clocking module that can be reduced in frequency by frequency division or electrical counting to support different sweep trajectories of the tunable source. FIG. 39 illustrates electronic circuits for performing frequency division of a clock signal. FIG. 39A shows an asynchronous ripple counter that can divide the frequency input. However, the propagation delay associated with the ripple counter may cause a phase error if the wavelength sweep trajectory varies in sweep rate. FIG. 39B shows a preferred synchronous counting circuit that changes state on the edge transition of the clock input signal, making it more desirable for use in an OCT clocking application. The counting circuit can be constructed of individual logic elements, but is more preferably implemented using dedicated counting chips or other fast logic. The long coherence length of the VCL allows the fundamental clock frequency to be quite large and associated with a long path delay, making the frequency division approach practical. It is also possible to frequency multiply. One method of frequency multiplication filters out harmonics of the fundamental input clock signal. Another preferred embodiment uses a signal from the optical clocking module that can be increased in frequency by at least one frequency multiplier to support different sweep trajectories of the tunable source.

Figure 40:
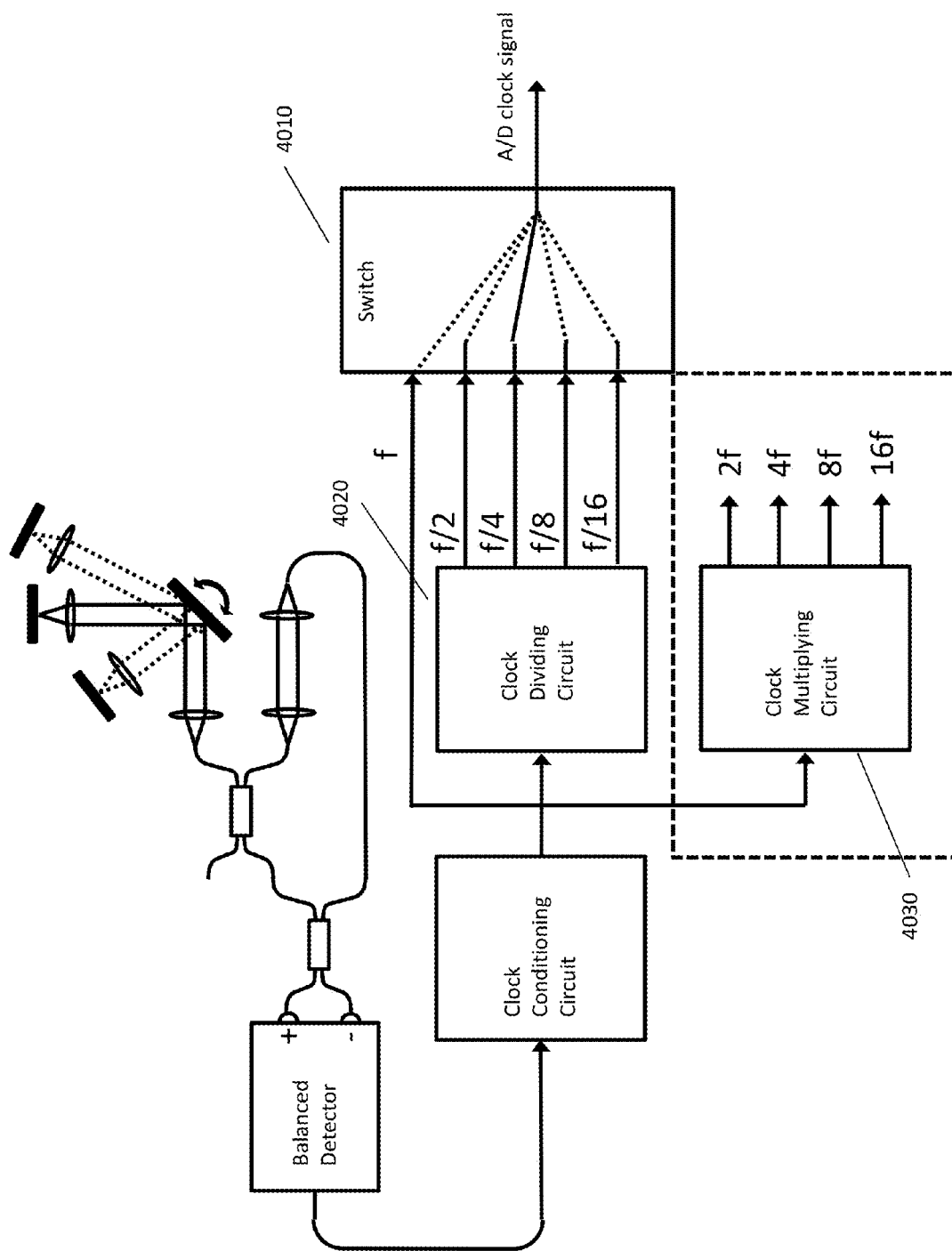
FIG. 40 is a drawing showing the combination of selecting the path length in an interferometer arm combined with frequency division and frequency multiplication.

FIG. 40 illustrates that it is possible to combine a method of optical path length change, selection, or switching 4010 with a clock dividing circuit 4020 and optional frequency multiplying circuit 4030 to achieve an expanded set of clocking frequency options. The frequency multiplier 4030 is shown as an optional component in this diagram because frequency division is a more robust approach for calibrating the fringe in the case of varying frequency as the filter center frequency of the multiplying circuit needs to track the fringe frequency.

One preferred embodiment of the present invention uses an optical clocking module comprising a Michelson or Mach-Zehnder interferometer with adjustable path delay to support variable measurement imaging ranges within the data acquisition bandwidth.

It is possible that the clocking interferometer not be dispersion matched. In this case, the optical clocking will be repeatable, but will not result in precise equal wavenumber spacing of data points. This implementation of optical clocking is still useful for reducing sweep-to-sweep variability and for reduced data storage, computation, and transmission requirements. FIGS. 32 and 33 both show an MZI calibration interferometer 3210, 3310 for this purpose. The MZIs 3210, 3310 in these diagrams is constructed of fixed lengths of fiber, which works at certain wavelengths and over relatively short wavelength sweeps. A dispersion balanced MZI would be preferred for operating at all wavelengths and over large sweep ranges.

Methods of dispersion control and optical dispersion matching can be used to achieve predominately equal sample spacing. Using an air spaced Mach-Zehnder interferometer with equal fiber and collimating lenses in each arm is one method of generating a dispersion free clock signal with equal wavenumber fringe spacing. One embodiment of the present invention comprises an optical clocking module that comprises a clocking interferometer and clocking detector that generates an optical clock signal to clock the data acquisition device. More specifically, one preferred embodiment of the present invention comprises an optical clocking module comprising a clocking interferometer and clocking detector that generates an optical clock signal to clock the data acquisition device at predominately equal or repeatable optical k-intervals (wavenumber intervals).

Adaptable Imaging Dynamic Range

Sensitivity in OCT is the "minimum detectable reflected optical power compared to an ideal reflector" and Dynamic Range is the "range of optical reflectivities observable within a single acquisition or image" as defined by J. A. Izatt and M. A. Choma, Section 2.7, W. Drexler and J. G. Fujimoto Ed., "Optical Coherence Tomography: Technology and Applications", 2008.

Sensitivity in OCT is generally quite good and approaches the shot noise limit, which is the theoretical best sensitivity that could be achieved given the detector responsivity, imaging speed, digitization rate, wavelength, power of light on the sample, and transmission efficiencies of the optics. High OCT sensitivity is achieved by maximizing power incident on the sample within limits for sample exposure and considering power available from the source. Typical sensitivities for OCT systems range from about 80 dB to 130 dB.

Figure 41:
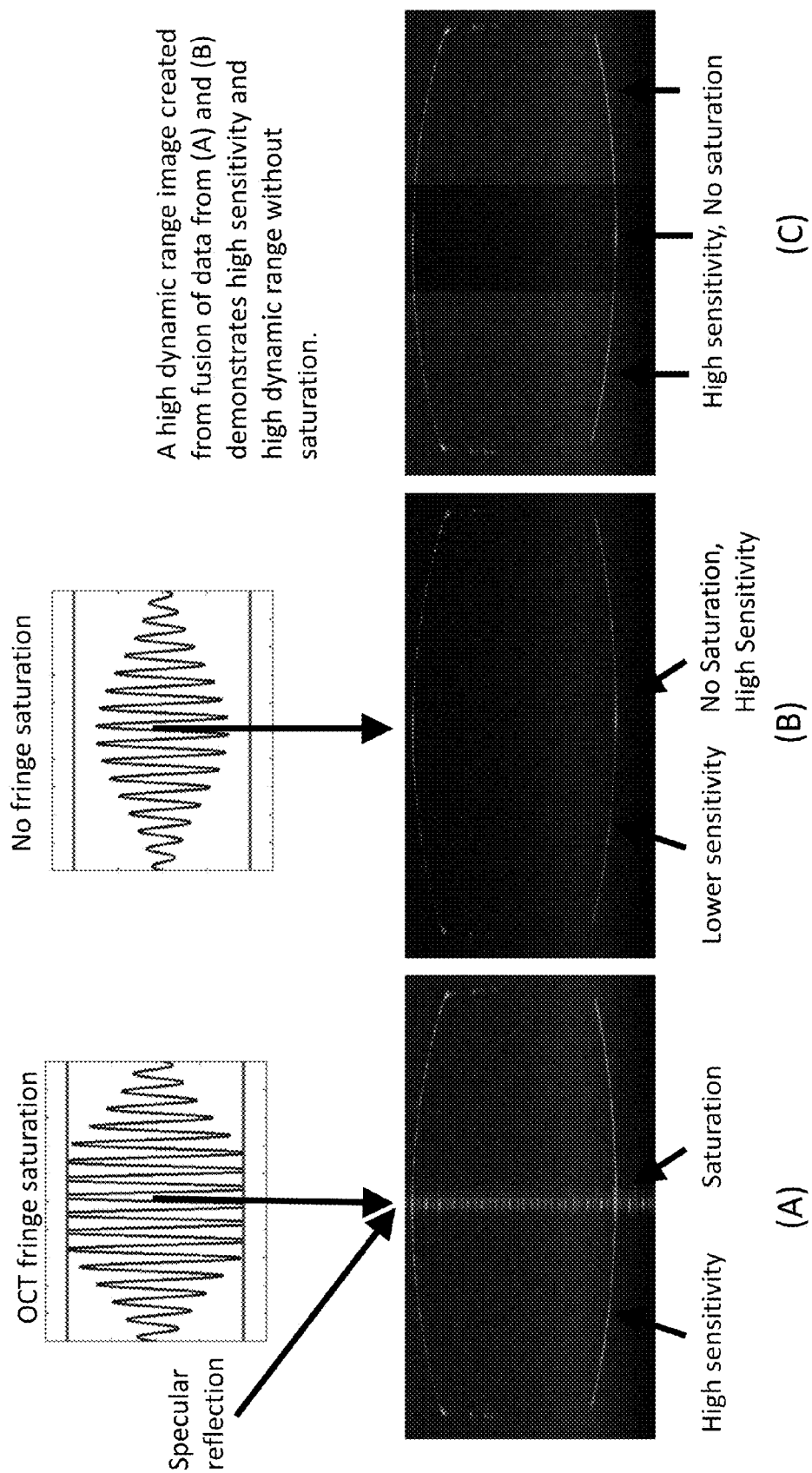
FIG. 41 is a set of OCT cross sectional images illustrating expanded dynamic range imaging.

Dynamic range in OCT is limited by digitization effects, A/D saturation, and detector dynamic range. Typical values of the dynamic range for OCT systems are from about 30 dB-60 dB. The limited dynamic range of OCT is often a problem when imaging biological samples with regions of high specular reflection. For example, large saturation artifacts are often observed in OCT images of the anterior eye where the cornea and lens have surfaces nearly normal to the OCT beam. The limited dynamic range can also be a problem when imaging through glass surfaces, such as coverslips, lenses, or windows that produce high specular reflection. Very large sample arm power can be used for metrology. High specular reflection or large return signal can also be a problem and generate saturation artifacts when imaging and measuring non-biological samples, such as manufactured parts. FIG. 41A illustrates the effect of saturation on an OCT image of a glass lens. Regions of high reflectivity, often occurring where there is specular reflection, generate a large OCT fringe that saturates the detection, as illustrated in the diagram of a fringe in FIG. 41A. It is possible to eliminate the saturation by reducing the output power of the swept source. FIG. 41B shows an illustrative example OCT cross sectional image of the same object scanned at a reduced power level that eliminates saturation. Data from FIGS. 41A and 41B can be fused to generate a composite cross sectional image with improved dynamic range that has high sensitivity to detect small return signals where there is no saturation and accepts high return signals without saturating the detection. One preferred embodiment of the present invention adjusts the output power of the tunable source to eliminate saturation in the detection. The output power of the tunable source can be controlled by adjusting the current in the current driver of the present invention. For example current to an optical amplifier or the VCL gain material could be adjusted. It is possible to detect saturation during an acquisition and rescan regions where saturation occurred by reacquiring data from a region of a data set a second time with reduced output power. Multiple rescans may be required to identify a saturation power that maximizes sensitivity and avoids saturation. This method works well for acquiring OCT data from a sample that changes or changes with time and there is no a priori knowledge about the reflectivity characteristics of the object. In industrial manufacturing and inspection applications, it is common to repetitively image objects of similar geometry and reflectivity properties. It is possible to learn the expected reflectivity properties of the sample as a function of the scanning trajectory. A suitable tunable source output power for each A-scan or regions of A-scans can then be executed such the object is imaged with proper power levels during a single acquisition without the need to revisit regions of the sample. In one preferred embodiment of the present invention, digital data is checked for saturation and the current to a gain material adjusted if saturation is found. In one preferred embodiment of the present invention, digital data in a data set is checked for saturation, the current to the gain material adjusted at locations in the data set where saturation was found, and new data acquired at the adjusted current levels. If optical clocking methods are used it is desirable to maintain a strong clock signal, so the adjustable gain element may be placed in the imaging optical path only.

Sweep Alignment and Phase Stabilization

The Fourier transform (or inverse Fourier transform) of the OCT fringe contains both magnitude and phase information. Most applications only use the magnitude information to generate intensity OCT images. The phase information can be used for Doppler OCT and for measuring very small deflections and vibrations. If there is any sweep-to-sweep variation in the emission from the tunable source, the variation can show up in the phase information obtained by the OCT fringe. Without phase stabilization, it is hard to separate phase perturbations caused by variation in the tunable source from phase changes originating from changes within the sample. Optical clocking of the acquisition system can reduce or eliminate the effects of sweep-to-sweep variation. One preferred embodiment of the present invention uses optical clocking to improve the phase stability of the OCT fringe for phase sensitive OCT. Optical clocking helps to remove the effects of sweep-to-sweep variation, but there is still the possibility that the data is not similarly aligned from data acquisition frame (A-scan) to data acquisition frame (A-scan) as there can be uncertainty to the initial phase. One preferred embodiment of the present invention uses a wavelength signal or interferometric signal to stabilize the phase of the OCT fringe information for phase sensitive OCT. Several embodiments for phase stabilization are described next.

During OCT imaging, an acquisition system acquires the interferometric fringe from the sample. It is common that a predetermined number of data points are defined within a data capture frame or window for each wavelength sweep and that acquisition of data starts on an electrical edge transition. It is also possible that the data acquisition system not rely on a predetermined number of points, but operates by collecting data on a low or high level of a control signal. In both methods, acquisition begins on or around a transition of a trigger signal. The multiple asynchronous clocks in most OCT systems combined with normal and expected variation in operation create the possibility of one to a few sample points of uncertainty in the actual start of the acquisition relative to the wavelength sweep. Even a single sample point difference between sweeps can significantly degrade the phase information. Further, for intensity imaging, phase perturbations generate artifacts in the image when background subtraction of the sweep is performed, as is often practiced in Swept Source OCT. Phase stabilization that corrects for this potential alignment error has been shown to improve the quality of background subtraction and eliminate fixed pattern artifacts in the OCT images.

Figure 42:
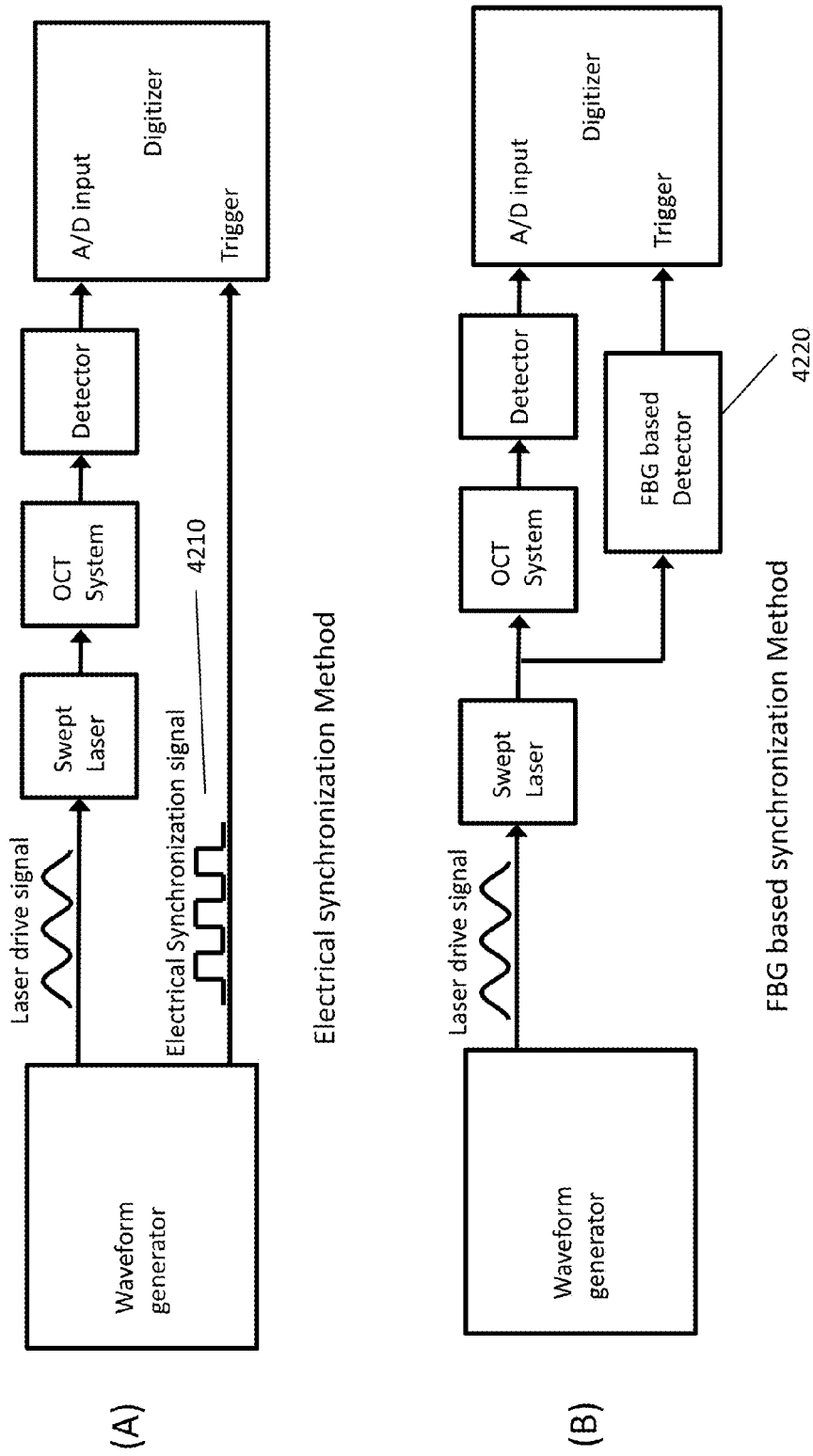
FIG. 42 is a set of block diagrams illustrating sweep data initiation using an input to the trigger of the acquisition system.

It is possible to use an electrical trigger signal 4210 that is synchronized with the tuning of the tunable source to start the A/D converter acquisition for each A-scan, as shown in FIG. 42A. One preferred embodiment of the present invention uses a trigger signal that is synchronized with the tuning of the tunable source and used for proper A/D acquisition data alignment. However, if there is sweep to sweep variation, it can be desirable to trigger off a wavelength signal using a FBG based detector 4220 instead of relying on pure temporal synchronization with the tunable source drive signal, as shown in FIG. 42B. An FBG 3330 for this purpose is shown in FIG. 33.

One preferred embodiment of the present invention uses an optical wavelength signal for proper A/D acquisition data alignment. The wavelength trigger signal can be generated by a Fiber Bragg Grating (FBG), a dispersive prism or grating, dispersive prism or grating with reflector, Fabry-Perot filter, wavelength demultiplexer (WDM), or any other wavelength selective device.

Figure 43:
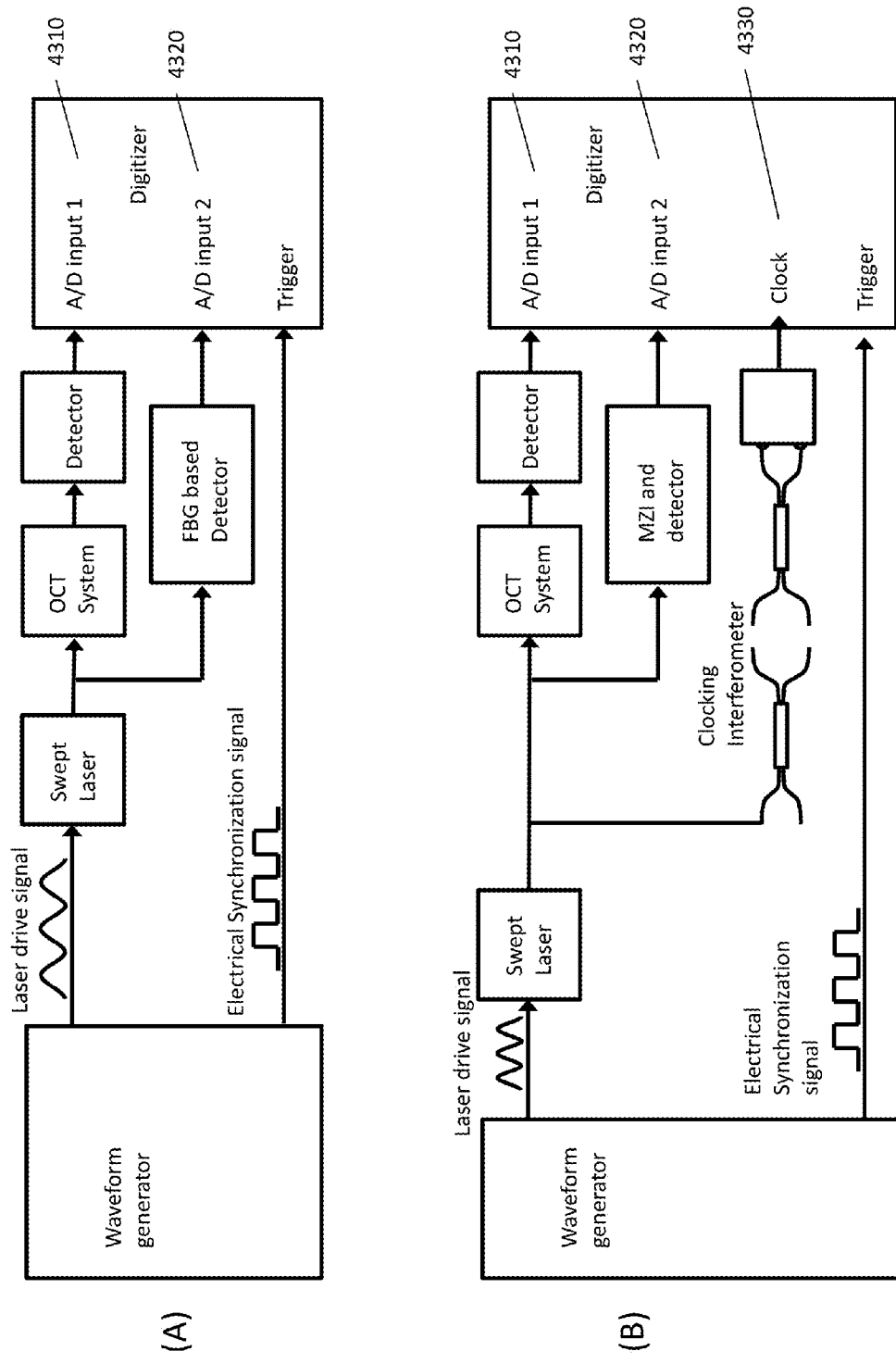
FIG. 43 is a set of block diagrams illustrating sweep phase stabilization using multiple channels of A/D conversion to perform the synchronization.

In these previous examples of data alignment, the trigger generally coincides with the start of the data of interest. It is also possible that the trigger occurs somewhere between the start and end times of the data of interest. In this case, the position or time of an optical wavelength trigger relative to the acquired data is acquired and the position or time information used to properly adjust alignment of the acquired data to the data frame. For example, the trigger could be acquired on an additional channel of A/D acquisition 4320, as shown in FIG. 43A, or a counter could determine where the trigger occurred relative to the start of data acquisition. In one preferred embodiment, a wavelength trigger consisting of a Fiber Bragg Grating is placed near the center of the tuning range, which allows for proper frame alignment and accommodation for the changes in acquisition requirements as the tunable source executes different sweep trajectories for different modes of OCT operation. The alignment signal can also be interferometric, where an optical interferometric signal is used for proper A/D acquisition data alignment, as shown in FIG. 43B. Alignment of the reference fringe acquired by the second channel of A/D conversion aligns the OCT data with both channels of A/D acquisition acquired with simultaneously sampling A/D. The alignment can be performed by correlation or forming an error vector and associating a metric with the error vector to be minimized as measured by a norm. Alignment can also be performed using the numerical sweep calibration methods described earlier in this document. An additional improvement applicable to many phase stabilization approaches can be obtained by optically clocking the A/D converters, as illustrated in FIG. 43B. Since the clock signal 4330, the OCT data on the first channel of A/D 4310, and the alignment fringe on the second channel of A/D 4320 are derived from the same optical signal, there is no relative phase shift between the signal channels. By shifting the data at integer intervals within the acquired data, simple alignment of the alignment fringe by matching the current fringe to a reference fringe and looking at an error metric allows proper phase alignment of the OCT data. In practice, the data from each A-scan is acquired into a memory location in a computer. The proper data shift from matching of the alignment fringes produces an integer shift to properly align the data because of the synchronization of all signals to the optical source. The integer shift, m, can be used as an offset for a memory location read of the array of data. Data sufficiently before the expected start of valid data, i_start_nominal, and data after the expected end of valid data, i_end_nominal is acquired. The estimate of how much data to acquire before and after is based on the expected jitter in sweep acquisition and will likely be 1-10 data points. If the data associated with a sweep requires a shift of m data points for example, data can be read from a nominal starting memory location, i_start_read=i_start_nomimal+m, to a nomiminal ending memory, i_end_read=i_end_nominal+m. The data between the two points, i_start_read and i_start_end, represents the phase aligned sweep data, which can be copied from these memory indices for processing or storage.

Figure 44:
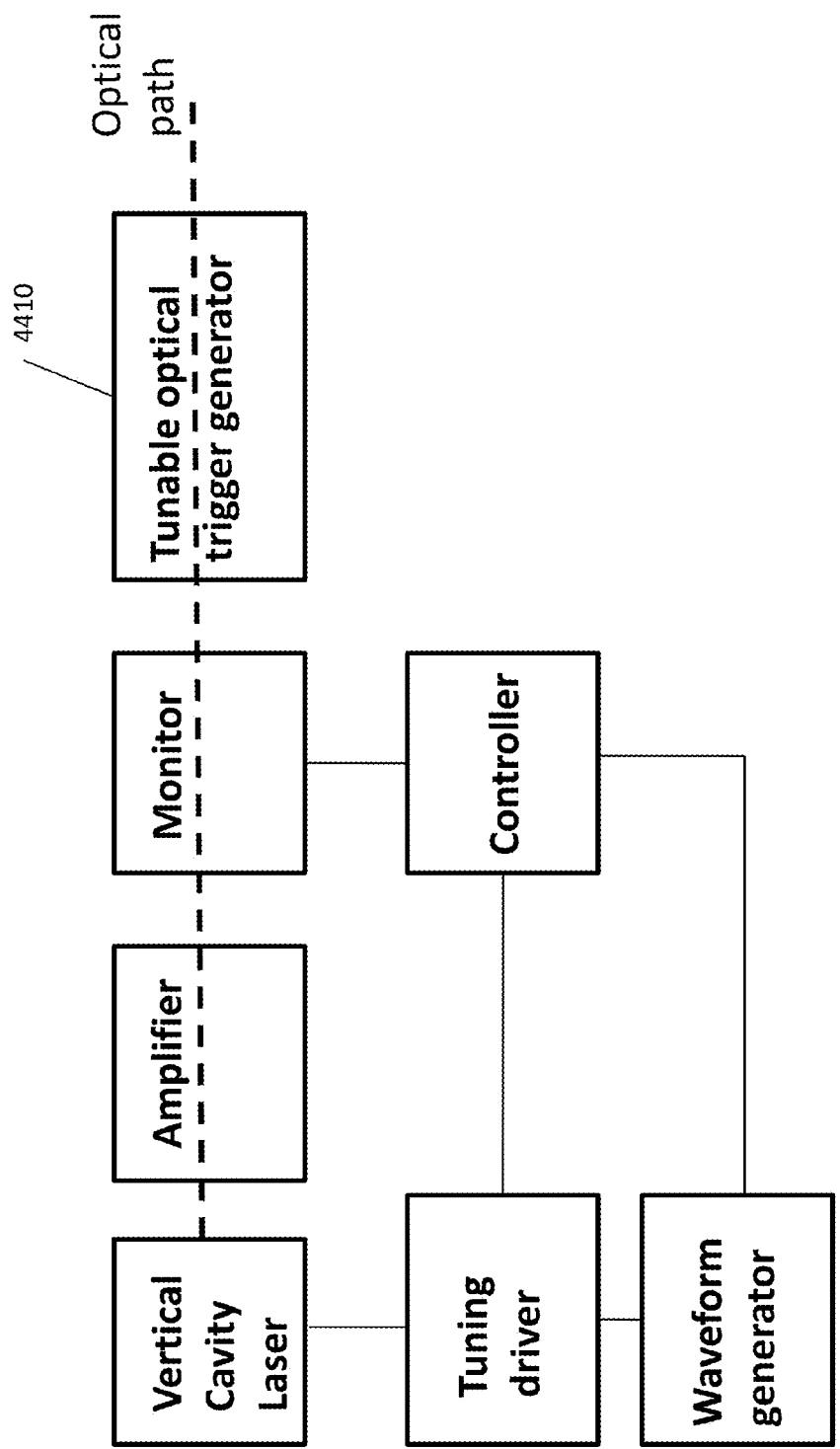
FIG. 44 is a block diagram illustrating a tunable optical trigger generator.

Instead of using a fixed wavelength trigger, it is also possible to use a tunable optical trigger 4410, as shown in FIG. 44. A tunable wavelength trigger provides high flexibility in accommodating different sweep trajectories and OCT imaging modes. One preferred embodiment of the present invention includes a tunable optical trigger to initiate the acquisition of data so as to properly align the acquisition frame window to the wavelength sweep. More specifically, one preferred embodiment of the present invention includes the case were a tunable optical trigger is used to initiate the acquisition of data so as to properly align the acquisition frame window to the wavelength sweep to accommodate different sweep ranges. The tunable filter can be tuned by many different methods. For example, the spacing in a Fabry-Perot filter can be changed, the index of refraction of material in a Fabry-Perot filter can be changed, or the position of a detector relative to a dispersive prism or grating could be changed, or the dispersive properties of the grating itself changed to be selective to a desired wavelength. Other methods of adjusting an optical trigger are also included in the present invention.

Using an optical device that generates a single fixed wavelength trigger over the sweep range can present challenges when changing the sweep range of the instrument because the sweep range is confined to span the wavelength of the trigger device. Using an optical device that generates a sharp transition in wavelength, such as an FBG presents challenges because the rate of change of the transition is highly dependent on the wavelength sweep velocity. If the peak is narrow with a rapid change in output vs. time, then the peak and signal transition can be missed at high sweep speeds. If the peak has a slow transition, determining the absolute position of the peak can be challenging in the presence of noise.

Performing phase stabilization while accommodating different sweep ranges and sweep repetition rates can be robustly performed using a static optical element that generates multiple wavelength signals with desirable rate of transition. For example, a Fabry-Perot filter with small gap length can generate multiple transmission peaks within the sweep range of the tunable source. FIG. 45A shows a diagram illustrating a method of phase stabilization using a Fabry-Perot filter. The majority of light from the tunable source 4510 is directed to the OCT system 4520, where a detector 4530 measures the optical signal, which is digitized by a first A/D converter 4540. A small portion of the light from the tunable source is directed to a Fabry-Perot filter 4550. A detector 4560 measures the optical signal from the Fabry-Perot filter and an A/D converter 4540 digitizes the Fabry-Perot signal. The two A/D converters simultaneously sample the signal and operate off the same clock. An example normalized transmission vs. wavelength plot of a Fabry-Perot filter with a gap length of 40 microns and mirror reflectivity of 0.5 is shown in FIG. 45B. The spacing of Fabry-Perot transmission peaks is coarse enough that any one peak within the sweep range of the tunable source can be chosen as the reference peak in a first reference sweep and it is not possible that trigger jitter or phase jitter caused by sweep-to-sweep variation or electrical trigger jitter in any subsequent sweep would be large enough to cause a neighboring peak in a subsequent sweep to shift enough to be confused with the reference peak. Further, since there are multiple peaks in the signal from the Fabry-Perot, aligning multiple peaks reduces phase uncertainty caused by noise, thereby improving the robustness of the approach. A Fabry-Perot filter can be used for phase alignment using a software calibration approach or an optical clocking approach. In the case of software calibration, the peaks of the transmission function indicate positions of absolute wavelength, so sub-sample shifts can be performed to the OCT fringe data to achieve improved phase alignment. In the case of optical clocking, the intimate relationship created by generating the clock signal from an interferometer as an absolute function of wavelength, the Fabry-Perot signal from an etalon as absolute function of wavelength, and the OCT signal from the same optical source creates a phase coherence between the three signals, irrespective of electronic drive signal or sweep-to-sweep variation. Consequently, any sample shift between sweep acquisitions occurs from trigger uncertainty in the data acquisition system, and phase alignment can be achieved by integer shifts of the acquired data if the clocking interferometer is stable. Performing integer shifts of the acquired data is considerably less computationally expensive than interpolating the fringe data. The alignment of the Fabry-Perot data and the integer shifting can be performed in a processing unit before transmission to memory for processing or to other media for storage.

Figure 45:
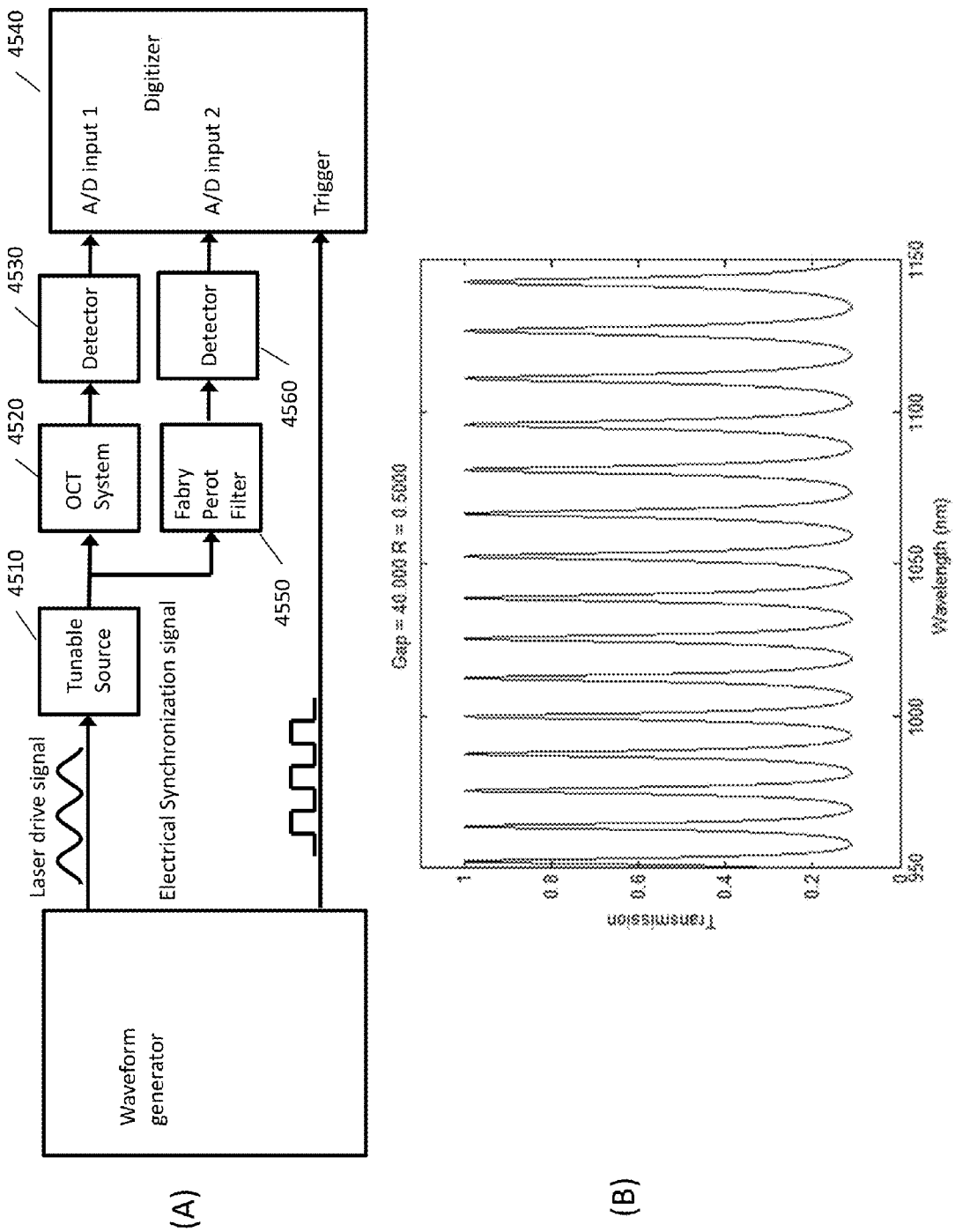
FIG. 45 is a block diagram and a plot showing sweep phase stabilization using a Fabry-Perot filter.

Since many popular A/D converter cards used to perform OCT imaging have two channels of simultaneously sampling A/D conversion and many have onboard FPGA processing capability, the method illustrated in FIG. 45 works well for intensity OCT imaging, phase sensitive OCT imaging, and Doppler OCT imaging that only require one channel of OCT data. In applications where only one high speed A/D converter is available, or in the case of performing Polarization sensitive OCT imaging which requires two channels of high speed A/D conversion for each channel of OCT data, it may be desirable to use an auxiliary A/D convert that digitizes at a reduced speed. A 10-250 MSPS A/D converter is significantly less expensive than the 400 MSPS-3.6 GSPS A/D converters currently often used for Swept Source OCT.

Figure 46:
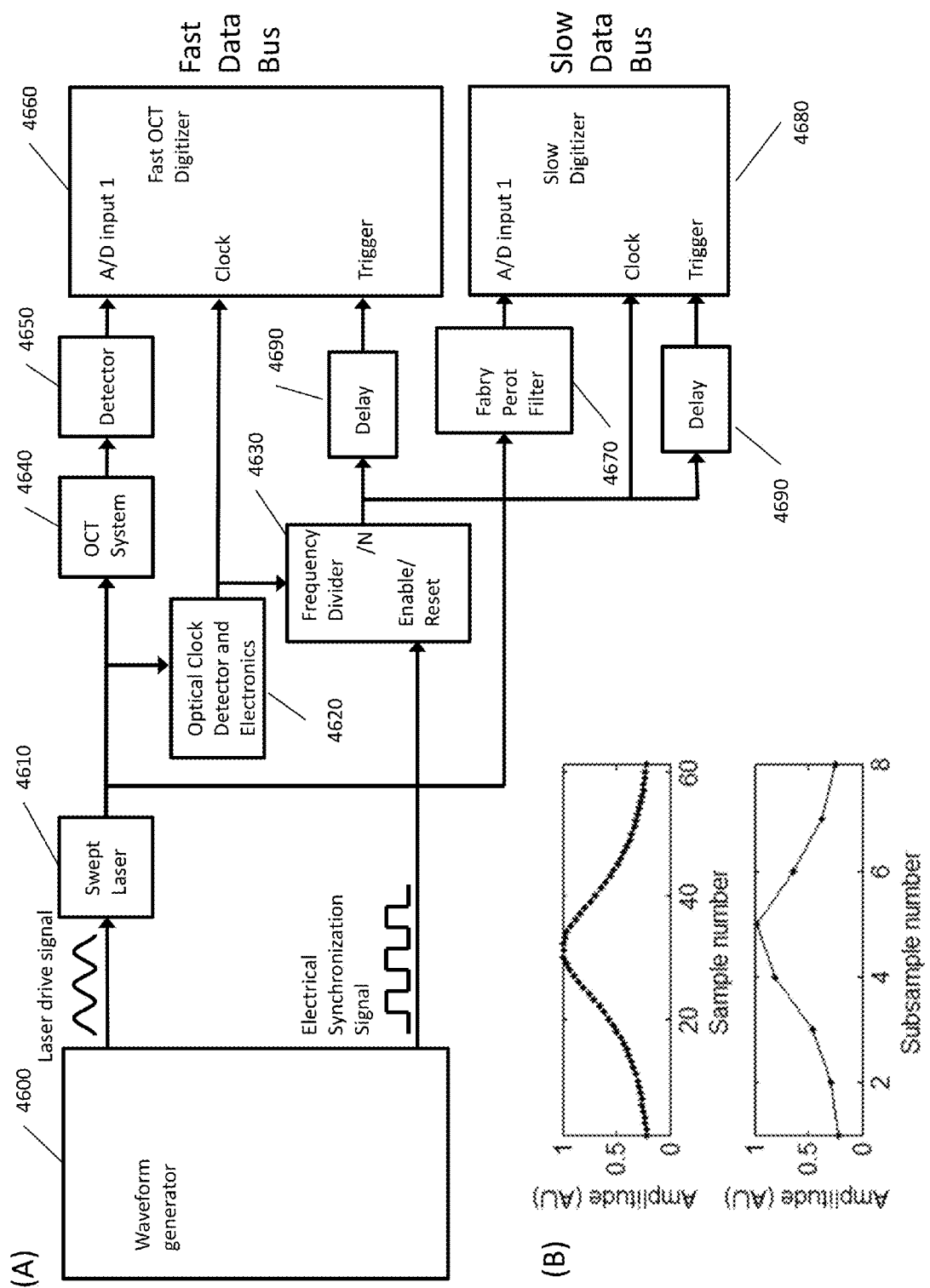
FIG. 46 is a block diagram and plot illustrating sweep phase stabilization using a Fabry-Perot filter with a fast and slow A/D converter.

FIG. 46A illustrates digitizing the OCT signal on a fast A/D converter and digitizing a Fabry-Perot signal on a slow A/D converter. An optical clock detector and electronics 4620 generate a clock signal from an output of the tunable source 4610. The fast A/D converter is clocked directly off the output of the optical clock detector and electronics while a frequency divider 4630 or counter reduces the clock rate by a factor of N to the slow A/D converter. The majority of light from the tunable source is directed to the OCT system 4640. Light from the OCT system 4640 is detected by a detector 4650 and digitized by the fast A/D converter 4660. A minority portion of light from the tunable source is directed to a Fabry-Perot filter 4670, the output of which is digitized by the slow A/D converter 4680. In order to eliminate jitter between the two A/D converters, the triggers from both the fast and slow A/D converters are triggered by a common signal with optional individually tunable delay 4690 in each trigger signal to compensate for A/D converter latency. The delay can also be used to ensure that the trigger event occurs near the center in time between two adjacent clock signal transitions to reduce chance of missing the trigger event on either of the A/D converters. In the system illustrated in FIG. 46A, the trigger signal originates from the output of the frequency divider 4630 or counter in order to synchronize the fast and slow A/D converter. A signal from the waveform generator 4600 resets and enables the frequency divider 4630 or counter such that the trigger signal shared between the fast and slow A/D converters occurs on a transition of the output of the divide by N counter, thereby synchronizing the data samples between the fast and slow A/D converters. FIG. 46B shows a signal that would be generated from a Fabry-Perot filter digitized using optical clocking with the fast (top plot) and slow (bottom plot) A/D converters. If captured by the fast A/D converter, the shape of the transmission peak waveform is easy to discern. If captured by the slow A/D converter, the sampling of the transmission peak is sparse and it is more difficult to identify the location of the peak in the data. Methods developed for time delay estimation can be used to identify shift between similar signals to subsample accuracy to properly align the data.

Time delay estimation (TDE) methods were developed to be able to estimate the time difference of arrival to multiple channels of acquisition. Many methods of TDE are based on finding the peak of the cross correlation function of two signals. A class of time delay estimation techniques, called subsample time delay estimation, seek to improve the performance of TDE by interpolating the peak of the cross correlation function and finding the interpolated maximum value. Gaussian interpolation, parabolic interpolation, and cosine interpolation methods are a few example interpolating functions that have been used for subsample TDE. Other interpolation and subsample TDE methods are possible and included in the present invention. The input signals can be filtered for improved TDE accuracy. The cross correlation function can also be filtered to aid in estimating the position of the peak.

Figure 47:
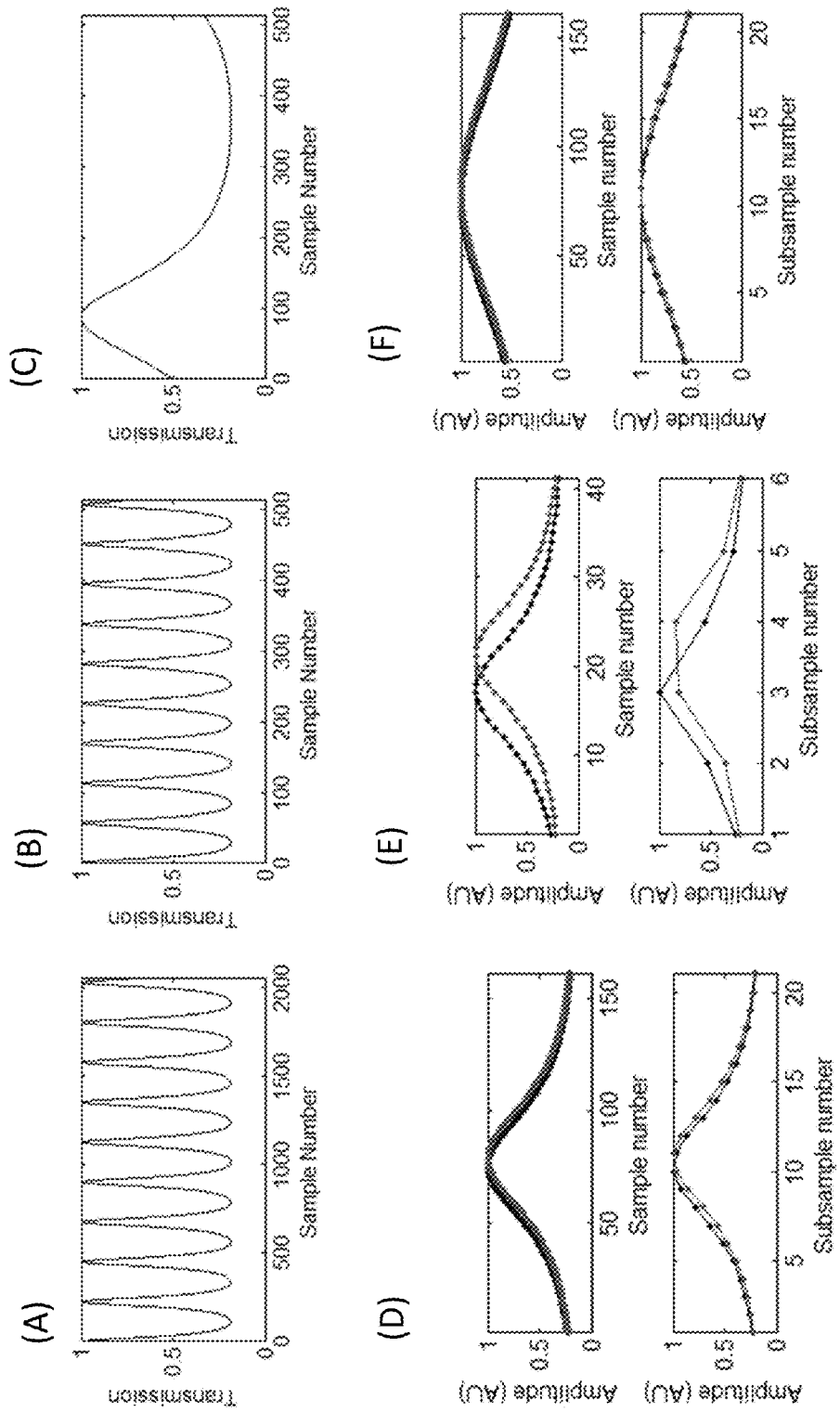
FIG. 47 is a collection of plots showing phase stabilization using time delay estimation applied to different OCT system operating modes.

An embodiment of the present invention is capable of operating at different operating modes. FIGS. 47A-47C show the signal that would be expected from a Fabry-Perot filter with a 50 micron mirror separation and 40% mirror reflectivity for example operating modes of: (A) 50 kHz repetition rate imaging over 100 nm of wavelength tuning centered at 1050 nm, (B) 200 kHz repetition rate imaging over 100 nm of wavelength tuning centered at 1050 nm, and (C) 50 kHz repetition rate imaging over 10 nm of wavelength tuning centered at 1045 nm. The corresponding signals from a fast (top) and slow (bottom) A/D converter are shown in FIG. 47D-47F corresponding to the operating points shown in 47A-47C. In FIGS. 47A-47C, a sample delay of 4 samples with respect to the fast A/D converter has been applied to the fast A/D converter waveform to represent the integer valued sweep-to-sweep jitter expected from the acquisition hardware. Jitter from 0-10 samples would be expected in general between sweeps. The signal as sampled by the slow A/D converter is shown as it would be sampled with the 4 sample shift. Time delay estimation was applied to the slow A/D converter signal and the results shown in Table 1. In the case of A and C, the system is operated in a mode that samples the Fabry-Perot signal with high sampling density. Consequently, the delay estimates from TDE for case A and C are very accurate. In case B, the system is operated in a mode that sparsely samples the Fabry-Perot signal. Even in the case B, the TDE estimate is accurate within one sample point, enabling proper phase stabilization of the data. This illustrates how a single fixed Fabry-Perot filter can be used to phase stabilize the data over a wide range of operating points. Adjustable Fabry-Perot filters and using multiple Fabry-Perot filters, or other similar wavelength specific devices are also included in some embodiments of the present invention.

TABLE 1

| Peak | Parabola | Gaussian |
|------|----------|----------|
| (A)  |          |          |
| 1    | 3.9950   | 3.9951   |
| 2    | 3.9986   | 3.9986   |
| 3    | 3.9877   | 3.9879   |

TABLE 1-continued

| Peak | Parabola | Gaussian |
|---|---|---|
| 4 | 3.9931 | 3.9932 |
| 5 | 3.9972 | 3.9973 |
| 6 | 4.0000 | 4.0000 |
| 7 | 4.0016 | 4.0015 |
| 8 | 3.9957 | 3.9957 |
| (B) | | |
| 1 | 4.1178 | 4.1039 |
| 2 | 4.2278 | 4.2016 |
| 3 | 3.7974 | 3.8208 |
| 4 | 3.9096 | 3.9203 |
| 5 | 4.0286 | 4.0252 |
| 6 | 4.1447 | 4.1279 |
| 7 | 4.2526 | 4.2238 |
| 8 | 3.8234 | 3.8439 |
| (C) | | |
| 1 | 3.9931 | 3.9931 |

In one preferred embodiment, time delay estimation methods are used to phase stabilize the digital data. In one preferred embodiment, an adjustment to the digital data is performed to phase stabilize the digital data, the adjustment being calculated using time delay estimation (TDE) techniques.

Center of gravity based estimates of the peaks can also be performed and are included in the TDE techniques described in the context of the present invention.

Polarization Control

Some of the elements in the tunable source are sensitive to polarization state. For example, BOA and SOA optical amplifiers, as well as some optical isolators are often polarization sensitive. It is therefore beneficial to align the polarization entering polarization sensitive elements to maximize throughput and to avoid introducing imaging artifacts caused by slightly different path lengths associated with different polarization state. The preferred embodiment of the present invention uses one or more polarization controlling elements in the optical circuit to cancel unwanted polarization artifacts or reduce losses. Polarization sensitive elements can help with aligning the polarization state. One preferred embodiment of the present invention comprises a tunable source that uses at least one polarization sensitive isolator with closed loop, manual, or otherwise adjustable control of the input fiber polarization state to a polarization sensitive isolator. Proper polarization can be determined by maximizing power throughput of a polarization sensitive isolator. One preferred embodiment of the present invention comprises a tunable source that uses at least one polarization sensitive optical amplifier with closed loop, manual, or otherwise adjustable control of the input fiber polarization state to a polarization sensitive optical amplifier. Standard optical fiber does not maintain the polarization state of the incoming light and changes the polarization state through birefringent effects due to stresses within the fiber. One preferred embodiment of the current invention uses polarization controllers to generate a desired polarization state after the state has been perturbed by passing though non-polarization maintaining fiber. Alternatively, polarization maintaining fiber can be used to simplify alignment and operation of the imaging system and tunable source. One preferred embodiment of the present invention uses polarization maintaining fiber to connect optical subcomponents to eliminate the need for polarization controllers between select optical subcomponents. One preferred embodiment of the present invention uses active polarization control within the optical circuit to detect and cancel unwanted polarization artifacts. The measurement of degree of polarization alignment can be the power or intensity of the output. A simple diode or other power measuring device can be used. One embodiment measures power over multiple wavelengths by a monitoring module, such as that shown in FIG. 28 or 30.

Data Streaming, Processing and Storage

Figure 48:
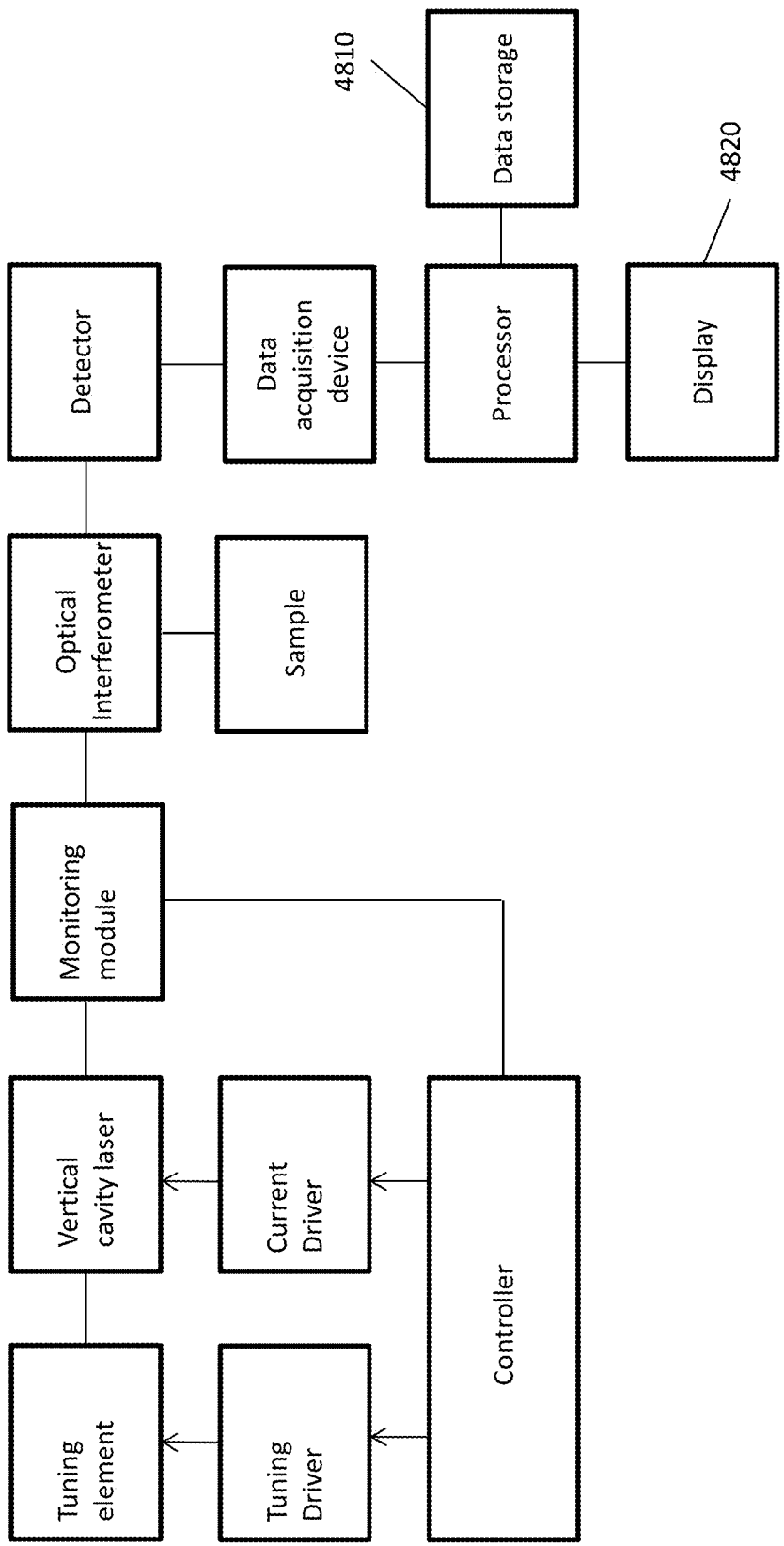
FIG. 48 is a block diagram of an imaging system with data processing, data storage, and data display capability.
Figure 49:
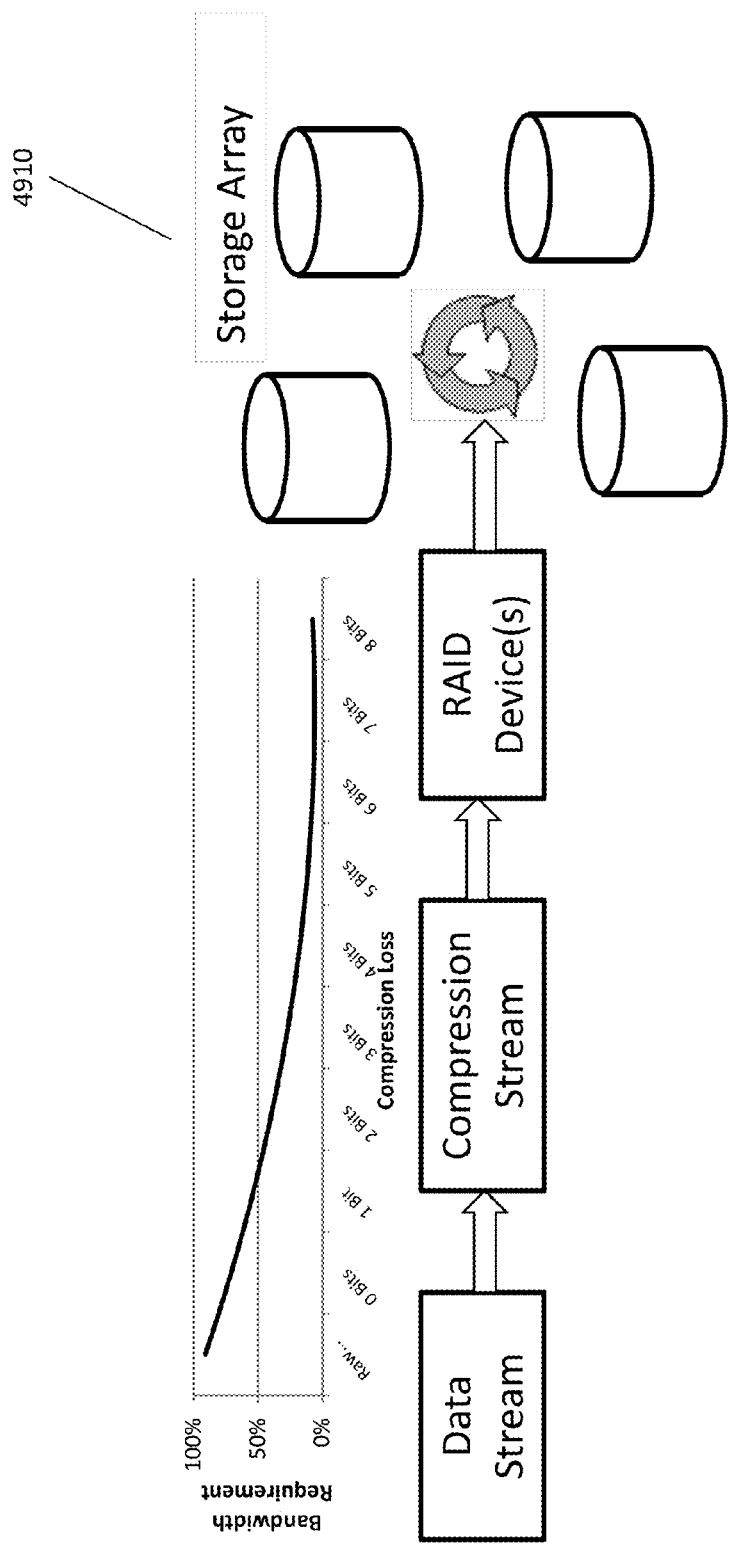
FIG. 49 is a block diagram of a data stream showing compression of the data and storage of the data on a RAID array.

Once the OCT data stream starts to be acquired, it can be processed, stored, displayed, transmitted, or used for realtime feedback and control. A preferred embodiment that stores data in a data storage 4810 and displays data on a display 4820 is illustrated in FIG. 48. Another preferred embodiment does not necessarily store or display the data, but uses the OCT measurement in a closed loop process. Applications that benefit from realtime feedback and control include positioning systems, robotic systems, processing systems, manufacturing systems, tuning systems, and other systems that make use of OCT data in realtime for adjusting a parameter of a process. One preferred embodiment of the present invention includes a means for storing the acquired data. The means for storing the acquired data could be memory, disk, tape, optical recording media, volatile memory, non-volatile memory, magnetic media, optical memory, or any other means for storing data known in the art of data storage. The OCT imaging system is capable of generating large data volumes in short timeframes. A single device for storage could be overwhelmed with the data flow rates. Dividing the data flow and portioning out data streams to multiple storage devices can increase the allowable data throughput. One preferred embodiment of the current invention stores data on a RAID array 4910, as illustrated in FIG. 49. One preferred embodiment of the current invention includes a means for processing the acquired data to construct images of the sample. The means for processing the acquired data could be a processor, a CPU, a microcontroller, a digital signal processor (DSP), field programmable gate array (FPGA), graphics processing unit (GPU), network of computers, state machine, or any other means of processing data known in the art of data processing. One preferred embodiment of the present invention includes a means for displaying the acquired data. The means for displaying the acquired data could be a monitor, a computer monitor, a television, a projector, a printout, a handheld computer, a handheld tablet, cell phone, LCD screen, LED screen, LED array, or any other means known in the art of image display. It can be advantageous to reduce the storage or transmission requirements by compressing the data. One preferred embodiment of the current invention compresses the data. The current invention also includes the case where the data is compressed with a lossless algorithm. Combinations of data utilization are included in the current invention. One preferred embodiment of the current invention includes the case where the system contains a processing unit that processes the data to generate image data and the image data being transmitted to a host computer, storage, or display device. One preferred embodiment of the current invention includes a means for transmitting the data through electrical cables, optical communications links, fiber optics communications link, or a radio transmitter. The means for transmitting could be a voltage transmitter, a current transmitter, a frequency modulator, and amplitude modulator, a light source, radio transmitter, or any other means for transmitting data known in the art of data transmission. The current invention includes the case where the system includes a data transmitter of any kind.

The small size of the VCL source enables OCT systems that are small and light weight. One preferred embodiment of the present invention is an imaging system that is hand held. One preferred embodiment of the present invention is an imaging system that is field portable. One preferred embodiment of the present invention is an imaging system that is battery powered.

Specific and more general implementations of some embodiments of the present invention have been described. One preferred embodiment of the present invention is an optical coherence tomography imaging system comprising: A VCL source that has the characteristics of being able to image over adjustable depth ranges, axial resolutions, and at continuously adjustable speeds, the optical coherence tomography system being able to image over an extended imaging range enabled by the long coherence length of the VCL source. Although flexible in its operating modes, one embodiment operates at a substantially fixed sweep repetition rate. Another embodiment operates at a substantially fixed imaging range. Another embodiment operates at a substantially fixed OCT axial resolution. One embodiment includes a clocking interferometer, clocking detector, and electronic circuit clock an A/D converter, the clocking interferometer having adjustable optical delay to enable operation at different speeds, axial resolutions, and depth ranges within the acquisition bandwidth. One embodiment includes a clocking interferometer, clocking detector, and electronic circuit clock an A/D converter, the clocking signal being multiplied or divided in frequency to enable operation at different speeds, axial resolutions, and depth ranges within the acquisition bandwidth. One embodiment exploits adjustability in axial resolution and speed to operate the OCT imaging system at two or more modes of higher resolution and slower speed or lower resolution and higher speed without exceeding the data acquisition bandwidth. One embodiment exploits adjustability in imaging range and speed to operate the OCT imaging system at two or more modes of longer imaging range and slower speed or shorter imaging range and higher speed without exceeding the data acquisition bandwidth. One embodiment exploits adjustability in axial resolution and imaging range to operate the OCT imaging system at two or more modes of higher resolution and shorter imaging range or lower resolution and longer imaging range without exceeding the data acquisition bandwidth.

Multiple VCL Implementation

Figure 50:
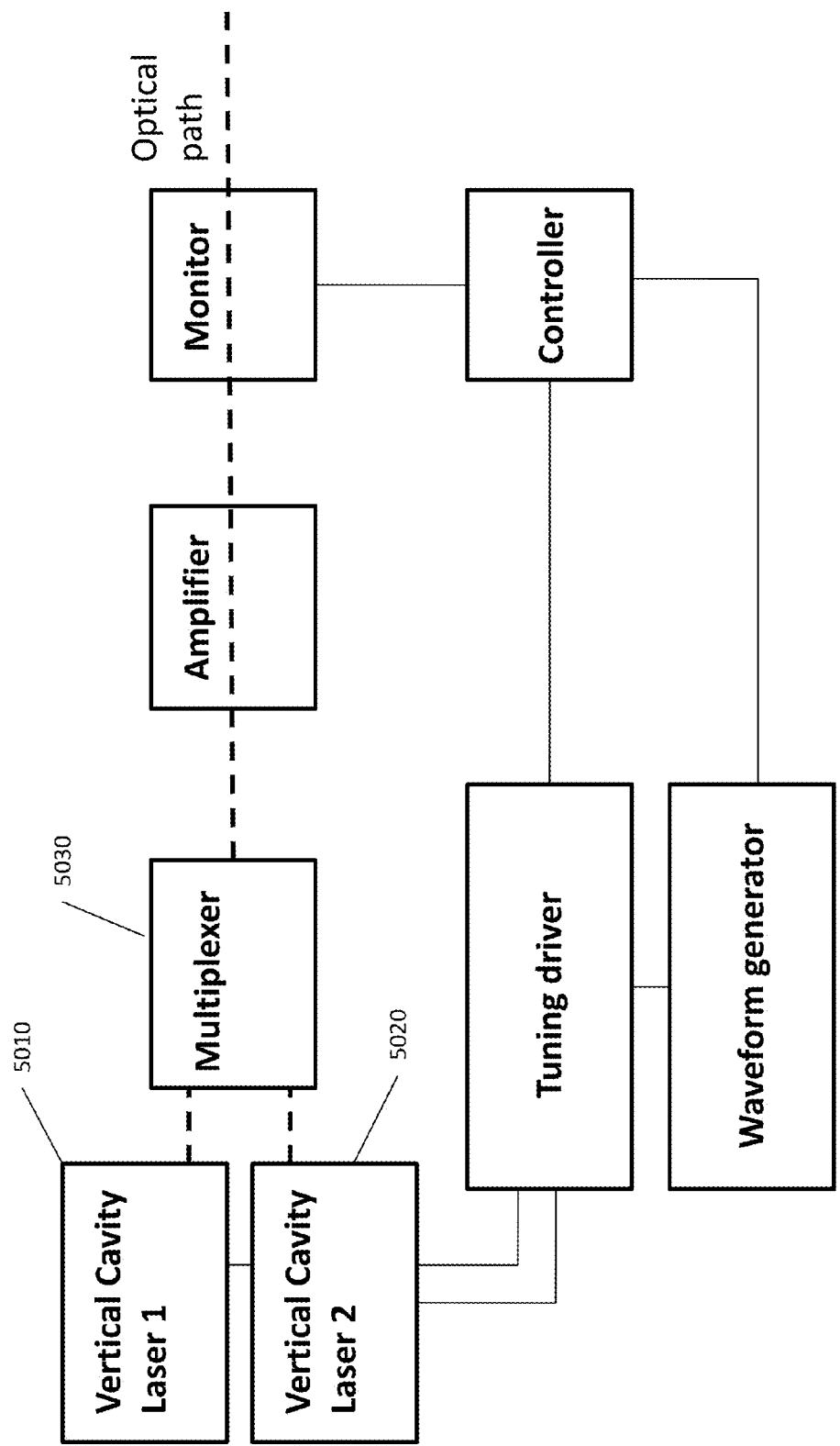
FIG. 50 is a block diagram of a sweep repetition rate multiplier using multiple VCL sources.

A basic implementation of an embodiment of the invention uses only one VCL in the tunable source. It is possible that two or more VCLs operate together to generate a more preferable tunable source output emission, as illustrated in FIG. 50. The outputs of the VCLs 5010, 5020 can be combined with a switch, splitter/combiner, WDM, coupler, circulator, beam splitter, polarization sensitive beam splitter, multiplexor or any other means for combining two or more optical signals 5030. When multiple VCLs are combined, it is beneficial to blank out portions of the sweep or design the VCL to inherently not have emission over a portion of the sweep so that sweeps from multiple VCLs or the same VCL can be combined. One preferred embodiment of the present invention uses a tunable laser comprising multiple VCLs, wherein the sweeps of the multiple VCLs are interleaved to increase the effective sweep repetition rate. One preferred embodiment of the present invention uses a tunable source comprising multiple VCLs to improve sweep linearity, wherein the VCL sweeps are interleaved and the sweep range is larger than one FSR and only the central most linear portion of the sweep is used for imaging.

Figure 51:
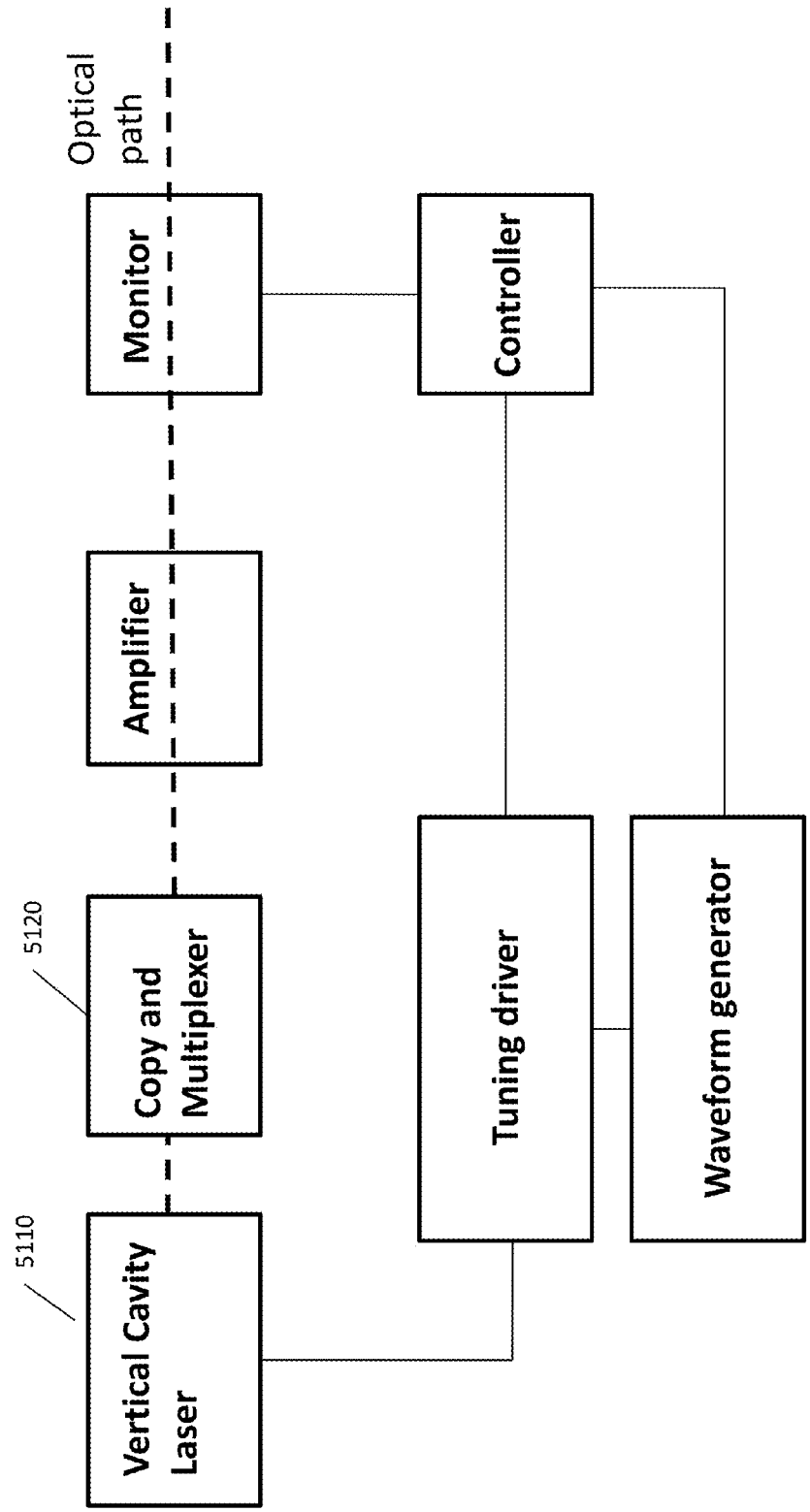
FIG. 51 is a block diagram of a sweep repetition rate multiplier using a single VCL source.

Birefringent artifacts in OCT images can sometimes be ameliorated by illuminating the sample with emission of different polarization states. Some polarization sensitive imaging systems illuminate the sample with light of more than one polarization state. Different polarization states can be generated by using more than one VCL source in the imaging system. One preferred embodiment of the present invention uses at least two VCL sources to generate emission of different polarization states. Further, one preferred embodiment of the present invention uses at least two VCL sources to generate different polarization states and the sweeps from the different polarization states are interleaved to perform polarization sensitive OCT. One preferred embodiment of the present invention uses at least one VCL source and a polarization modulator to generate different polarization states. A single VCL source 5110 can also be used in a sweep interleaved mode with a copy and multiplexer device 5120, as illustrated in FIG. 51. One preferred embodiment of the present invention uses a fiber loop to optically copy and time delay the sweep, the copied sweep being combined and interleaved with the original sweep to increase the effective sweep repetition rate of the laser. When interleaving sweeps, the ratio of the FSR to the wavelength range supported by the gain material can be used to generate a preferable sweep characteristic. One preferred embodiment of the present invention uses an FSR of the tuning element that is substantially larger than what is required to scan across the full tuning range of the tunable source such that the laser duty factor is low to facilitate copying and insertion of the sweep from the same tunable source or a different tunable source as a way to multiplex sweeps. One preferred embodiment of the present invention uses a tuning element that sweeps a range larger than one FSR to improve linearization of the sweep. Another preferred embodiment of the present invention uses a tuning element that sweeps a range larger than one FSR to improve linearization of the sweep and where the sweep regions outside of the FSR are either blanked out through current modulation to a gain material, not acquired by the acquisition system, or modulated at the output of the source. One preferred embodiment of the present invention uses a tuning element that sweeps a range larger than one FSR to reduce the duty factor to enable insertion of sweep copies from the same laser or sweeps from a different laser.

The implementations of combining multiple VCL sources discussed to this point have combined substantially similar VCL sources to achieve a more desirable sweep characteristic. It can also be beneficial to combine substantially different VCL sources. One preferred embodiment of the present invention uses sweeps from two or more VCL sources with different center wavelengths that are interleaved to increase the effective wavelength sweep range of the source. Another preferred embodiment of the present invention uses sweeps from two or more VCL sources with different center wavelengths that are interleaved to obtain OCT information at the different wavelengths with sufficient separation to obtain different spectral information from the sample.

Additional Enhancements

Figure 52:
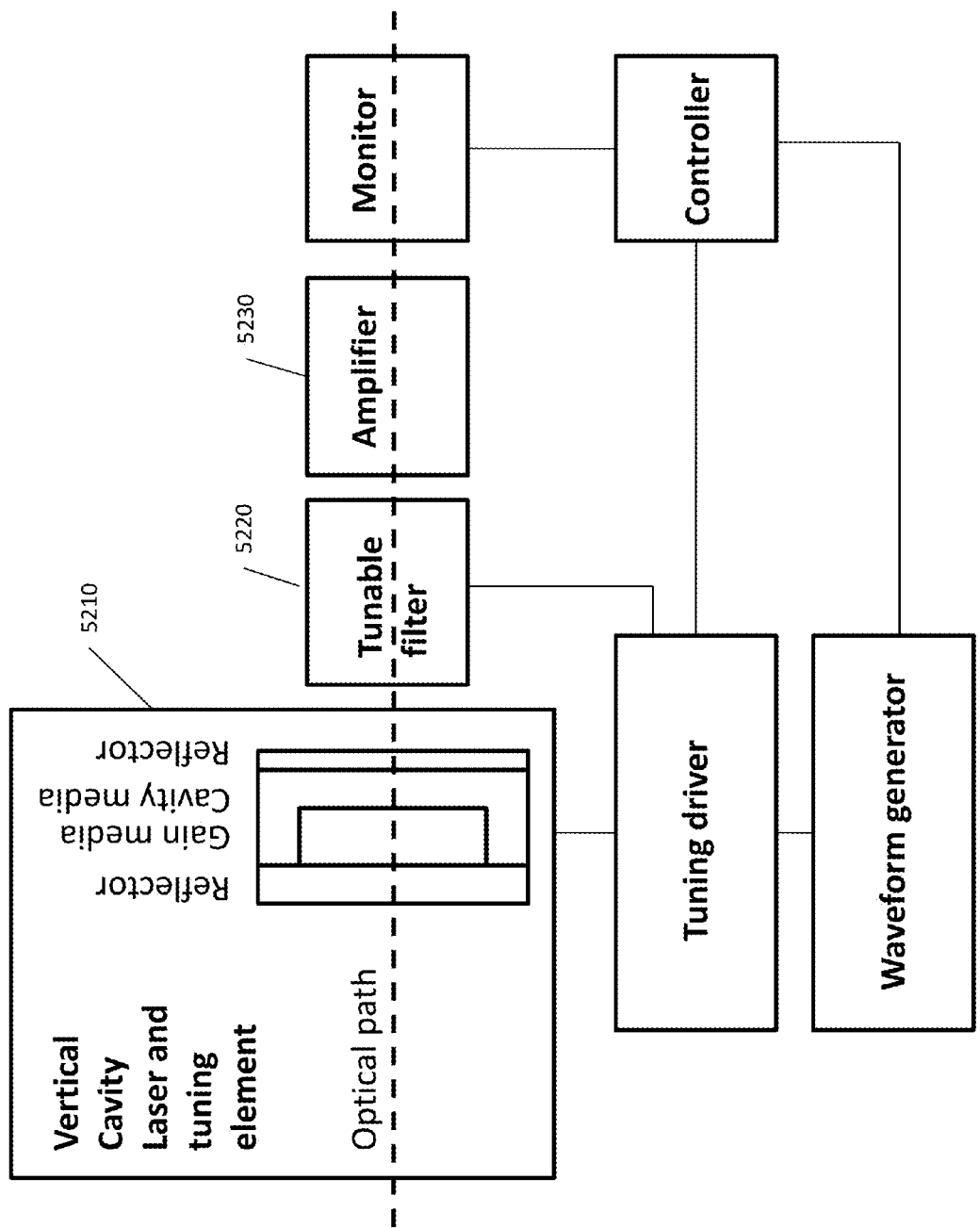
FIG. 52 is a block diagram of a closed loop wavelength tuning subsystem and optical amplifier with tunable filter to suppress sidemodes and amplified spontaneous emission.

The tunable source outputs tuned emission, as well as ASE and light from sidemodes. It can be beneficial to filter out the ASE so that it does not reach the sample or any optional optical amplification stage. One preferred embodiment uses tunable filters and synchronously tunes the filter with the tunable source to filter out ASE, as illustrated in FIG. 52. Tunable filters 5220 can be used and synchronously tuned with the tunable source 5210 to filter out sidemodes.

Figure 53:
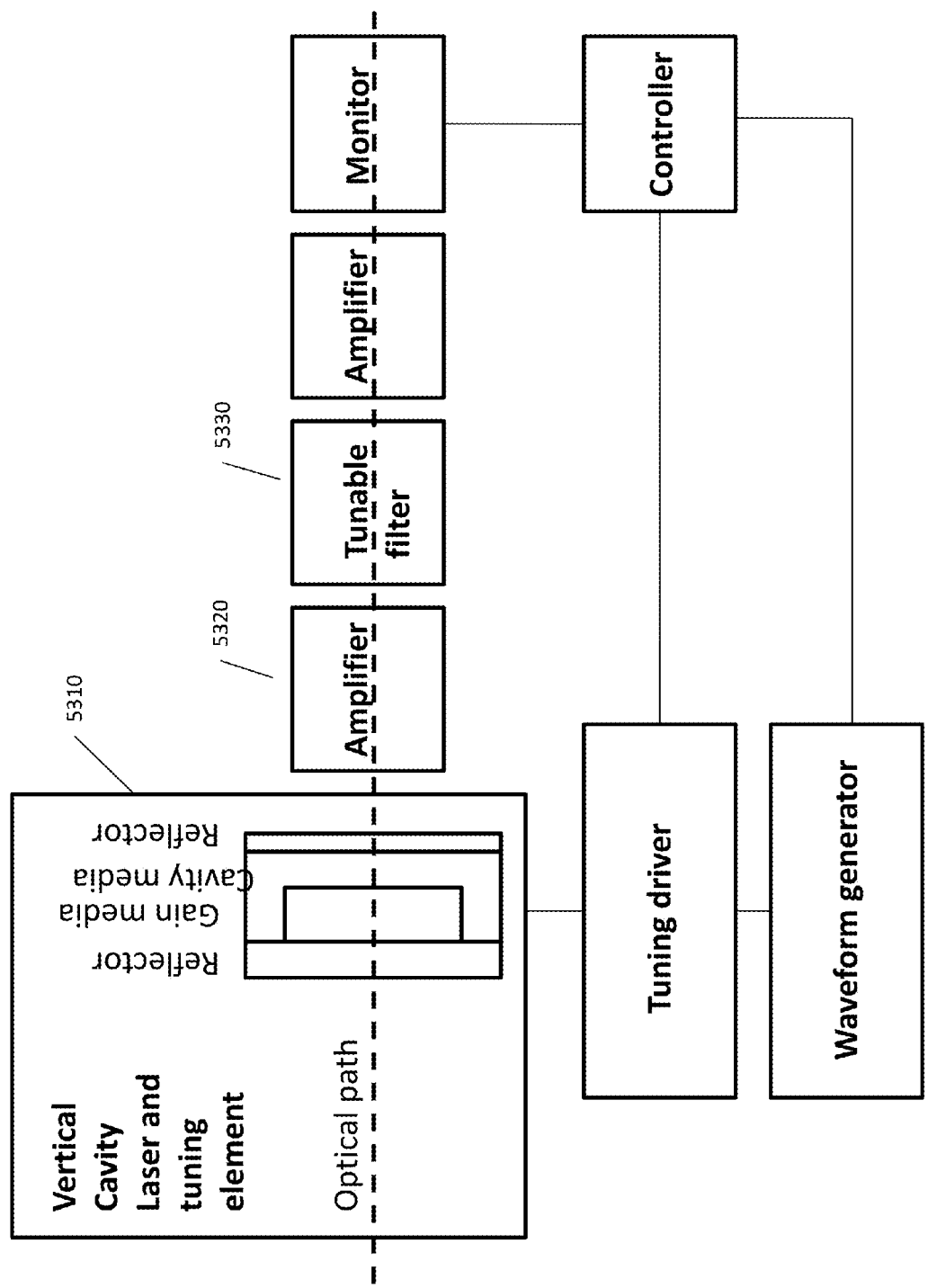
FIG. 53 is a block diagram of a closed loop wavelength tuning subsystem with multiple optical amplifiers and a tunable filter positioned between the amplifiers to suppress sidemodes and amplified spontaneous emission.

There are manly locations within the optical circuit where the tunable filter can be placed and the tunable filter and amplifier can potentially be combined. One preferred embodiment of the present invention includes at least one optical amplifier that is a vertical cavity amplifier synchronously tuned with the VCL source. One preferred embodiment of the present invention uses a tunable filter 5220 located somewhere between the VCL 5210 and amplifier 5230 that is synchronously tuned with the VCL to suppress ASE and improve sidemode suppression ratio. One preferred embodiment of the present invention also includes a tunable filter located somewhere after the VCL source that is synchronously tuned with the VCL to suppress ASE and improve sidemode suppression ratio. One preferred embodiment of the present invention includes a tunable filter 5330 located after any amplifier 5320 that is synchronously tuned with the VCL 5310 to suppress ASE and improve sidemode suppression ratio, as illustrated in FIG. 53.

It has been shown how a tunable filter and current control can be used to reduce ASE noise, shape the spectrum, suppress sidemodes, and reduce exposure to samples. It is possible to obtain similar functionality using passive devices. One preferred embodiment of the present invention includes an optical filter with a fixed wavelength filtering response that is inserted within the system along an optical path to shape the spectrum. One preferred embodiment of the present invention includes an optical filter with a fixed wavelength filtering response that is inserted within the system along an optical path to suppress ASE. One preferred embodiment of the present invention includes an optical filter with a fixed wavelength filtering response that is placed after the VCL or an amplifier output along an optical path to shape the spectrum of emission. One preferred embodiment of the present invention includes an optical filter with a fixed wavelength filtering response that is placed after the VCL or an amplifier output along an optical path to reduce ASE. Another preferred embodiment of the present invention uses only active devices, only passive devices, or mixing any combination of active and passive devises for affecting the spectrum.

Figure 54:
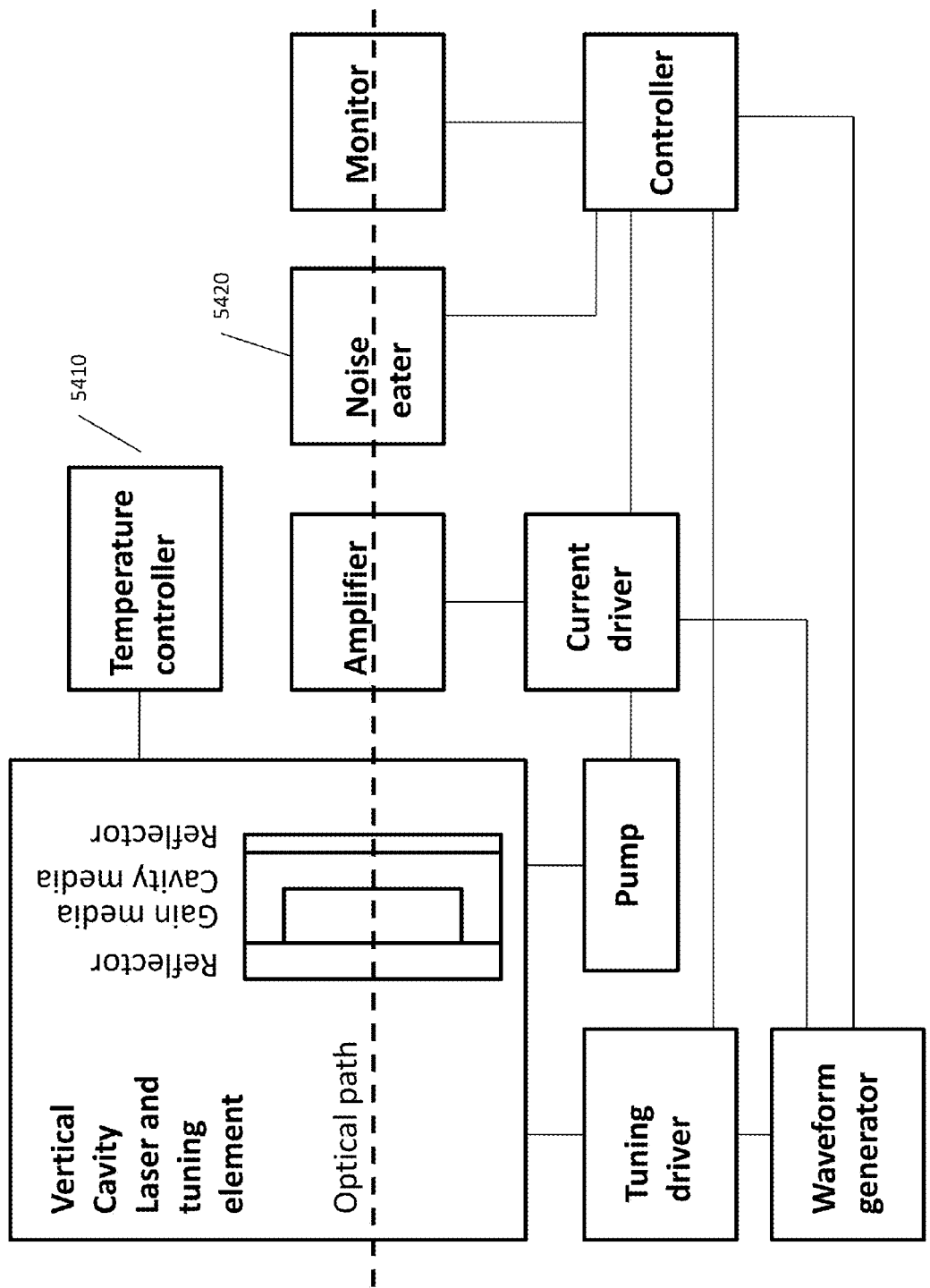
FIG. 54 is a block diagram of a closed loop wavelength tuning subsystem with temperature controlled gain material and a noise eater to reduce laser noise.

The behavior of the gain materials in the tunable source is influenced by operating temperature. One preferred embodiment of the present invention includes a means for thermal regulation, a temperature controller 5410, to temperature regulate one or more gain materials to achieve increased output emission power, as illustrated in FIG. 54. One preferred embodiment of the present invention includes a means for thermal regulation to temperature regulate one or more gain materials to achieve a preferred emission spectrum. One preferred embodiment of the present invention includes a means for thermal regulation to temperature regulate one or more gain materials to achieve decreased emission noise. The means for thermal regulation can be active or passive. The means for thermal regulation can be open or closed loop controlled. Examples of thermal regulation include but are not limited to: a thermal electric cooling element (TEC), a TEC combined with temperature sensor and feedback loop, a TEC operated in the open loop, liquid cooling combined with a temperature sensor and operated in the closed loop, liquid cooling operated in the open loop, heat sinking, fans, convective heat removing devices, conductive heat removing devices, or any other device or method known in the art of thermal management.

Generally, noise in the electronics can degrade the quality of the data. The preferred embodiment of the present invention manages the noise in the electronics to levels below that which affects the quality of the image. It is also possible that a noise eater 5420 comprising a detector and feedback loop adjusts the output current of the current driver to reduce laser noise, as illustrated in FIG. 54.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. An optical imaging system, comprising:
   a tunable source generating output optical radiation, the tunable source comprising a wavelength tunable vertical cavity laser (VCL), the VCL comprising a first and second laser mirror that form a laser cavity having a cavity length, an actuator configured to vary the laser cavity length, the VCL generating a single longitudinal mode lasing output that is tunable over an emission wavelength range for generating wavelength sweeps at a sweep repetition rate, wherein the laser cavity free spectral range is at least as wide as the emission wavelength range and the tuning over the entire emission wavelength range is mode hop free, and wherein the actuator and VCL are capable of operating over at least a 12% variation in the sweep repetition rate;
   a tuning driver, the tuning driver being capable of generating one or more wavelength tuning waveforms to affect the actuator which determines a sweep trajectory, a sweep speed, the sweep repetition rate, a sweep linearity, and the emission wavelength range;
   a current driver that supplies current to a gain material within the tunable source to adjust output optical radiation power;
   a monitoring detector configured to measure attributes of a tuning response of the tunable source and provide feedback to correct for disturbances to the tunable source or to generate the one or more wavelength tuning waveforms;
   an optical interferometer with a reference arm and a sample arm illuminated by said tunable source;
   one or more optical detectors that convert optical interference fringe signals from the optical interferometer into electric analog signals;
   a data acquisition device to convert the electric analog signals output from the one or more detectors into digital data.

2. The optical imaging system of claim 1, wherein the VCL is a vertical cavity surface-emitting laser (VCSEL).

3. The optical imaging system of claim 1, wherein the tunable source further comprises a pump laser and the VCL is an optically pumped VCL.

4. The optical imaging system of claim 1, wherein the VCL is an electrically pumped VCL.

5. The optical imaging system of claim 1, wherein the tunable source further comprises a pump laser and one or more optical amplifiers to increase output optical radiation power and the VCL is an optically pumped VCL.

6. The optical imaging system of claim 1, wherein the tunable source further comprises one or more optical amplifiers to increase output optical radiation power and the VCL is an electrically pumped VCL.

7. The optical imaging system of claim 1, wherein a center wavelength of the emission wavelength range is between 750 nm and 970 nm.

8. The optical imaging system of claim 1, wherein a center wavelength of the emission wavelength range is between 970 nm and 1100 nm.

9. The optical imaging system of claim 1, wherein a center wavelength of the emission wavelength range is between 1200 nm and 1600 nm.

10. The optical imaging system of claim 1, wherein the actuator is an electrostatically actuated microelectromechanical systems (MEMS) structure moving at least one of the first and second laser mirror defining the laser cavity length of the VCL.

11. The optical imaging system of claim 1, wherein the one or more wavelength tuning waveforms sweep the VCL at a predominately fixed repetition rate.

12. The optical imaging system of claim 1, wherein the one or more wavelength tuning waveforms sweep the VCL over a predominately fixed wavelength tuning range.

13. The optical imaging system of claim 1, wherein the one or more wavelength tuning waveforms are variable, and wherein the actuator is driven with the one or more variable wavelength tuning waveforms to achieve different operating modes with respect to sweep repetition rate.

14. The optical imaging system of claim 1, wherein the wavelength tuning waveforms are variable, and wherein the actuator is driven with the one or more variable wavelength tuning waveforms to achieve different operating modes with respect to sweep range.

15. The optical imaging system of claim 1, wherein the one or more wavelength tuning waveforms alter the tuning response of the tuning actuator from the actuator's natural dynamics.

16. The optical imaging system of claim 1, wherein the one or more wavelength tuning waveforms are calculated from a combination of basis functions, the one or more wavelength tuning waveforms altering the tuning response of the actuator from the actuator's natural dynamics.

17. The optical imaging system of claim 1, wherein the one or more wavelength tuning waveforms alter the tuning response of the actuator from the actuator's natural dynamics to achieve a tuning response that is preferable for imaging by improving at least one of the following: sweep repetition rate, sweep speed, sweep acceleration, sweep range, sweep linearity, and sweep duty cycle.

18. The optical imaging system of claim 1, further comprising a controller configured to generate the one or more wavelength tuning waveforms based on a given maximum A/D sampling clock rate.

19. The optical imaging system of claim 1, wherein the tunable source comprises at least one optical amplifier to generate higher output optical radiation power.

20. The optical imaging system of claim 1, wherein the current of the current driver is adjusted as a function of time to spectrally shape the output optical radiation.

21. The optical imaging system of claim 1, wherein the current of the current driver is adjusted as a function of time to spectrally shape the output optical radiation to compensate for optical properties of a sample.

22. The optical imaging system of claim 1, wherein the current of the current driver is adjusted as a function of time to spectrally shape the output optical radiation to optimize light exposure to a sample.

23. The optical imaging system of claim 1, wherein the current of the current driver is adjusted as a function of time to blank out either a forwards or a backwards sweep of the tunable source output optical radiation.

24. The optical imaging system of claim 1, further comprising a processor configured to check for saturation in the digital data and adjust the current to the gain material if saturation is found.

25. The optical imaging system of claim 1, further comprising a processor configured to collect the digital data into a data set, check for saturation in the digital data within the data set, and reimage an object or sample with the current to the gain material adjusted at locations in the data set where saturation was found, and acquire new digital data at the adjusted current levels.

26. The optical imaging system of claim 1, wherein the monitoring detector comprises a wavelength dependent component for splitting the light as a function of wavelength into multiple channels and the relative power of the different channels of light measured.

27. The optical imaging system of claim 1, wherein the monitoring detector comprises a wavelength dependent component for splitting the light as a function of wavelength into multiple channels and the relative power of the different channels of light measured to estimate the wavelength vs. time of the sweep.

28. The optical imaging system of claim 1, wherein the monitoring detector comprises a wavelength dependent coupler, beam splitter, or filter for splitting the light as a function of wavelength into multiple channels and two detector diodes to measure the relative power of the different channels of light to estimate the wavelength vs. time of the sweep.

29. The optical imaging system of claim 1, wherein an optical path delay of the reference arm is adjustable.

30. The optical imaging system of claim 1, further comprising an optical clocking module that comprises a clocking interferometer and a clocking detector that generates an optical clock signal to clock the data acquisition device.

31. The optical imaging system of claim 30, wherein the optical clock signal from the optical clocking module is reduced in frequency by frequency division or electrical counting to support different sweep trajectories of the tunable source.

32. The optical imaging system of claim 30, wherein the optical clocking module comprises an interferometer with an adjustable path delay to support variable measurement imaging ranges within a data acquisition bandwidth.

33. The optical imaging system of claim 1, further comprising an optical clocking module that comprises a clocking interferometer and a clocking detector that generates optical clock signals to clock the data acquisition device at predominately equal or repeatable optical k-intervals (wavenumber intervals).

34. The optical imaging system of claim 30, wherein the optical clocking module supports different sweep trajectories by adjusting an optical path delay of the clocking interferometer.

35. The optical imaging system of claim 1, further comprising a clocking interferometer and a detector, wherein the clocking interferometer and the clocking detector generate a clocking signal, wherein an optical path delay in the clocking interferometer is adjustable in length.

36. The optical imaging system of claim 1, further comprising a means for generating a trigger signal, wherein the trigger signal is synchronized with the tuning of the tunable source and used for proper A/D acquisition data alignment.

37. The optical imaging system of claim 1, further comprising a means for generating an optical wavelength signal, wherein the optical wavelength signal is used for proper A/D acquisition data alignment.

38. The optical imaging system of claim 37, further comprising a fiber Bragg grating (FBG), wherein the optical wavelength signal is generated by the fiber Bragg grating (FBG).

39. The optical imaging system of claim 1, wherein the tunable source has a coherence length longer than 30 mm when the laser output optical radiation frequency is continuously tuned by the one or more wavelength tuning waveforms.

40. The optical imaging system of claim 1, further comprising a controller configured to implement a closed loop control to maintain the desired sweep trajectory in the presence of environmental changes, temperature changes, internal charging, aging of the tunable source, or any other perturbation to the actuation or dynamics of the tunable source.

41. The optical imaging system of claim 1, further comprising a controller configured to implement a closed loop control to maintain the desired sweep trajectory in the presence of environmental changes, temperature changes, internal charging, aging of the device or other perturbation, the closed loop control reading a wavelength sensitive trigger signal and appropriately adjusting the one or more wavelength tuning waveforms.

42. The optical imaging system of claim 1, further comprising:
an optional processing unit configured to process the digital data into processed digital data
a means for storing the digital data or processed digital data or both.

43. The optical imaging system of claim 1, further comprising:
a means for processing the digital data into images;
a means for displaying the images.

44. A method for generating a wavelength tuning waveform of an optical imaging system, comprising: a tunable source generating output optical radiation, the tunable source comprising a wavelength tunable vertical cavity laser (VCL), the VCL comprising a first and second laser mirror that form a laser cavity having a cavity length, an actuator configured to vary the laser cavity length, the VCL generating a single longitudinal mode lasing output that is tunable over an emission wavelength range for generating wavelength sweeps at a sweep repetition rate, wherein the laser cavity free spectral range is at least as wide as the emission wavelength range and the tuning over the entire emission wavelength range is mode hop free, and wherein the actuator and VCL are capable of operating over at least a 12% variation in the sweep repetition rate; a tuning driver, the tuning driver being capable of generating one or more wavelength tuning waveforms to affect the actuator which determines a sweep trajectory, a sweep speed, the sweep repetition rate, a sweep linearity, and the emission wavelength range; a current driver that supplies current to a gain material within the tunable source to adjust output optical radiation power; a monitoring detector configured to measure attributes of a tuning response of the tunable source and provide feedback to correct for disturbances to the tunable source or to generate the one or more wavelength tuning waveforms; an optical interferometer with a reference arm and a sample arm illuminated by said tunable source; one or more optical detectors that convert optical interference fringe signals from the optical interferometer into electric analog signals; and a data acquisition device to convert the electric analog signals output from the one or more detectors into digital data, the method comprising the steps of:
expressing the wavelength tuning waveform as a function of adjustable input parameter values to create a tuning waveform expression;
applying the wavelength tuning waveform to the actuator or a mathematical model of the actuator dynamics to generate at least one experimental measurement or simulated wavelength sweep;
calculating a value of a performance metric or an objective function based on the at least one experimental measurement or the simulated wavelength sweep;
adjusting the input parameter values to optimize the value of the performance metric or objective function.

45. The method of claim 44, wherein the tuning waveform expression comprises a DC offset as one of the input parameter values.

46. The method of claim 44, wherein the tuning waveform expression comprises a summation of sinusoidal functions with different frequencies, the sinusoidal functions having adjustable amplitude and phase as at least some of the input parameters values.

47. The method of claim 44, wherein the tuning waveform expression comprises a chirped cosine function with adjustable input values as at least some of the input parameter values.

48. The method of claim 44, wherein the tuning waveform expression comprises mathematical functions with input values as at least some of the input parameter values.

49. The method of claim 44, wherein the at least one experimental measurement is a wavelength vs. time response from the tunable source emission or simulated output as the tuning element sweeps.

50. The method of claim 44, wherein the performance metric or objective function comprises a measure of the difference between the experimental or simulated sweep trajectory and a desired sweep trajectory, where any measure of closeness to the desired trajectory can be used as the metric, including, but not limited to the maximum tracking error, sum of squared differences of tracking error, and any norm on the tracking error.

51. The method of claim 44, wherein the steps are repeated multiple times and a correction applied to the input parameter values for each iteration.

52. The method of claim 44, wherein an optimization algorithm iterates the steps until a termination criterion is met.

* * * * *